(12) United States Patent
Noel et al.

(10) Patent No.: US 7,127,357 B1
(45) Date of Patent: Oct. 24, 2006

(54) CRYSTAL STRUCTURE OF WW DOMAINS AND METHODS OF USE THEREOF

(75) Inventors: Joseph P. Noel, San Diego, CA (US); Mark A. Verdecia, San Diego, CA (US)

(73) Assignee: The Salk Institute for Biological Studies, La Jolla, CA (US)

(*) Notice: Subject to any disclaimer, the term of this patent is extended or adjusted under 35 U.S.C. 154(b) by 731 days.

(21) Appl. No.: 09/733,773

(22) Filed: Dec. 8, 2000

(51) Int. Cl.
G06N 3/00 (2006.01)
G06N 7/00 (2006.01)
G06G 7/58 (2006.01)

(52) U.S. Cl. ............................. 702/27; 702/2; 702/19; 530/329; 530/350; 435/233

(58) Field of Classification Search ................... 702/19
See application file for complete search history.

(56) References Cited

U.S. PATENT DOCUMENTS 4,880,635 A 11/1989 Janoff et al.
6,495,376 B1 * 12/2002 Lu et al. .................... 436/501

FOREIGN PATENT DOCUMENTS

WO WO 91/02805 3/1991
WO WO 91/19501 12/1991

OTHER PUBLICATIONS

Verdecia et al. (Nature Structural Biology (2000) Aug., vol. 7, No. 8, pp. 639-643).*
Marcias et al (FEBS Letters (2000) vol. 513, pp. 30-37).*
Klebe (Journal of Molecular Medicine (2000) vol. 78, pp. 269-281).*
Bednarek, et al., "WWOX, a Novel WW Domain-containing Protein Maping to Human Chromosome 16q23.3-24.1, a Region Frequently Affected in Breast Cancer," Cancer Research, 60:2140-2145 (2000).
Brünger, et al., "Crystallography & NMR System: A New Software Suite for Macromolecular Structure Determination," Acta Cryst., D54:905-921 (1998).
Brzozowski, et al., "Molecular basis of agonism and antagonism in the oestrogen receptor," Letters to Nature, 389:753-758 (1997).
Campbell, et al., "The Human PIN1 Peptidyl-Prolyl cis/trans Isomerase Gene Maps to Human Chromosome 19p13 and the Closely Related PIIN1L Gene to 1p31," Genomics, 44:157-162 (1997).
Cohen, et al., "Molecular Modeling Software and Methods for Medicinal Chemistry," Journal of Medicinal Chemistry, 33,(3):883-894 (1990).
Hanes, et al., "Sequence and Mutational Anaysis of ESS1, a Gene Essential for Growth in Saccharomyces cerevisiae," Yeast, 5:55-72 (1989).
Hani, et al., "PTF1 encodes an essential protein in Saccharomyces cerevisiae, which shaows strong homology with a new putative family of PPlases," FEBS Letters, 365:198-202 (1995).

Komuro, et al., "Npw38, a novel nuclear protein possessing a WW domain capable of activating basal transcription," Nuleic Acids Research, 27(9):1957-1965 (1999).
Kuriyan & Cowburn, "Modular Peptide Recognition Domains in Eukaryotic Signaling," Annu. Rev. Biophys. Biomol. Struct., 26:259-288 (1997).
Laskowski, R.A., "PROCHECK: a program to check the sterochemical quality of protein structures," J. Appl. Cryst., 26:283-291 (1993).
Lee, et al., "New Inhibitors of Thrombin and Other Trypsin-like Proteases: Hydrogen Bonding of an Aromtaic Cyano Group with a Backbone Amide of the $P_1$ Binding Site Replaces Binding of a Basic Side Chain," Biochemistry, 36:13180-13186 (1997).
Lu, et al., "A human peptidyl-prolyl isomerase essential for regulation of mitosis," Letters to Nature, 380:544-547 (1996).
Macias, et al., "Structure of the WW domain of a kinase-associated protein complexed with a proline-rich peptide," Letters to Nature, 382:646-649 (1996).
Maleszka, et al., "The Drosophila melanogaster dodo (dod) gene, conserved in humans, is funtionally interchangeable with the ESS1 cell division gene of Saccharomyces cerevisiae," Proc. Natl. Acad. Sci ISA, 93:447-451 (1996).
Meng, et al., "Automated Docking with Grid-Based Energy Evaluation," Journal of Computational Chemistry, 13(4):505-524 (1992).
Mohammadi, et al., "Structures of the Tyrosine Kinase Domain of Fibroblast Growth Factor Receptor in Complex with Inhibitors," Science, 276:955-960 (1997).
Navaza, J., "AMoRe: An automated package for molecular replacememt." Acta Crystallogr., A50:157-163, 1994.
Nicholls, et al., "Protein Folding and Association: Insightes From the Interfacials and Termodynamic Properties of Hydrocarbons," PROTEINS: Structure, Function and Genetics, 11:281-296 (1991).
Plowman, et al., "The protein kinases of Caenorhabditis elegans: A model for signal transduction in multicellular organisms," PNAS, 96(24):13603-13610 (1999).
Rahfeld, et al., "Confirmation of the existence of a third family among peptidyl-prolyl cisltranns isomerases Amino acid sequence and recombinant production of parvulin," FEBS Letters, 352:180-184 (1994).
Ranganathan, "Structural and Functional Analysis of the Mitotic Rotamase Pin1 Suggests Substrate Recognition Is Phosphorylation Dependent," Cell, 89:875-886 (1997).
Staub and Rotin, "WW domains," Structure, 4(5):495-499 (1996).
Vinson et al., "Interactions of Acanthamoeba profilin with actin and nucleotides bound to actin." Biochemistry. 37:10871-10880, 1998.
Yaffe, et al., "Sequence-Specific and Phosphorylation-Dependent Proline Isomerization: A Potential Mitotic Regulatory Mechanism," Science, 278:1957-1960 (1997).

* cited by examiner

Primary Examiner—Marjorie A. Moran
Assistant Examiner—Lori A. Clow
(74) Attorney, Agent, or Firm—Foley & Lardner LLP; Stephen E. Reiter

(57) ABSTRACT

A WW domain crystal structure of Pin1 is provided. In addition, methods of using the crystal structure and atomic coordinates for the development of WW domain binding agents is also provided. Also provided are computer programs on computer readable medium for use in developing WW domain binding agents.

14 Claims, 6 Drawing Sheets

SEQUENCE LISTING

```
<160> NUMBER OF SEQ ID NOS: 32

<210> SEQ ID NO 1
<211> LENGTH: 163
<212> TYPE: PRT
<213> ORGANISM: Homo sapiens
<220> FEATURE:
<221> NAME/KEY: PEPTIDE
<222> LOCATION: (1)..(163)
<223> OTHER INFORMATION: Pin1

<400> SEQUENCE: 1
```

Met Ala Asp Glu Glu Lys Leu Pro Pro Gly Trp Glu Lys Arg Met Ser
 1               5                  10                  15

Arg Ser Ser Gly Arg Val Tyr Tyr Phe Asn His Ile Thr Asn Ala Ser
                20                  25                  30

Gln Trp Glu Arg Pro Ser Gly Asn Ser Ser Ser Gly Gly Lys Asn Gly
            35                  40                  45

Gln Gly Glu Pro Ala Arg Val Arg Cys Ser His Leu Leu Val Lys His
        50                  55                  60

Ser Gln Ser Arg Arg Pro Ser Ser Trp Arg Gln Glu Lys Ile Thr Arg
65                  70                  75                  80

Thr Lys Glu Glu Ala Leu Glu Leu Ile Asn Gly Tyr Ile Gln Lys Ile
                85                  90                  95

Lys Ser Gly Glu Glu Asp Phe Glu Ser Leu Ala Ser Gln Phe Ser Asp
            100                 105                 110

Cys Ser Ser Ala Lys Ala Arg Gly Asp Leu Gly Ala Phe Ser Arg Gly
        115                 120                 125

Gln Met Gln Lys Pro Phe Glu Asp Ala Ser Phe Ala Leu Arg Thr Gly
    130                 135                 140

Glu Met Ser Gly Pro Val Phe Thr Asp Ser Gly Ile His Ile Ile Leu
145                 150                 155                 160

Arg Thr Glu

```
<210> SEQ ID NO 2
<211> LENGTH: 38
<212> TYPE: PRT
<213> ORGANISM: Homo sapiens
<220> FEATURE:
<221> NAME/KEY: DOMAIN
<222> LOCATION: (1)..(38)
<223> OTHER INFORMATION: Ww Domain of Pin1

<400> SEQUENCE: 2
```

Met Ala Asp Glu Glu Lys Leu Pro Pro Gly Trp Glu Lys Arg Met Ser
 1               5                  10                  15

Arg Ser Ser Gly Arg Val Tyr Tyr Phe Asn His Ile Thr Asn Ala Ser
                20                  25                  30

Gln Trp Glu Arg Pro Ser

```
<210> SEQ ID NO 3
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<221> NAME/KEY: MOD_RES
<222> LOCATION: (5)..(5)
<223> OTHER INFORMATION: PHOSPHORYLATION

<400> SEQUENCE: 3

Tyr Ser Pro Thr Ser Pro Ser
1               5

<210> SEQ ID NO 4
<211> LENGTH: 9
<212> TYPE: PRT
<213> ORGANISM: ARTIFICIAL SEQUENCE
<220> FEATURE:
<223> OTHER INFORMATION: Description of Artificial Sequence:
      Modification of Homo sapiens Pin1 WW domain
<223> OTHER INFORMATION: YAB65-PPXY peptide complex
<221> NAME/KEY: VARIANT
<222> LOCATION: (6)..(6)
<223> OTHER INFORMATION: Xaa is any amino acid (Pro in Figure 4a & 4b)

<400> SEQUENCE: 4

Gly Thr Pro Pro Pro Xaa Tyr Thr Val
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: Pintide Pin1-Peptide Complex

<400> SEQUENCE: 5

Trp Phe Tyr Ser Pro Phe Leu Glu
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: Pintide Pin1-Peptide Complex
<221> NAME/KEY: MOD_RES
<222> LOCATION: (4)..(4)
<223> OTHER INFORMATION: PHOSPHORYLATION

<400> SEQUENCE: 6

Trp Phe Tyr Ser Pro Phe Leu Glu
1               5

<210> SEQ ID NO 7
<211> LENGTH: 6
<212> TYPE: PRT
<213> ORGANISM: Homo sapiens
<220> FEATURE:
<221> NAME/KEY: MOD_RES
<222> LOCATION: (4)..(4)
```

```
<223> OTHER INFORMATION: PHOSPHORYLATION

<400> SEQUENCE: 7

Val Pro Arg Thr Pro Val
1               5

<210> SEQ ID NO 8
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 8

Tyr Leu Gly Ser Pro Ile
1               5

<210> SEQ ID NO 9
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 9

Leu Tyr Arg Ser Pro Ser
1               5

<210> SEQ ID NO 10
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 10

Gly Ser Ser Ser Pro Val
1               5

<210> SEQ ID NO 11
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 11

Pro Pro Ala Thr Pro Pro
1               5

<210> SEQ ID NO 12
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 12
```

-continued

```
Pro Pro Gly Ser Pro Pro
1               5

<210> SEQ ID NO 13
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 13

Ser Thr Ser Thr Pro Arg
1               5

<210> SEQ ID NO 14
<211> LENGTH: 7
<212> TYPE: PRT
<213> ORGANISM: Homo sapiens

<400> SEQUENCE: 14

Tyr Ser Pro Thr Ser Pro Ser
1               5

<210> SEQ ID NO 15
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 15

Tyr Ser Pro Thr Ser Pro Ser
1               5

<210> SEQ ID NO 16
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION

<400> SEQUENCE: 16

Tyr Ser Pro Thr Ser Pro Ser
1               5

<210> SEQ ID NO 17
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<221> NAME/KEY: MOD_RES
<222> LOCATION: (5)..(5)
<223> OTHER INFORMATION: PHOSPHORYLATION

<400> SEQUENCE: 17

Tyr Ser Pro Thr Ser Pro Ser
1               5

<210> SEQ ID NO 18
```

-continued

```
<211> LENGTH: 34
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: hPin1 peptide complex

<400> SEQUENCE: 18

Lys Leu Pro Pro Gly Trp Glu Lys Arg Met Ser Arg Ser Ser Gly Arg
 1               5                  10                  15

Val Tyr Tyr Phe Asn His Ile Thr Asn Ala Ser Gln Trp Glu Arg Pro
            20                  25                  30

Ser Gly

<210> SEQ ID NO 19
<211> LENGTH: 34
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: Sc Ess1 peptide complex

<400> SEQUENCE: 19

Gly Leu Pro Thr Pro Trp Thr Val Arg Tyr Ser Lys Ser Lys Lys Arg
 1               5                  10                  15

Glu Tyr Phe Phe Asn Pro Glu Thr Lys His Ser Gln Trp Glu Glu Pro
            20                  25                  30

Glu Gly

<210> SEQ ID NO 20
<211> LENGTH: 34
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: d Dodo peptide complex

<400> SEQUENCE: 20

Gln Leu Pro Asp Gly Trp Glu Lys Arg Thr Ser Arg Ser Thr Gly Met
 1               5                  10                  15

Ser Tyr Tyr Leu Asn Met Tyr Thr Lys Glu Ser Gln Trp Asp Gln Pro
            20                  25                  30

Thr Glu

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: m Pin1 peptide complex

<400> SEQUENCE: 21

Lys Leu Pro Pro Gly Trp Glu Lys Arg Met Ser Arg Ser Ser Gly Arg
 1               5                  10                  15

Val Tyr Tyr Phe Asn His Ile Thr Asn Ala Ser Gln Trp Glu Arg Pro
            20                  25                  30

Ser Gly
```

-continued

<210> SEQ ID NO 22
<211> LENGTH: 34
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: Kn Pin1 peptide complex

<400> SEQUENCE: 22

Gly Leu Pro Ala Gly Trp Glu Val Arg His Ser Asn Ser Lys Asn Leu
1               5                   10                  15

Pro Tyr Tyr Phe Asn Pro Ala Thr Arg Glu Ser Arg Trp Glu Pro Pro
            20                  25                  30

Ala Asp

<210> SEQ ID NO 23
<211> LENGTH: 33
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: h YAP65 peptide complex

<400> SEQUENCE: 23

Pro Leu Pro Ala Gly Trp Glu Met Ala Lys Thr Ser Ser Gly Gln Arg
1               5                   10                  15

Tyr Phe Leu Asn His Ile Asp Gln Thr Thr Trp Gln Asp Pro Arg
            20                  25                  30

Lys

<210> SEQ ID NO 24
<211> LENGTH: 33
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: h Dryst peptide complex

<400> SEQUENCE: 24

Ser Val Gln Gly Pro Trp Glu Arg Ala Ile Ser Pro Asn Lys Val Pro
1               5                   10                  15

Tyr Tyr Ile Asn His Glu Thr Gln Thr Thr Cys Trp Asp His Pro Lys
            20                  25                  30

Met

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: Sc Rsp5-WW1 peptide complex

<400> SEQUENCE: 25

Leu Pro Pro Gly Trp Glu Arg Arg Thr Asp Asn Phe Gly Arg Thr Tyr
1               5                   10                  15

Tyr Val Asp His Asn Thr Arg Thr Thr Thr Trp Lys Arg Pro Thr Leu
            20                  25                  30

<210> SEQ ID NO 26

```
<211> LENGTH: 33
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: Sc Rsp5-WW2 peptide complex

<400> SEQUENCE: 26

Glu Leu Pro Ser Gly Trp Glu Gln Arg Phe Thr Pro Glu Gly Arg Ala
1               5                   10                  15

Tyr Phe Val Asp His Asn Thr Arg Thr Thr Thr Trp Val Asp Pro Arg
            20                  25                  30

Arg

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: Sc Rsp5-WW3 peptide complex

<400> SEQUENCE: 27

Pro Leu Pro Ser Gly Trp Glu Met Arg Leu Thr Asn Thr Ala Arg Val
1               5                   10                  15

Tyr Phe Val Asp His Asn Thr Lys Thr Thr Thr Trp Asp Asp Pro Arg
            20                  25                  30

Leu

<210> SEQ ID NO 28
<211> LENGTH: 33
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: m NEDD4-WW1 peptide complex

<400> SEQUENCE: 28

Pro Leu Pro Pro Gly Trp Glu Glu Arg Gln Asp Val Leu Gly Arg Thr
1               5                   10                  15

Tyr Tyr Val Asn His Glu Ser Arg Arg Thr Gln Trp Lys Arg Pro Ser
            20                  25                  30

Pro

<210> SEQ ID NO 29
<211> LENGTH: 33
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: m NEDD4-WW2 peptide complex

<400> SEQUENCE: 29

Gly Leu Pro Pro Gly Trp Glu Glu Lys Gln Asp Asp Arg Gly Arg Ser
1               5                   10                  15

Tyr Tyr Val Asp His Asn Ser Lys Thr Thr Thr Trp Ser Lys Pro Thr
            20                  25                  30

Met
```

```
<210> SEQ ID NO 30
<211> LENGTH: 33
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: m NEDD4-WW3 peptide complex

<400> SEQUENCE: 30

Pro Leu Pro Pro Gly Trp Glu Glu Arg Thr His Thr Asp Gly Arg Val
1               5                   10                  15

Phe Phe Ile Asn His Asn Ile Lys Lys Thr Gln Trp Glu Asp Pro Arg
            20                  25                  30

Leu

<210> SEQ ID NO 31
<211> LENGTH: 33
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: m NEDD4-WW4 peptide complex

<400> SEQUENCE: 31

Pro Leu Pro Glu Gly Trp Glu Ile Arg Tyr Thr Arg Glu Gly Val Arg
1               5                   10                  15

Tyr Phe Val Asp His Asn Thr Arg Thr Thr Thr Phe Lys Asp Pro Arg
            20                  25                  30

Asn

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence:
      Modification of Homo sapiens Pin1 WW domain
<223> OTHER INFORMATION: h FE65 peptide complex

<400> SEQUENCE: 32

Asp Leu Pro Ala Gly Trp Met Arg Val Gln Asp Thr Ser Gly Thr Tyr
1               5                   10                  15

Tyr Trp His Ile Pro Thr Gly Thr Thr Gln Trp Glu Pro Pro Gly Arg
            20                  25                  30
```

CRYSTAL STRUCTURE OF WW DOMAINS AND METHODS OF USE THEREOF

This invention was made with government support under Contract No. NIH GM-57533 by the National Institutes of Health. The government has certain rights in the invention.

The U.S. Government may have certain rights in this invention pursuant to Grant No. GM57533 awarded by the USPHS.

FIELD OF THE INVENTION

The present invention relates to crystals of WW domains and more particularly to the high resolution structure of Pin1 WW domain obtained by X-ray diffraction. In addition, the invention relates to methods of using the structure coordinates of Pin1 WW domain and mutants thereof to screen and design compounds that bind to or interact with WW domains.

BACKGROUND

The process of designing potent and specific inhibitors has improved with the arrival of techniques for determining the three-dimensional structure of the enzyme to be inhibited. Usually a three-dimensional model of an enzyme is produced by the creation of a crystalline form of the purified enzyme which is then subjected to X-ray diffraction and analysis. While such procedures provide certain valuable information that can be used to design inhibitors, they suffer from a lack of knowledge about the amino acid residues critical for interaction with a substrate or a substrate mimic. In order to address these limitations, enzymes have more recently been co-crystallized with substrates, substrate mimics or known inhibitors of the enzyme's activity, thereby allowing the important interactions to be determined (see, for example, Mohammadi, et al., Science 276:955–960, 1997; Lee, et al., Biochemistry 36:13180–13186, 1997; Brzozowski, et al., Nature 389:753–758, 1997).

The peptidyl-prolyl cis-trans isomerases (PPIases), or rotamases, are a family of enzymes important in protein folding, assembly and transport. They act as catalysts to promote isomerization about the peptidyl-prolyl bond, which can have profound effects on protein function.

PPIases are divided into three classes, cyclophilins, FK-506 binding proteins (FKBPs) and the Pin1/parvulin class. While cyclophilins and FKBPs are distinguished by their ability to bind immunosuppressant molecules cyclosporin and FK-506, respectively, the Pin1/parvulin class binds neither of these immunosupressants and is structurally unrelated to the other two classes. Known members of the Pin1/parvulin class include Pins 1–3 (Lu, et al., Nature 380:544–547, 1996), Pin-L (Campbell, et al., Genomics 44:157–162, 1997), parvulin (Rahfeld, et al., FEBS Letts 352:180–184, 1994), dodo (Maleszka, et al., Proc Natl Acad Sci USA 93:447–451, 1996) and Ess1/Pft1 (Hanes, et al., Yeast 5:55–72, 1989; and Hani, et al., FEBS Letts 365: 198–202, 1995).

Recent research suggests that members of the Pin1/parvulin class are essential modulators of the cell cycle, and mitosis in particular. Lu, et al., Nature 380:544–547, 1996 (incorporated by reference herein) reports that depletion of Pin1/Ess1 (a structural and functionally related protein to Pin1) in yeast or human cells induces mitotic arrest followed by apoptosis, indicating that enzymes in this class serve an essential function in cell division and proliferation.

The design of new, highly specific antimitotic agents represents an important need in the pharmaceutical industry. Such agents can serve as effective chemotherapeutic agents for the treatment of a variety of disorders characterized by inappropriate cell proliferation, including cancer and infectious diseases. The invention disclosed herein addresses this and related needs, as will become apparent upon review of the specification and appended claims.

SUMMARY OF THE INVENTION

A Pin1 WW domain crystal structure is provided. Methods of using the crystal structure and atomic coordinates for the development of WW domain binding agents is also provided. In addition, the disclosure provides computer programs on computer readable medium for use in developing WW domain binding agents.

BRIEF DESCRIPTION OF THE FIGURES

FIG. 1 collectively shows the overall architecture of human Pin1.

FIG. 2 collectively shows an enlarged view of the Pin1-CTD peptide binding interface.

FIG. 4 collectively shows representative WW domains.

DETAILED DESCRIPTION OF THE INVENTION

Figure 1A:
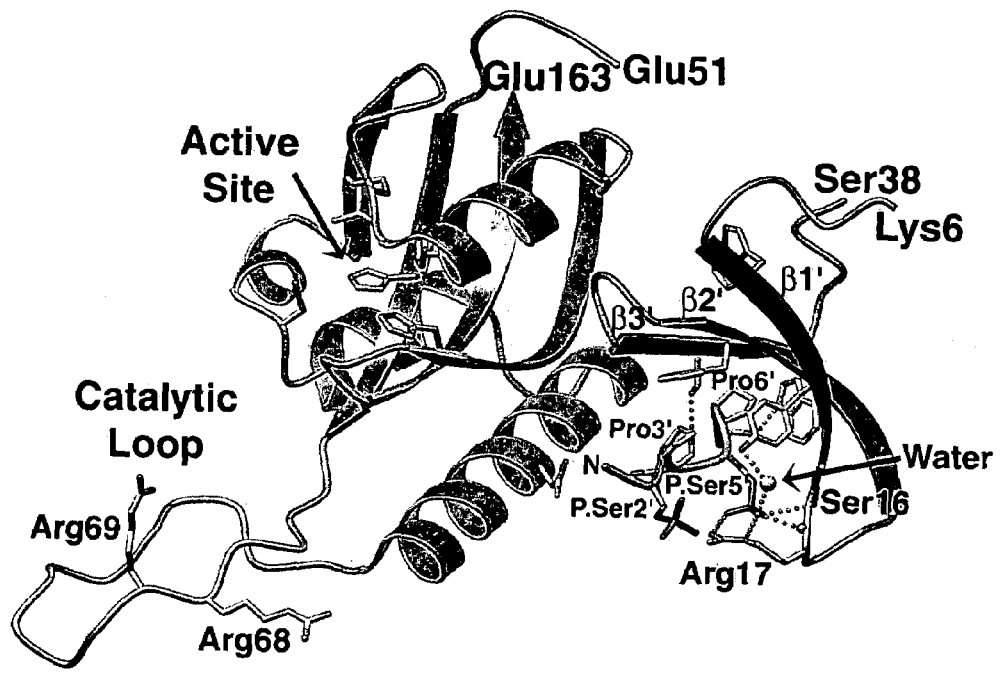
FIG. 1A shows the ribbon representation of the Pin1-C-Terminal Domain (CTD) peptide complex. Residues 39 to 50 are disordered. Apostrophes distinguish the WW domain from the PPIase domain. The CTD peptide backbone is in the region labeled as N, Pro3' and Pro6'. Residues of the CTD peptide are labeled with apostrophes. Atoms of carbon, nitrogen, phosphorus, oxygen, and sulfur are depicted. Dotted lines depict hydrogen bonds.

In accordance with the present invention, methods of identifying WW domain binding agents are provided. Invention methods include defining an interaction site of a WW domain based on a plurality of atomic coordinates of the WW domain, modeling a potential binding agent that fits spatially into said interaction site, contacting said potential binding agent with the WW domain in the presence of a WW domain substrate, and determining the ability of the potential binding agent to compete with the WW domain substrate for binding to the WW domain.

In another aspect, the invention provides a computer program on a computer readable medium, said computer program having instructions to cause a computer to model a potential binding agent that fits spatially into a WW domain interaction site defined by a plurality of atomic coordinates.

WW Domains

The WW domain is a 38–40 amino acid structural motif that functions as an interaction module in a diverse set of signaling proteins. The modular nature of WW domain interactions lends itself to classification into five distinct groups based upon current understanding of their binding specificity. Group I WW domains, exemplified by YAP65, recognize PPxY motifs2; Group II WW domains, like FE65, bind the PPLP motif. Group III WW domains, such as those found in a subset of FBPs, interact with PGM motifs. A fourth group represented by the WW domain of Pin1, specifically interact with phosphorylated serine or threonine residues amino-terminal to proline, or $^{phosphorylated}$SER-PRO (P.Ser-Pro) or $^{phosphorylated}$THR-PRO (P.Thr-Pro) motifs. Finally, the recently classified group V WW domains recognize PGR motifs. Pin1 contains an N-terminal WW domain and a C-terminal peptidyl-prolyl cis-trans isomerase domain connected by a flexible linker. Provided here are the functional and structural basis for WW domain binding to phosphorylated protein substrates based on the energetic and structural analysis of a Pin1-phosphopeptide complex.

Pin1 has been implicated in the regulation of a diverse set of mitotically phosphorylated proteins including Cdc25, Myt1, Wee1, Plk1, and Cdc27, and also Tau11. In addition, Pin1 and its homolog, Ess1p, have both been implicated in the regulation of the C-terminal domain (CTD) of RNA Polymerase II (Pol II) and they can both bind directly to the phosphorylated CTD. Phosphorylation of Ser-2' and/or Ser-5' on the multiple YSPTSPS heptad repeats in the CTD of Pol II by cyclin-dependent kinases (CDKs) converts Pol IIa to Pol IIo and initiates a cascade of transcriptional, processing, and splicing events linked to the elongating polymerase. Structural and functional analysis of Pin1 established that Pin1's PPIase domain (which belongs to the parvulin family of PPIases) catalyzes phosphorylation-dependent peptide bond isomerization in P.Ser-Pro segments. Finally, binding analyses demonstrate that the Pin1 WW domain acts as the predominant P.Ser/P.Thr-Pro binding motif.

One aspect of the invention resides in obtaining crystals of the WW domain of a Pin1 protein of sufficient quality to determine the three dimensional (tertiary) structure of the protein by X-ray diffraction methods. The knowledge obtained concerning Pin1 WW domain proteins can be used in the determination of the three dimensional structure of the binding domain of other WW domain containing proteins (e.g., Npw38 (Komuro et al., Nucleic Acid Res. 27(9): 1957–65, 1999). The binding domain can also be predicted by various computer models. Based on the structural coordinates of the WW domain (i.e., the three dimensional protein structure of the binding domain), as described herein, small molecules which mimic the functional binding of a WW domain protein to its ligands can be designed and synthesized. Accordingly, in one embodiment, the invention provides a method of "rational" drug design. Another approach to "rational" drug design is based on a lead compound that is discovered using high throughput screens; the lead compound is further modified based on a crystal stucture of the binding regions of the molecule in question. Accordingly, another aspect of the invention is to provide starting materials for the rational design of drugs which prevent or mimic the action of a WW domain (e.g., Pin1 WW domain) protein binding to its ligand.

Pin1's amino acid sequence is known (Lu et al., supra). The WW domain of Pin1 includes residues 1 to 39 and the PPIase domain includes residues 50–163 of Pin1. The term "amino acids" means the L-isomers of the naturally occurring amino acids or unnatural amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Unless specifically indicated, all amino acids referred to in this application are in the L-form.

The term "unnatural amino acids" means amino acids that are not naturally found in proteins. Examples of unnatural amino acids used herein, include racemic mixtures of selenocysteine and selenomethionine. In addition, unnatural amino acids include the D or L forms of nor-leucine, para-nitrophenylalanine, homophenylalanine, para-fluorophenylalanine, 3-amino-2-benzylpropionic acid, homoarginine, and D-phenylalanine.

The term "positively charged amino acid" includes any naturally occurring or unnatural amino acid having a positively charged side chain under normal physiological conditions. Examples of positively charged naturally occurring amino acids are arginine, lysine and histidine.

The term "negatively charged amino acid" includes any naturally occurring or unnatural amino acid having a negatively charged side chain under normal physiological conditions. Examples of negatively charged naturally occurring amino acids are aspartic acid and glutamic acid.

The term "hydrophobic amino acid" means any amino acid having an uncharged, nonpolar side chain that is relatively insoluble in water. Examples of naturally occurring hydrophobic amino acids are alanine, leucine, isoleucine, valine, proline, phenylalanine, tryptophan and methionine.

The term "hydrophilic amino acid" means any amino acid having an uncharged, polar side chain that is relatively soluble in water. Examples of naturally occurring hydrophilic amino acids are serine, threonine, tyrosine, asparagine, glutamine, and cysteine.

The term "crystal structure coordinates" refers to mathematical coordinates derived from mathematical equations related to the patterns obtained on diffraction of a monochromatic beam of X-rays by the atoms (scattering centers) of a protein molecule in crystal form. The diffraction data are used to calculate an electron density map of the repeating unit of the crystal. The electron density maps are used to establish the positions of the individual atoms within the unit cell of the crystal. The crystal structure coordinates of the Pin1 protein binding domain (e.g., the WW domain) are obtained from a Pin1 protein crystal having orthorhombic space group symmetry $P2_12_12$ with a=35.27 Å, b=43.90 Å, c=124.66 Å, $\alpha=\beta=\gamma=90°$. The coordinates of the Pin1 protein binding domain can also be obtained by means of computational analysis.

The term "selenomethione substitution" refers to the method of producing a chemically modified form of a crystal of Pin1. The Pin1 protein is expressed by bacteria in media that is depleted in methionine and supplemented with selenomethionine. Selenium is thereby incorporated into the crystal in place of methionine sulfurs. The location(s) of selenium are determined by X-ray diffraction analysis of the crystal. This information is used to generate the phase information used to construct a three-dimensional structure of the protein.

The term "heavy atom derivatization" refers to the method of producing a chemically modified form of the crystal of Pin1. A crystal is soaked in a solution containing heavy metal atom salts or organometallic compounds, which can diffuse through the crystal and bind to the surface of the protein. The location(s) of the bound heavy metal atom(s) are determined by X-ray diffraction analysis of the soaked crystal. This information is used to generate the phase information used to construct a three-dimensional structure of the protein.

The term "unit cell" refers to the basic parallelipiped shaped block. The entire volume of a crystal may be constructed by regular assembly of such blocks.

The term "space group" refers to the arrangement of symmetry elements of a crystal.

The term "molecular replacement" refers to a method that involves generating a preliminary model of a Pin1 crystal whose structure coordinates are not known, by orienting and positioning a molecule whose structure coordinates are known. Phases are then calculated from this model and combined with observed amplitudes to give an approximate Fourier synthesis of the structure whose coordinates are known.

The crystal structure coordinates of a Pin1 protein and its WW domain can be used to design compounds that bind to the protein and alter its physical or physiological properties in a variety of ways. The structure coordinates of the protein can also be used to computationally screen small molecule data bases for compounds that bind to the protein to develop competitive, uncompetitive and non-competitive inhibitors of Pin1 WW domain.

A "competitive" inhibitor is one that inhibits a WW domain activity (e.g., a Pin1 WW domain activity) by binding to the same kinetic form, of the WW domain, as its substrate binds—thus directly competing with the substrate for the active site of the WW domain. Competitive inhibition can be reversed completely by increasing the substrate concentration.

An "uncompetitive" inhibitor is one that inhibits WW domain activity (e.g., a Pin1 WW domain activity) by binding to a different kinetic form of the active site than does the substrate. Such inhibitors bind to a WW domain already bound with the substrate and not to the free enzyme. Uncompetitive inhibition cannot be reversed completely by increasing the substrate concentration.

A "non-competitive" inhibitor is one that can bind to either the free or substrate bound form of a WW domain.

Those of skill in the art may identify inhibitors as competitive, uncompetitive or non-competitive, by computer fitting enzyme kinetic data using standard equations according to Segel, I. H., Enzyme Kinetics, J. Wiley & Sons, (1975). It should also be understood that uncompetitive or non-competitive inhibitors according to this invention may bind to an accessory binding site.

Methods of using crystal structure data to design inhibitors of enzyme activity are known in the art. Thus, the crystal structure data provided herein can be used in the design of new or improved enzymatic inhibitors. For example, the Pin1 WW domain coordinates, provided herein, can be superimposed onto other available coordinates of similar enzymes which have inhibitors bound to them to give an approximation of the way these and related inhibitors might bind to Pin1 WW domains. Alternatively, computer programs employed in the practice of rational drug design can be used to identify compounds that reproduce interaction characteristics similar to those found between the Pin1 WW domain and the co-crystalized substrate mimic. Furthermore, detailed knowledge of the nature of binding site interactions allows for the modification of compounds to alter or improve solubility, pharmacokinetics, etc. without affecting binding activity.

Computer programs are widely available that are capable of carrying out the activities necessary to design compounds using the crystal structure information provided herein. Examples include, but are not limited to, the computer programs listed below:

Catalyst Databases™—an information retrieval program accessing chemical databases such as BioByte Master File, Derwent WDI and ACD;

Catalyst/HYPO™—generates models of compounds and hypotheses to explain variations of activity with the structure of drug candidates;

Ludi™—fits molecules into the active site of a protein by identifying and matching complementary polar and hydrophobic groups;

Leapfrog™—"grows" new ligands using an algorithm with parameters under the control of the user.

In addition, various general purpose machines may be used with programs written in accordance with the teachings herein, or it may be more convenient to construct more specialized apparatus to perform the operations. However, preferably the embodiment is implemented in one or more computer programs executing on programmable systems each comprising at least one processor, at least one data storage system (including volatile and non-volatile memory and/or storage elements), at least one input device, and at least one output device. The program is executed on the processor to perform the functions described herein.

Each such program may be implemented in any desired computer language (including machine, assembly, high level procedural, or object oriented programming languages) to communicate with a computer system. In any case, the language may be a compiled or interpreted language. The computer program will typically be stored on a storage media or device (e.g., ROM, CD-ROM, or magnetic or optical media) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Figure 5:
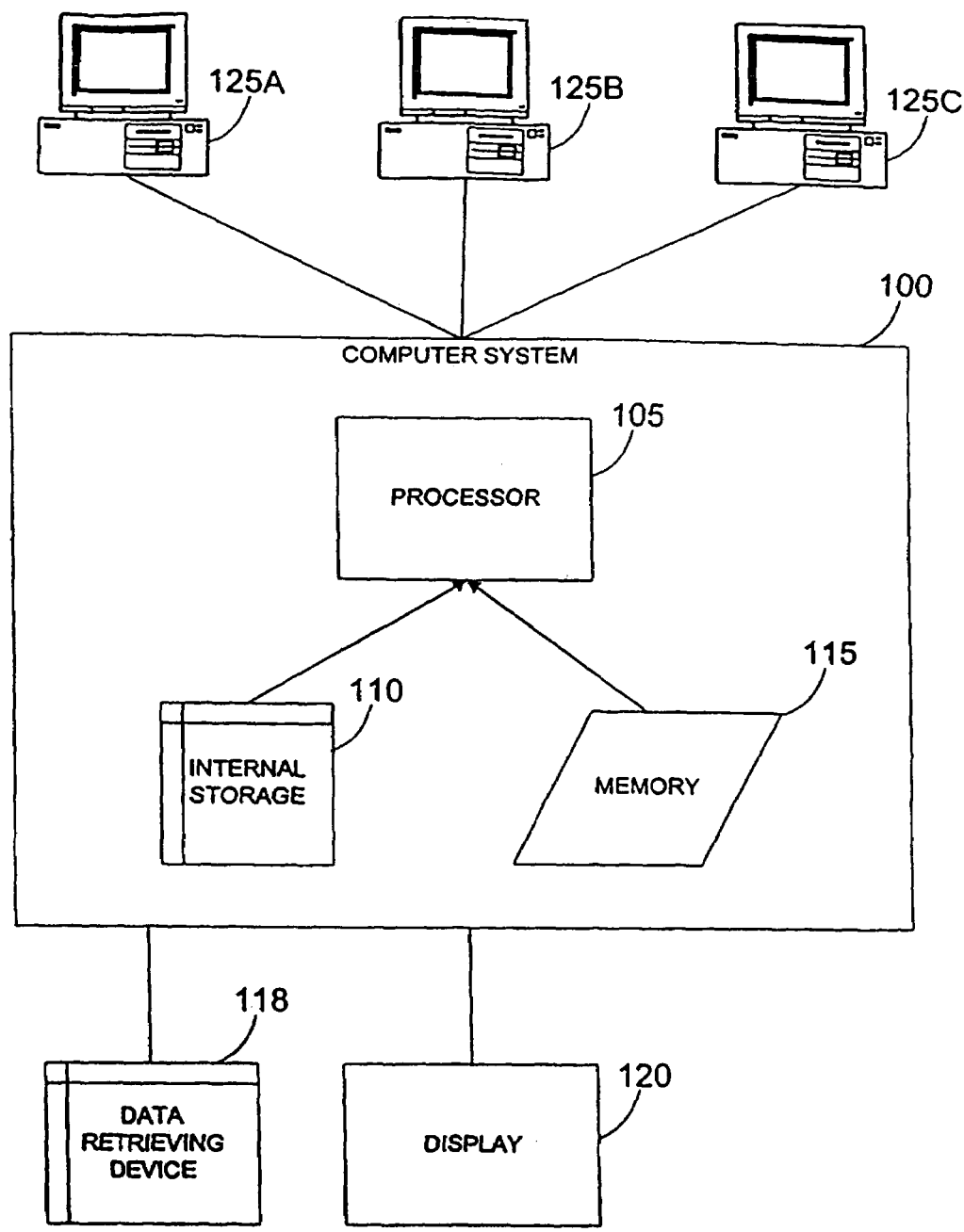
FIG. 5 is a block diagram of a computer system.

Embodiments of the invention include systems (e.g., internet based systems), particularly computer systems which store and manipulate the coordinate and sequence information described herein. One example of a computer system 100 is illustrated in block diagram form in FIG. 5. As used herein, "a computer system" refers to the hardware components, software components, and data storage components used to analyze the coordinates and sequences set forth in Table 1. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a–c in a network or wide area network to provide centralized access to the computer system 100.

Software for accessing and processing the coordinate and sequences of Table 1, (such as search tools, compare tools, and modeling tools etc.) may reside in main memory 115 during execution.

For the first time, the present invention permits the use of molecular design techniques to design, select and synthesize chemical entities and compounds, including inhibitory compounds, capable of binding to the active site or accessory binding site of a WW domain (e.g., a Pin1 WW domain), in whole or in part.

One approach enabled by this invention, is to use the structure coordinates set forth in Table 1 to design compounds that bind to the enzyme and alter the physical properties of the compounds in different ways, e.g., solubility. For example, this invention enables the design of compounds that act as competitive inhibitors of the WW domains by binding to, all or a portion of, the active site of a WW domain. This invention also enables the design of compounds that act as uncompetitive inhibitors of the WW domain (e.g., the WW domain of Pin1). These inhibitors may bind to, all or a portion of, the active site of a WW domain. Similarly, non-competitive inhibitors that bind to and inhibit a WW domain whether or not it is bound to another chemical entity may be designed using the structure coordinates of the invention as set forth in Table 1.

In another approach a Pin1 WW domain crystal is probed with molecules composed of a variety of different chemical entities to determine optimal sites for interaction between candidate binding molecules (e.g., inhibitors) and the WW domain active site.

In another embodiment, an approach made possible and enabled by this invention, is to screen computationally small molecule data bases for chemical entities or compounds that can bind in whole, or in part, to the WW domain. In this screening, the quality of fit of such entities or compounds to the binding site may be judged either by shape complementarity or by estimated interaction energy. Meng, E. C. et al., J. Comp. Chem., 13, pp. 505–524 (1992).

A number of WW domains exist, many of which have similar functional activity. However, many WW domains may crystallize in more than one crystal form. Thus, the structure coordinates of Pin1 WW domain, or portions thereof, as provided by this invention are particularly useful to solve the structure of other crystal forms of WW domains. They may also be used to solve the structure of a WW domain or Pin1 WW domain mutants, WW domain co-complexes, or the crystalline form of any other protein with significant amino acid sequence homology to any WW domain.

One method that may be employed for this purpose is molecular replacement. In this method, the unknown crystal structure, whether it is another WW domain crystal form, a WW domain or Pin1 WW domain mutant, or a WW domain co-complex, or the crystal of some other protein with significant amino acid sequence homology to any WW domain, may be determined using the structure coordinates as provided in Table 1. This method will provide an accurate structural form for the unknown crystal more quickly and efficiently than attempting to determine such information ab initio. Those of skill in the art understand that a set of structure coordinates determined by X-ray crystallography is not without standard error.

TABLE 1

| Atom | Atom Type | Residue | # | X | Y | Z | OCC | B |
|---|---|---|---|---|---|---|---|---|
| 1 | C | GLY | 1 | .297 | 6.261 | 77.129 | 1.00 | 34.99 |
| 2 | O | GLY | 1 | .701 | 5.443 | 77.948 | 1.00 | 35.67 |
| 3 | N | GLY | 1 | −1.549 | 6.552 | 75.579 | 1.00 | 35.60 |
| 4 | CA | GLY | 1 | −.294 | 5.819 | 75.824 | 1.00 | 35.38 |
| 5 | N | SER | 2 | .327 | 7.566 | 77.321 | 1.00 | 34.27 |
| 6 | CA | SER | 2 | .851 | 8.106 | 78.547 | 1.00 | 33.27 |

TABLE 1-continued

| Atom # | Atom Type | Residue | # | X | Y | Z | OCC | B |
|---|---|---|---|---|---|---|---|---|
| 7 | CB | SER | 2 | 1.393 | 9.518 | 78.304 | 1.00 | 33.43 |
| 8 | OG | SER | 2 | .397 | 10.429 | 77.856 | 1.00 | 34.33 |
| 9 | C | SER | 2 | −.346 | 8.118 | 79.496 | 1.00 | 32.42 |
| 10 | O | SER | 2 | −1.486 | 8.145 | 79.045 | 1.00 | 32.01 |
| 11 | N | HIS | 3 | −.093 | 8.099 | 80.798 | 1.00 | 31.53 |
| 12 | CA | HIS | 3 | −1.153 | 8.083 | 81.796 | 1.00 | 30.70 |
| 13 | CB | HIS | 3 | −.530 | 8.274 | 83.186 | 1.00 | 30.18 |
| 14 | CG | HIS | 3 | −1.523 | 8.316 | 84.304 | 1.00 | 29.99 |
| 15 | CD2 | HIS | 3 | −2.043 | 7.337 | 85.077 | 1.00 | 29.88 |
| 16 | ND1 | HIS | 3 | −2.102 | 9.493 | 84.732 | 1.00 | 29.83 |
| 17 | CE1 | HIS | 3 | −2.936 | 9.228 | 85.729 | 1.00 | 29.76 |
| 18 | NE2 | HIS | 3 | −2.915 | 7.930 | 85.954 | 1.00 | 29.65 |
| 19 | C | HIS | 3 | −2.261 | 9.111 | 81.546 | 1.00 | 30.30 |
| 20 | O | HIS | 3 | −3.428 | 8.818 | 81.767 | 1.00 | 30.00 |
| 21 | N | GLY | 4 | −1.899 | 10.292 | 81.053 | 1.00 | 30.06 |
| 22 | CA | GLY | 4 | −2.891 | 11.330 | 80.812 | 1.00 | 30.26 |
| 23 | C | GLY | 4 | −3.491 | 11.392 | 79.417 | 1.00 | 30.62 |
| 24 | O | GLY | 4 | −3.962 | 12.445 | 78.990 | 1.00 | 30.36 |
| 25 | N | MET | 5 | −3.484 | 10.272 | 78.702 | 1.00 | 31.06 |
| 26 | CA | MET | 5 | −4.029 | 10.239 | 77.349 | 1.00 | 32.14 |
| 27 | CB | MET | 5 | −2.900 | 10.330 | 76.320 | 1.00 | 33.56 |
| 28 | CG | MET | 5 | −1.877 | 11.379 | 76.665 | 1.00 | 35.79 |
| 29 | SD | MET | 5 | −1.479 | 12.502 | 75.352 | 1.00 | 39.48 |
| 30 | CE | MET | 5 | −2.891 | 13.512 | 75.389 | 1.00 | 38.05 |
| 31 | C | MET | 5 | −4.816 | 8.967 | 77.107 | 1.00 | 32.01 |
| 32 | O | MET | 5 | −4.592 | 7.954 | 77.770 | 1.00 | 31.57 |
| 33 | N | ALA | 6 | −5.743 | 9.024 | 76.156 | 1.00 | 32.09 |
| 34 | CA | ALA | 6 | −6.544 | 7.858 | 75.823 | 1.00 | 32.75 |
| 35 | CB | ALA | 6 | −7.620 | 8.224 | 74.808 | 1.00 | 32.26 |
| 36 | C | ALA | 6 | −5.593 | 6.840 | 75.226 | 1.00 | 33.51 |
| 37 | O | ALA | 6 | −4.579 | 7.208 | 74.625 | 1.00 | 32.76 |
| 38 | N | ASP | 7 | −5.900 | 5.561 | 75.408 | 1.00 | 34.83 |
| 39 | CA | ASP | 7 | −5.050 | 4.523 | 74.847 | 1.00 | 36.77 |
| 40 | CB | ASP | 7 | −5.191 | 3.201 | 75.574 | 1.00 | 36.60 |
| 41 | CG | ASP | 7 | −4.345 | 3.133 | 76.794 | 1.00 | 36.46 |
| 42 | OD1 | ASP | 7 | −3.300 | 3.815 | 76.824 | 1.00 | 36.44 |
| 43 | OD2 | ASP | 7 | −4.722 | 2.392 | 77.717 | 1.00 | 36.77 |
| 44 | C | ASP | 7 | −5.426 | 4.277 | 73.431 | 1.00 | 38.24 |
| 45 | O | ASP | 7 | −6.399 | 4.833 | 72.926 | 1.00 | 38.39 |
| 46 | N | GLU | 8 | −4.675 | 3.410 | 72.778 | 1.00 | 39.91 |
| 47 | CA | GLU | 8 | −5.037 | 3.176 | 71.420 | 1.00 | 41.61 |
| 48 | CB | GLU | 8 | −5.005 | 4.516 | 70.665 | 1.00 | 42.47 |
| 49 | CG | GLU | 8 | −3.630 | 5.196 | 70.661 | 1.00 | 43.94 |
| 50 | CD | GLU | 8 | −3.700 | 6.679 | 70.399 | 1.00 | 44.72 |
| 51 | OE1 | GLU | 8 | −3.249 | 7.133 | 69.317 | 1.00 | 45.25 |
| 52 | OE2 | GLU | 8 | −4.209 | 7.410 | 71.267 | 1.00 | 45.66 |
| 53 | C | GLU | 8 | −4.350 | 2.129 | 70.591 | 1.00 | 42.09 |
| 54 | O | GLU | 8 | −3.395 | 1.444 | 70.989 | 1.00 | 42.27 |
| 55 | N | GLU | 9 | −4.940 | 2.032 | 69.418 | 1.00 | 42.95 |
| 56 | CA | GLU | 9 | −4.606 | 1.219 | 68.258 | 1.00 | 43.60 |
| 57 | CB | GLU | 9 | −3.972 | 2.124 | 67.200 | 1.00 | 44.31 |
| 58 | CG | GLU | 9 | −3.671 | 3.542 | 67.569 | 1.00 | 45.81 |
| 59 | CD | GLU | 9 | −4.496 | 4.518 | 66.738 | 1.00 | 46.50 |
| 60 | OE1 | GLU | 9 | −5.535 | 4.977 | 67.255 | 1.00 | 47.27 |
| 61 | OE2 | GLU | 9 | −4.138 | 4.816 | 65.573 | 1.00 | 47.08 |
| 62 | C | GLU | 9 | −3.933 | −.102 | 68.005 | 1.00 | 43.44 |
| 63 | O | GLU | 9 | −3.420 | −.838 | 68.845 | 1.00 | 43.85 |
| 64 | N | LYS | 10 | −3.912 | −.276 | 66.690 | 1.00 | 43.38 |
| 65 | CA | LYS | 10 | −3.326 | −1.359 | 65.963 | 1.00 | 42.60 |
| 66 | CB | LYS | 10 | −4.363 | −2.078 | 65.091 | 1.00 | 43.20 |
| 67 | CG | LYS | 10 | −5.105 | −3.248 | 65.688 | 1.00 | 43.83 |
| 68 | CD | LYS | 10 | −6.580 | −2.891 | 65.718 | 1.00 | 44.18 |
| 69 | CE | LYS | 10 | −7.473 | −3.925 | 65.065 | 1.00 | 44.53 |
| 70 | NZ | LYS | 10 | −8.832 | −3.339 | 64.817 | 1.00 | 44.81 |
| 71 | C | LYS | 10 | −2.521 | −.539 | 64.995 | 1.00 | 41.77 |
| 72 | O | LYS | 10 | −1.396 | −.087 | 65.248 | 1.00 | 41.98 |
| 73 | N | LEU | 11 | −3.210 | −.290 | 63.894 | 1.00 | 40.35 |
| 74 | CA | LEU | 11 | −2.678 | .402 | 62.758 | 1.00 | 38.97 |
| 75 | CG | LEU | 11 | −2.843 | 2.889 | 63.092 | 1.00 | 38.96 |
| 76 | CD1 | LEU | 11 | −4.128 | 2.512 | 63.814 | 1.00 | 38.82 |
| 77 | CD2 | LEU | 11 | −2.222 | 4.141 | 63.685 | 1.00 | 38.60 |
| 78 | C | LEU | 11 | −1.778 | −.681 | 62.212 | 1.00 | 37.68 |
| 79 | O | LEU | 11 | −.725 | −.986 | 62.778 | 1.00 | 37.95 |
| 80 | CB | LEU | 11 | −1.911 | 1.672 | 63.158 | 1.00 | 38.94 |
| 81 | N | PRO | 12 | −2.216 | −1.315 | 61.126 | 1.00 | 36.04 |
| 82 | CD | PRO | 12 | −3.360 | −.954 | 60.273 | 1.00 | 35.90 |
| 83 | CA | PRO | 12 | −1.421 | −2.381 | 60.519 | 1.00 | 34.36 |
| 84 | CB | PRO | 12 | −2.183 | −2.692 | 59.236 | 1.00 | 34.88 |
| 85 | CG | PRO | 12 | −3.597 | −2.239 | 59.553 | 1.00 | 35.30 |
| 86 | C | PRO | 12 | −.049 | −1.801 | 60.240 | 1.00 | 32.67 |
| 87 | O | PRO | 12 | .151 | −.586 | 60.330 | 1.00 | 32.19 |
| 88 | N | PRO | 13 | .929 | −2.652 | 59.924 | 1.00 | 31.08 |
| 89 | CD | PRO | 13 | .963 | −4.125 | 59.872 | 1.00 | 30.89 |
| 90 | CA | PRO | 13 | 2.248 | −2.084 | 59.654 | 1.00 | 29.59 |
| 91 | CB | PRO | 13 | 3.042 | −3.293 | 59.165 | 1.00 | 30.16 |
| 92 | CG | PRO | 13 | 2.438 | −4.419 | 59.971 | 1.00 | 30.57 |
| 93 | C | PRO | 13 | 2.140 | −.985 | 58.593 | 1.00 | 28.22 |
| 94 | O | PRO | 13 | 1.302 | −1.062 | 57.689 | 1.00 | 27.79 |
| 95 | N | GLY | 14 | 2.966 | .047 | 58.737 | 1.00 | 26.74 |
| 96 | CA | GLY | 14 | 2.970 | 1.140 | 57.783 | 1.00 | 25.25 |
| 97 | C | GLY | 14 | 2.066 | 2.317 | 58.092 | 1.00 | 24.24 |
| 98 | O | GLY | 14 | 2.264 | 3.403 | 57.553 | 1.00 | 23.92 |
| 99 | N | TRP | 15 | 1.081 | 2.124 | 58.960 | 1.00 | 23.51 |
| 100 | CA | TRP | 15 | .160 | 3.205 | 59.286 | 1.00 | 22.91 |
| 101 | CB | TRP | 15 | −1.275 | 2.679 | 59.368 | 1.00 | 22.23 |
| 102 | CG | TRP | 15 | −1.845 | 2.209 | 58.065 | 1.00 | 21.67 |
| 103 | CD2 | TRP | 15 | −2.524 | 3.010 | 57.092 | 1.00 | 21.24 |
| 104 | CE2 | TRP | 15 | −2.898 | 2.152 | 56.032 | 1.00 | 21.30 |
| 105 | CE3 | TRP | 15 | −2.853 | 4.371 | 57.011 | 1.00 | 20.98 |
| 106 | CD1 | TRP | 15 | −1.832 | .935 | 57.573 | 1.00 | 21.71 |
| 107 | NE1 | TRP | 15 | −2.462 | .893 | 56.352 | 1.00 | 21.40 |
| 108 | CZ2 | TRP | 15 | −3.588 | 2.609 | 54.902 | 1.00 | 21.06 |
| 109 | CZ3 | TRP | 15 | −3.540 | 4.829 | 55.884 | 1.00 | 21.18 |
| 110 | CH2 | TRP | 15 | −3.898 | 3.946 | 54.845 | 1.00 | 21.04 |
| 111 | C | TRP | 15 | .470 | 3.954 | 60.575 | 1.00 | 23.13 |
| 112 | O | TRP | 15 | 1.032 | 3.402 | 61.519 | 1.00 | 22.54 |
| 113 | N | GLU | 16 | .085 | 5.223 | 60.596 | 1.00 | 23.37 |
| 114 | CA | GLU | 16 | .267 | 6.065 | 61.763 | 1.00 | 24.62 |
| 115 | CB | GLU | 16 | 1.619 | 6.790 | 61.698 | 1.00 | 24.57 |
| 116 | CG | GLU | 16 | 1.788 | 7.743 | 60.532 | 1.00 | 24.62 |
| 117 | CD | GLU | 16 | 3.200 | 8.311 | 60.448 | 1.00 | 24.61 |
| 118 | OE1 | GLU | 16 | 4.114 | 7.598 | 59.988 | 1.00 | 24.24 |
| 119 | OE2 | GLU | 16 | 3.395 | 9.470 | 60.857 | 1.00 | 24.99 |
| 120 | C | GLU | 16 | −.890 | 7.063 | 61.812 | 1.00 | 25.27 |
| 121 | O | GLU | 16 | −1.487 | 7.384 | 60.784 | 1.00 | 24.68 |
| 122 | N | LYS | 17 | −1.224 | 7.526 | 63.012 | 1.00 | 26.55 |
| 123 | CA | LYS | 17 | −2.307 | 8.486 | 63.173 | 1.00 | 28.35 |
| 124 | CB | LYS | 17 | −3.042 | 8.285 | 64.502 | 1.00 | 29.42 |
| 125 | CG | LYS | 17 | −4.042 | 9.410 | 64.769 | 1.00 | 31.85 |
| 126 | CD | LYS | 17 | −4.548 | 9.476 | 66.204 | 1.00 | 33.36 |
| 127 | CE | LYS | 17 | −5.308 | 8.228 | 66.599 | 1.00 | 34.45 |
| 128 | NZ | LYS | 17 | −4.377 | 7.166 | 67.041 | 1.00 | 36.19 |
| 129 | C | LYS | 17 | −1.781 | 9.910 | 63.142 | 1.00 | 29.19 |
| 130 | O | LYS | 17 | −.680 | 10.188 | 63.617 | 1.00 | 28.99 |
| 131 | N | ARG | 18 | −2.577 | 10.818 | 62.593 | 1.00 | 30.37 |
| 132 | CA | ARG | 18 | −2.184 | 12.215 | 62.536 | 1.00 | 31.87 |
| 133 | CB | ARG | 18 | −1.435 | 12.482 | 61.233 | 1.00 | 32.64 |
| 134 | CG | ARG | 18 | −.238 | 11.563 | 61.069 | 1.00 | 34.24 |
| 135 | CD | ARG | 18 | .498 | 11.835 | 59.791 | 1.00 | 35.78 |
| 136 | NE | ARG | 18 | 1.196 | 13.109 | 59.859 | 1.00 | 37.48 |
| 137 | CZ | ARG | 18 | 2.517 | 13.230 | 59.884 | 1.00 | 37.91 |
| 138 | NH1 | ARG | 18 | 3.066 | 14.428 | 59.952 | 1.00 | 38.43 |
| 139 | NH2 | ARG | 18 | 3.291 | 12.154 | 59.830 | 1.00 | 38.32 |
| 140 | C | ARG | 18 | −3.394 | 13.127 | 62.672 | 1.00 | 32.46 |
| 141 | O | ARG | 18 | −4.531 | 12.658 | 62.697 | 1.00 | 32.20 |
| 142 | N | MET | 19 | −3.146 | 14.428 | 62.777 | 1.00 | 33.73 |
| 143 | CA | MET | 19 | −4.224 | 15.396 | 62.922 | 1.00 | 35.12 |
| 144 | CB | MET | 19 | −4.089 | 16.168 | 64.236 | 1.00 | 36.75 |
| 145 | CG | MET | 19 | −4.642 | 15.457 | 65.452 | 1.00 | 39.07 |
| 146 | SD | MET | 19 | −5.206 | 16.611 | 66.735 | 1.00 | 41.46 |
| 147 | CE | MET | 19 | −5.153 | 18.203 | 65.865 | 1.00 | 41.00 |
| 148 | C | MET | 19 | −4.293 | 16.405 | 61.790 | 1.00 | 35.20 |
| 149 | O | MET | 19 | −3.269 | 16.886 | 61.306 | 1.00 | 35.22 |
| 150 | N | SER | 20 | −5.514 | 16.727 | 61.381 | 1.00 | 35.36 |
| 151 | CA | SER | 20 | −5.740 | 17.705 | 60.328 | 1.00 | 35.66 |
| 152 | CB | SER | 20 | −7.184 | 17.609 | 59.825 | 1.00 | 35.65 |
| 153 | OG | SER | 20 | −7.675 | 18.875 | 59.414 | 1.00 | 35.43 |
| 154 | C | SER | 20 | −5.480 | 19.098 | 60.891 | 1.00 | 36.12 |
| 155 | O | SER | 20 | −6.091 | 19.496 | 61.883 | 1.00 | 35.85 |
| 156 | N | ARG | 21 | −4.557 | 19.828 | 60.272 | 1.00 | 36.76 |
| 157 | CA | ARG | 21 | −4.238 | 21.186 | 60.711 | 1.00 | 37.41 |
| 158 | CB | ARG | 21 | −3.125 | 21.796 | 59.844 | 1.00 | 38.05 |

TABLE 1-continued

| Atom | Atom Type | Residue | # | X | Y | Z | OCC | B |
|---|---|---|---|---|---|---|---|---|
| 159 | CG | ARG | 21 | −1.694 | 21.415 | 60.217 | 1.00 | 39.57 |
| 160 | CD | ARG | 21 | −1.064 | 20.438 | 59.224 | 1.00 | 41.03 |
| 161 | NE | ARG | 21 | −1.805 | 20.360 | 57.971 | 1.00 | 42.01 |
| 162 | CZ | ARG | 21 | −1.230 | 20.319 | 56.770 | 1.00 | 42.70 |
| 163 | NH1 | ARG | 21 | .094 | 20.355 | 56.660 | 1.00 | 43.34 |
| 164 | NH2 | ARG | 21 | −1.972 | 20.225 | 55.672 | 1.00 | 43.27 |
| 165 | C | ARG | 21 | −5.488 | 22.053 | 60.579 | 1.00 | 37.21 |
| 166 | O | ARG | 21 | −5.701 | 22.983 | 61.354 | 1.00 | 37.49 |
| 167 | N | SER | 22 | −6.311 | 21.729 | 59.589 | 1.00 | 36.91 |
| 168 | CA | SER | 22 | −7.527 | 22.473 | 59.303 | 1.00 | 36.54 |
| 169 | CB | SER | 22 | −7.950 | 22.201 | 57.856 | 1.00 | 37.25 |
| 170 | OG | SER | 22 | −9.308 | 22.541 | 57.643 | 1.00 | 37.97 |
| 171 | C | SER | 22 | −8.726 | 22.265 | 60.227 | 1.00 | 35.96 |
| 172 | O | SER | 22 | −9.326 | 23.235 | 60.690 | 1.00 | 36.13 |
| 173 | N | SER | 23 | −9.076 | 21.012 | 60.496 | 1.00 | 34.79 |
| 174 | CA | SER | 23 | −10.240 | 20.720 | 61.330 | 1.00 | 33.65 |
| 175 | CB | SER | 23 | −11.163 | 19.756 | 60.584 | 1.00 | 33.79 |
| 176 | OG | SER | 23 | −10.514 | 18.517 | 60.357 | 1.00 | 34.00 |
| 177 | C | SER | 23 | −9.957 | 20.148 | 62.715 | 1.00 | 32.65 |
| 178 | O | SER | 23 | −10.855 | 20.100 | 63.558 | 1.00 | 32.30 |
| 179 | N | GLY | 24 | −8.723 | 19.716 | 62.951 | 1.00 | 31.54 |
| 180 | CA | GLY | 24 | −8.383 | 19.130 | 64.236 | 1.00 | 30.56 |
| 181 | C | CLY | 24 | −8.857 | 17.686 | 64.277 | 1.00 | 29.75 |
| 182 | O | GLY | 24 | −8.703 | 16.981 | 65.276 | 1.00 | 29.78 |
| 183 | N | ARG | 25 | −9.445 | 17.251 | 63.169 | 1.00 | 28.87 |
| 184 | CA | ARG | 25 | −9.963 | 15.896 | 63.019 | 1.00 | 28.00 |
| 185 | CB | ARG | 25 | −10.936 | 15.884 | 61.838 | 1.00 | 29.15 |
| 186 | CG | ARG | 25 | −11.631 | 14.576 | 61.522 | 1.00 | 30.49 |
| 187 | CD | ARG | 25 | −12.548 | 14.810 | 60.330 | 1.00 | 31.64 |
| 188 | NE | ARG | 25 | −13.153 | 13.592 | 59.806 | 1.00 | 32.91 |
| 189 | CZ | ARG | 25 | −13.796 | 13.531 | 58.645 | 1.00 | 32.93 |
| 190 | NH1 | ARG | 25 | −13.913 | 14.617 | 57.892 | 1.00 | 33.35 |
| 191 | NH2 | ARG | 25 | −14.316 | 12.384 | 58.232 | 1.00 | 33.50 |
| 192 | C | ARG | 25 | −8.806 | 14.916 | 62.783 | 1.00 | 27.17 |
| 193 | O | ARG | 25 | −7.846 | 15.235 | 62.081 | 1.00 | 26.80 |
| 194 | N | VAL | 26 | −8.894 | 13.732 | 63.380 | 1.00 | 25.90 |
| 195 | CA | VAL | 26 | −7.851 | 12.717 | 63.223 | 1.00 | 25.40 |
| 196 | CB | VAL | 26 | −7.943 | 11.047 | 64.341 | 1.00 | 25.46 |
| 197 | CG1 | VAL | 26 | −7.058 | 10.451 | 64.006 | 1.00 | 25.92 |
| 198 | CG2 | VAL | 26 | −7.524 | 12.233 | 65.675 | 1.00 | 25.82 |
| 199 | C | VAL | 26 | −7.960 | 12.007 | 61.877 | 1.00 | 24.87 |
| 200 | O | VAL | 26 | −9.054 | 11.824 | 61.353 | 1.00 | 25.20 |
| 201 | N | TYR | 27 | −6.819 | 11.621 | 61.313 | 1.00 | 24.40 |
| 202 | CA | TYR | 27 | −6.803 | 10.886 | 60.051 | 1.00 | 23.42 |
| 203 | CG | TYR | 27 | −5.442 | 12.563 | 58.582 | 1.00 | 24.14 |
| 204 | CD1 | TYR | 27 | −4.434 | 11.985 | 57.803 | 1.00 | 24.61 |
| 205 | CE1 | TYR | 27 | −3.266 | 12.688 | 57.496 | 1.00 | 24.81 |
| 206 | CD2 | TYR | 27 | −5.245 | 13.858 | 59.055 | 1.00 | 24.39 |
| 207 | CE2 | TYR | 27 | −4.084 | 14.567 | 58.758 | 1.00 | 25.05 |
| 208 | CZ | TYR | 27 | −3.100 | 13.981 | 57.978 | 1.00 | 25.21 |
| 209 | OH | TYR | 27 | −1.962 | 14.698 | 57.683 | 1.00 | 25.76 |
| 210 | C | TYR | 27 | −5.624 | 9.925 | 60.069 | 1.00 | 23.02 |
| 211 | O | TYR | 27 | −4.774 | 9.999 | 60.960 | 1.00 | 22.89 |
| 212 | CB | TYR | 27 | −6.746 | 11.836 | 58.839 | 1.00 | 23.85 |
| 213 | N | TYR | 28 | −5.575 | 9.014 | 59.103 | 1.00 | 21.88 |
| 214 | CA | TYR | 28 | −4.504 | 8.034 | 59.074 | 1.00 | 21.16 |
| 215 | CB | TYR | 28 | −5.095 | 6.632 | 59.223 | 1.00 | 22.27 |
| 216 | CG | TYR | 28 | −5.914 | 6.520 | 60.488 | 1.00 | 23.24 |
| 217 | CD1 | TYR | 28 | −7.210 | 7.032 | 60.550 | 1.00 | 24.01 |
| 218 | CE1 | TYR | 28 | −7.926 | 7.036 | 61.745 | 1.00 | 24.83 |
| 219 | CD2 | TYR | 28 | −5.358 | 5.997 | 61.652 | 1.00 | 23.92 |
| 220 | CE2 | TYR | 28 | −6.062 | 5.996 | 62.852 | 1.00 | 24.76 |
| 221 | CZ | TYR | 28 | −7.343 | 6.519 | 62.891 | 1.00 | 25.17 |
| 222 | OH | TYR | 28 | −8.019 | 6.553 | 64.087 | 1.00 | 26.30 |
| 223 | C | TYR | 28 | −3.632 | 8.138 | 57.837 | 1.00 | 20.21 |
| 224 | O | TYR | 28 | −4.118 | 8.323 | 56.725 | 1.00 | 19.01 |
| 225 | N | PHE | 29 | −2.332 | 8.017 | 58.065 | 1.00 | 19.58 |
| 226 | CA | PHE | 29 | −1.327 | 8.134 | 57.024 | 1.00 | 18.83 |
| 227 | CB | PHE | 29 | −.461 | 9.359 | 57.344 | 1.00 | 19.22 |
| 228 | CG | PHE | 29 | .776 | 9.488 | 56.506 | 1.00 | 19.30 |
| 229 | CD1 | PHE | 29 | .691 | 9.778 | 55.149 | 1.00 | 19.41 |
| 230 | CD2 | PHE | 29 | 2.034 | 9.366 | 57.089 | 1.00 | 19.57 |
| 231 | CE1 | PHE | 29 | 1.843 | 9.952 | 54.386 | 1.00 | 19.63 |
| 232 | CE2 | PHE | 29 | 3.191 | 9.538 | 56.337 | 1.00 | 19.77 |
| 233 | CZ | PHE | 29 | 3.098 | 9.831 | 54.984 | 1.00 | 19.44 |
| 234 | C | PHE | 29 | −.468 | 6.878 | 56.936 | 1.00 | 18.34 |
| 235 | O | PHE | 29 | −.029 | 6.337 | 57.951 | 1.00 | 18.15 |
| 236 | N | ASN | 30 | −.241 | 6.407 | 55.716 | 1.00 | 17.82 |
| 237 | CA | ASN | 30 | .595 | 5.232 | 55.513 | 1.00 | 17.50 |
| 238 | CB | ASN | 30 | −.032 | 4.307 | 54.464 | 1.00 | 17.63 |
| 239 | CG | ASN | 30 | .741 | 3.019 | 54.287 | 1.00 | 17.60 |
| 240 | OD1 | ASN | 30 | 1.913 | 3.032 | 53.908 | 1.00 | 17.34 |
| 241 | ND2 | ASN | 30 | .088 | 1.893 | 54.563 | 1.00 | 18.35 |
| 242 | C | ASN | 30 | 1.928 | 5.781 | 55.017 | 1.00 | 17.59 |
| 243 | O | ASN | 30 | 1.975 | 6.414 | 53.963 | 1.00 | 16.77 |
| 244 | N | HIS | 31 | 3.003 | 5.557 | 55.774 | 1.00 | 17.16 |
| 245 | CA | HIS | 31 | 4.306 | 6.075 | 55.377 | 1.00 | 17.86 |
| 246 | CB | HIS | 31 | 5.202 | 6.312 | 56.607 | 1.00 | 18.00 |
| 247 | CG | HIS | 31 | 5.404 | 5.105 | 57.470 | 1.00 | 18.54 |
| 248 | CD2 | HIS | 31 | 6.042 | 3.934 | 57.234 | 1.00 | 18.99 |
| 249 | ND1 | HIS | 31 | 4.955 | 5.041 | 58.772 | 1.00 | 18.72 |
| 250 | CE1 | HIS | 31 | 5.310 | 3.883 | 59.301 | 1.00 | 19.47 |
| 251 | NE2 | HIS | 31 | 5.971 | 3.193 | 58.388 | 1.00 | 18.96 |
| 252 | C | HIS | 31 | 5.052 | 5.259 | 54.328 | 1.00 | 17.93 |
| 253 | O | HIS | 31 | 6.205 | 5.554 | 54.019 | 1.00 | 18.12 |
| 254 | N | ILE | 32 | 4.396 | 4.243 | 53.773 | 1.00 | 17.83 |
| 255 | CA | ILE | 32 | 5.006 | 3.425 | 52.729 | 1.00 | 17.67 |
| 256 | CB | ILE | 32 | 4.772 | 1.909 | 52.968 | 1.00 | 18.12 |
| 257 | CG2 | ILE | 32 | 5.434 | 1.097 | 51.854 | 1.00 | 17.77 |
| 258 | CG1 | ILE | 32 | 5.357 | 1.492 | 54.321 | 1.00 | 18.34 |
| 259 | CD1 | ILE | 32 | 5.138 | .027 | 54.656 | 1.00 | 19.67 |
| 260 | C | ILE | 32 | 4.382 | 3.823 | 51.387 | 1.00 | 17.44 |
| 261 | O | ILE | 32 | 5.078 | 3.950 | 50.379 | 1.00 | 17.36 |
| 262 | N | THR | 33 | 3.067 | 4.035 | 51.385 | 1.00 | 17.20 |
| 263 | CA | THR | 33 | 2.348 | 4.425 | 50.170 | 1.00 | 17.33 |
| 264 | CB | THR | 33 | .955 | 3.775 | 50.109 | 1.00 | 17.42 |
| 265 | OG1 | THR | 33 | .134 | 4.338 | 51.141 | 1.00 | 17.75 |
| 266 | CG2 | THR | 33 | 1.050 | 2.271 | 50.319 | 1.00 | 18.24 |
| 267 | C | THR | 33 | 2.131 | 5.939 | 50.135 | 1.00 | 17.18 |
| 268 | O | THR | 33 | 1.838 | 6.512 | 49.085 | 1.00 | 16.30 |
| 269 | N | ASN | 34 | 2.270 | 6.568 | 51.299 | 1.00 | 17.25 |
| 270 | CA | ASN | 34 | 2.075 | 8.002 | 51.467 | 1.00 | 17.74 |
| 271 | CB | ASN | 34 | 3.024 | 8.795 | 50.559 | 1.00 | 18.75 |
| 272 | CG | ASN | 34 | 4.464 | 8.737 | 51.047 | 1.00 | 20.18 |
| 273 | OD1 | ASN | 34 | 4.712 | 8.518 | 52.236 | 1.00 | 21.35 |
| 274 | ND2 | ASN | 34 | 5.416 | 8.947 | 50.144 | 1.00 | 20.59 |
| 275 | C | ASN | 34 | .629 | 8.443 | 51.262 | 1.00 | 17.42 |
| 276 | O | ASN | 34 | .347 | 9.621 | 51.034 | 1.00 | 17.41 |
| 277 | N | ALA | 35 | −.291 | 7.491 | 51.371 | 1.00 | 17.84 |
| 278 | CA | ALA | 35 | −1.711 | 7.792 | 51.224 | 1.00 | 18.28 |
| 279 | CB | ALA | 35 | −2.458 | 6.563 | 50.741 | 1.00 | 18.12 |
| 280 | C | ALA | 35 | −2.300 | 8.262 | 52.553 | 1.00 | 19.15 |
| 281 | O | ALA | 35 | −1.847 | 7.848 | 53.620 | 1.00 | 18.60 |
| 282 | N | SER | 36 | −3.309 | 9.129 | 52.472 | 1.00 | 19.81 |
| 283 | CA | SER | 36 | −3.999 | 9.651 | 53.650 | 1.00 | 21.25 |
| 284 | CB | SER | 36 | −3.828 | 11.172 | 53.752 | 1.00 | 21.07 |
| 285 | OG | SER | 36 | −2.486 | 11.530 | 54.036 | 1.00 | 22.28 |
| 286 | C | SER | 36 | −5.487 | 9.325 | 53.541 | 1.00 | 22.07 |
| 287 | O | SER | 36 | −6.075 | 9.447 | 52.469 | 1.00 | 21.66 |
| 288 | N | GLN | 37 | −6.091 | 8.910 | 54.650 | 1.00 | 23.28 |
| 289 | CA | GLN | 37 | −7.516 | 8.586 | 54.669 | 1.00 | 24.65 |
| 290 | CB | GLN | 37 | −7.739 | 7.112 | 54.317 | 1.00 | 24.61 |
| 291 | CG | GLN | 37 | −7.084 | 6.119 | 55.269 | 1.00 | 24.96 |
| 292 | CD | GLN | 37 | −7.343 | 4.676 | 54.868 | 1.00 | 25.43 |
| 293 | OE1 | GLN | 37 | −7.116 | 4.289 | 53.724 | 1.00 | 25.92 |
| 294 | NE2 | GLN | 37 | −7.814 | 3.872 | 55.814 | 1.00 | 26.05 |
| 295 | C | GLN | 37 | −8.104 | 8.881 | 56.047 | 1.00 | 25.98 |
| 296 | O | GLN | 37 | −7.414 | 8.775 | 57.058 | 1.00 | 25.84 |
| 297 | N | TRP | 38 | −9.381 | 9.252 | 56.076 | 1.00 | 27.72 |
| 298 | CA | TRP | 38 | −10.074 | 9.568 | 57.322 | 1.00 | 29.72 |
| 299 | CB | TRP | 38 | −11.405 | 10.268 | 57.024 | 1.00 | 29.29 |
| 300 | CG | TRP | 38 | −11.277 | 11.647 | 56.461 | 1.00 | 29.14 |
| 301 | CD2 | TRP | 38 | −10.665 | 12.776 | 57.092 | 1.00 | 28.85 |
| 302 | CE2 | TRP | 38 | −10.802 | 13.872 | 56.209 | 1.00 | 28.94 |
| 303 | CE3 | TRP | 38 | −10.012 | 12.977 | 58.316 | 1.00 | 29.21 |
| 304 | CD1 | TRP | 38 | −11.745 | 12.085 | 55.257 | 1.00 | 29.21 |
| 305 | NE1 | TRP | 38 | −11.466 | 13.421 | 55.097 | 1.00 | 29.11 |
| 306 | CZ2 | TRP | 38 | −10.310 | 15.145 | 56.509 | 1.00 | 28.81 |
| 307 | CZ3 | TRP | 38 | −9.521 | 14.244 | 58.618 | 1.00 | 28.69 |
| 308 | CH2 | TRP | 38 | −9.675 | 15.312 | 57.715 | 1.00 | 28.99 |
| 309 | C | TRP | 38 | −10.362 | 8.336 | 58.173 | 1.00 | 31.49 |
| 310 | O | TRP | 38 | −10.200 | 8.354 | 59.392 | 1.00 | 31.14 |

TABLE 1-continued

| Atom | Atom Type | Residue | # | X | Y | Z | OCC | B |
|---|---|---|---|---|---|---|---|---|
| 311 | N | GLU | 39 | −10.801 | 7.270 | 57.518 | 1.00 | 33.88 |
| 312 | CA | GLU | 39 | −11.150 | 6.033 | 58.195 | 1.00 | 36.66 |
| 313 | CB | GLU | 39 | −11.931 | 5.142 | 57.226 | 1.00 | 37.87 |
| 314 | CG | GLU | 39 | −11.732 | 3.645 | 57.392 | 1.00 | 40.11 |
| 315 | CD | GLU | 39 | −10.922 | 3.045 | 56.255 | 1.00 | 41.50 |
| 316 | OE1 | GLU | 39 | −10.937 | 1.802 | 56.096 | 1.00 | 42.21 |
| 317 | OE2 | GLU | 39 | −10.267 | 3.818 | 55.521 | 1.00 | 42.41 |
| 318 | C | GLU | 39 | −9.960 | 5.283 | 58.764 | 1.00 | 37.86 |
| 319 | O | GLU | 39 | −8.928 | 5.133 | 58.104 | 1.00 | 37.68 |
| 320 | N | ARG | 40 | −10.097 | 4.821 | 60.002 | 1.00 | 39.22 |
| 321 | CA | ARG | 40 | −9.016 | 4.066 | 60.600 | 1.00 | 41.26 |
| 322 | CB | ARG | 40 | −9.346 | 3.634 | 62.027 | 1.00 | 41.97 |
| 323 | CG | ARG | 40 | −8.215 | 2.858 | 62.681 | 1.00 | 43.45 |
| 324 | CD | ARG | 40 | −8.414 | 2.794 | 64.176 | 1.00 | 44.68 |
| 325 | NE | ARG | 40 | −9.631 | 2.070 | 64.530 | 1.00 | 46.28 |
| 326 | CZ | ARG | 40 | −10.399 | 2.374 | 65.571 | 1.00 | 47.26 |
| 327 | NH1 | ARG | 40 | −10.079 | 3.399 | 66.349 | 1.00 | 47.90 |
| 328 | NH2 | ARG | 40 | −11.465 | 1.635 | 65.863 | 1.00 | 47.94 |
| 329 | C | ARG | 40 | −8.889 | 2.847 | 59.709 | 1.00 | 42.22 |
| 330 | O | ARG | 40 | −9.829 | 2.067 | 59.568 | 1.00 | 42.01 |
| 331 | N | PRO | 41 | −7.728 | 2.679 | 59.073 | 1.00 | 43.30 |
| 332 | CD | PRO | 41 | −6.426 | 3.285 | 59.408 | 1.00 | 43.24 |
| 333 | CA | PRO | 41 | −7.557 | 1.519 | 58.200 | 1.00 | 44.44 |
| 334 | CB | PRO | 41 | −6.118 | 1.664 | 57.735 | 1.00 | 43.99 |
| 335 | CG | PRO | 41 | −5.452 | 2.215 | 58.973 | 1.00 | 43.52 |
| 336 | C | PRO | 41 | −7.747 | .295 | 59.076 | 1.00 | 45.67 |
| 337 | O | PRO | 41 | −8.151 | −.769 | 58.614 | 1.00 | 45.96 |
| 338 | N | SER | 42 | −7.472 | .509 | 60.359 | 1.00 | 47.15 |
| 339 | CA | SER | 42 | −7.526 | −.488 | 61.419 | 1.00 | 48.41 |
| 340 | CB | SER | 42 | −8.015 | −1.848 | 60.914 | 1.00 | 48.76 |
| 341 | OG | SER | 42 | −7.942 | −2.822 | 61.941 | 1.00 | 49.21 |
| 342 | C | SER | 42 | −6.080 | −.596 | 61.874 | 1.00 | 48.94 |
| 343 | O | SER | 42 | −5.460 | .476 | 62.034 | 1.00 | 49.50 |
| 344 | OT | SER | 42 | −5.583 | −1.728 | 62.054 | 1.00 | 49.73 |
| 345 | CB | GLU | 55 | 3.104 | −8.396 | 51.102 | 1.00 | 46.42 |
| 346 | CG | GLU | 55 | 4.292 | −9.110 | 50.504 | 1.00 | 47.06 |
| 347 | CD | GLU | 55 | 5.366 | −8.171 | 50.026 | 1.00 | 47.19 |
| 348 | OE1 | GLU | 55 | 6.311 | −8.655 | 49.370 | 1.00 | 47.56 |
| 349 | OE2 | GLU | 55 | 5.270 | −6.959 | 50.306 | 1.00 | 47.58 |
| 350 | C | GLU | 55 | 1.824 | −10.384 | 50.300 | 1.00 | 45.13 |
| 351 | O | GLU | 55 | 2.186 | −11.549 | 50.483 | 1.00 | 45.49 |
| 352 | N | GLU | 55 | 2.230 | −10.050 | 52.720 | 1.00 | 46.15 |
| 353 | CA | GLU | 55 | 1.954 | −9.349 | 51.424 | 1.00 | 45.81 |
| 354 | N | PRO | 56 | 1.293 | −9.977 | 49.133 | 1.00 | 44.26 |
| 355 | CD | PRO | 56 | .521 | −8.734 | 48.948 | 1.00 | 44.19 |
| 356 | CA | PRO | 56 | 1.121 | −10.878 | 47.985 | 1.00 | 43.03 |
| 357 | CB | PRO | 56 | −.036 | −10.239 | 47.221 | 1.00 | 43.46 |
| 358 | CG | PRO | 56 | .152 | −8.781 | 47.476 | 1.00 | 44.13 |
| 359 | C | PRO | 56 | 2.383 | −11.033 | 47.128 | 1.00 | 41.84 |
| 360 | O | PRO | 56 | 3.294 | −10.210 | 47.218 | 1.00 | 41.90 |
| 361 | N | ALA | 57 | 2.432 | −12.076 | 46.295 | 1.00 | 40.21 |
| 362 | CA | ALA | 57 | 3.609 | −12.319 | 45.462 | 1.00 | 38.35 |
| 363 | CB | ALA | 57 | 3.696 | −13.780 | 45.098 | 1.00 | 38.82 |
| 364 | C | ALA | 57 | 3.717 | −11.470 | 44.202 | 1.00 | 36.94 |
| 365 | O | ALA | 57 | 4.824 | −11.120 | 43.791 | 1.00 | 36.85 |
| 366 | N | ARG | 58 | 2.590 | −11.163 | 43.568 | 1.00 | 34.78 |
| 367 | CA | ARG | 58 | 2.612 | −10.324 | 42.363 | 1.00 | 32.26 |
| 368 | CB | ARG | 58 | 2.433 | −11.170 | 41.088 | 1.00 | 33.84 |
| 369 | CG | ARG | 58 | .964 | −11.340 | 40.690 | 1.00 | 35.66 |
| 370 | CD | ARG | 58 | .702 | −12.385 | 39.614 | 1.00 | 37.32 |
| 371 | NE | ARG | 58 | 1.340 | −12.096 | 38.335 | 1.00 | 38.74 |
| 372 | CZ | ARG | 58 | .736 | −12.218 | 37.156 | 1.00 | 39.29 |
| 373 | NE1 | ARG | 58 | −.530 | −12.610 | 37.085 | 1.00 | 40.23 |
| 374 | NH2 | ARG | 58 | 1.412 | −11.984 | 36.045 | 1.00 | 39.66 |
| 375 | C | ARG | 58 | 1.473 | −9.306 | 42.441 | 1.00 | 29.53 |
| 376 | O | ARG | 58 | .411 | −9.579 | 43.005 | 1.00 | 29.35 |
| 377 | N | VAL | 59 | 1.712 | −8.120 | 41.904 | 1.00 | 26.26 |
| 378 | CA | VAL | 59 | .684 | −7.095 | 41.881 | 1.00 | 23.07 |
| 379 | CB | VAL | 59 | .893 | −6.012 | 42.976 | 1.00 | 22.71 |
| 380 | CG1 | VAL | 59 | .819 | −6.639 | 44.359 | 1.00 | 22.02 |
| 381 | CG2 | VAL | 59 | 2.230 | −5.310 | 42.773 | 1.00 | 21.89 |
| 382 | C | VAL | 59 | .724 | −6.417 | 40.518 | 1.00 | 21.53 |
| 383 | O | VAL | 59 | 1.769 | −6.389 | 39.867 | 1.00 | 21.30 |
| 384 | N | ARG | 60 | −.416 | −5.912 | 40.062 | 1.00 | 19.57 |
| 385 | CA | ARG | 60 | −.450 | −5.188 | 38.796 | 1.00 | 18.00 |
| 386 | CB | ARG | 60 | −1.483 | −5.779 | 37.823 | 1.00 | 18.09 |
| 387 | CG | ARG | 60 | −1.471 | −5.086 | 36.447 | 1.00 | 17.67 |
| 388 | CD | ARG | 60 | −2.256 | −5.867 | 35.402 | 1.00 | 18.99 |
| 389 | NE | ARG | 60 | −2.107 | −5.292 | 34.067 | 1.00 | 18.15 |
| 390 | CZ | ARG | 60 | −2.522 | −5.880 | 32.949 | 1.00 | 19.10 |
| 391 | NH1 | ARG | 60 | −3.115 | −7.068 | 33.004 | 1.00 | 19.83 |
| 392 | NH2 | ARG | 60 | −2.345 | −5.286 | 31.776 | 1.00 | 18.46 |
| 393 | C | ARG | 60 | −.820 | −3.749 | 39.146 | 1.00 | 17.26 |
| 394 | O | ARG | 60 | −1.755 | −3.515 | 39.911 | 1.00 | 16.91 |
| 395 | N | CYS | 61 | −.077 | −2.791 | 38.599 | 1.00 | 16.03 |
| 396 | CA | CYS | 61 | −.332 | −1.383 | 38.885 | 1.00 | 15.56 |
| 397 | CB | CYS | 61 | .703 | −.832 | 39.874 | 1.00 | 15.78 |
| 398 | SG | CYS | 61 | .737 | −1.592 | 41.504 | 1.00 | 16.00 |
| 399 | C | CYS | 61 | −.283 | −.503 | 37.653 | 1.00 | 15.27 |
| 400 | O | CYS | 61 | .294 | −.866 | 36.626 | 1.00 | 15.20 |
| 401 | N | SER | 62 | −.912 | .659 | 37.783 | 1.00 | 14.94 |
| 402 | CA | SER | 62 | −.921 | 1.687 | 36.758 | 1.00 | 14.50 |
| 403 | CB | SER | 62 | −2.350 | 2.013 | 36.295 | 1.00 | 14.59 |
| 404 | OG | SER | 62 | −2.926 | .951 | 35.554 | 1.00 | 15.92 |
| 405 | C | SER | 62 | −.357 | 2.876 | 37.528 | 1.00 | 14.32 |
| 406 | O | SER | 62 | −.457 | 2.918 | 38.756 | 1.00 | 14.45 |
| 407 | N | HIS | 63 | .255 | 3.828 | 36.837 | 1.00 | 14.07 |
| 408 | CA | HIS | 63 | .775 | 4.997 | 37.534 | 1.00 | 13.79 |
| 409 | CB | HIS | 63 | 2.214 | 4.767 | 38.050 | 1.00 | 13.87 |
| 410 | CG | HIS | 63 | 3.268 | 4.841 | 36.986 | 1.00 | 12.81 |
| 411 | CD2 | HIS | 63 | 3.254 | 4.470 | 35.683 | 1.00 | 12.77 |
| 412 | ND1 | HIS | 63 | 4.535 | 5.332 | 37.229 | 1.00 | 12.86 |
| 413 | CE1 | HIS | 63 | 5.253 | 5.261 | 36.121 | 1.00 | 12.48 |
| 414 | NE2 | HIS | 63 | 4.498 | 4.741 | 35.169 | 1.00 | 12.51 |
| 415 | C | HIS | 63 | .755 | 6.231 | 36.656 | 1.00 | 14.12 |
| 416 | O | HIS | 63 | .527 | 6.155 | 35.442 | 1.00 | 13.58 |
| 417 | N | LEU | 64 | .975 | 7.371 | 37.300 | 1.00 | 13.67 |
| 418 | CA | LEU | 64 | 1.039 | 8.657 | 36.629 | 1.00 | 14.24 |
| 419 | CB | LEU | 64 | −.157 | 9.534 | 37.017 | 1.00 | 14.20 |
| 420 | CG | LEU | 64 | −.348 | 10.859 | 36.269 | 1.00 | 13.73 |
| 421 | CD1 | LEU | 64 | −1.743 | 11.410 | 36.579 | 1.00 | 13.74 |
| 422 | CD2 | LEU | 64 | .728 | 11.857 | 36.672 | 1.00 | 13.72 |
| 423 | C | LEU | 64 | 2.332 | 9.262 | 37.148 | 1.00 | 14.32 |
| 424 | O | LEU | 64 | 2.483 | 9.500 | 38.348 | 1.00 | 14.19 |
| 425 | N | LEU | 65 | 3.274 | 9.477 | 36.241 | 1.00 | 14.06 |
| 426 | CA | LEU | 65 | 4.565 | 10.035 | 36.599 | 1.00 | 14.02 |
| 427 | CB | LEU | 65 | 5.679 | 9.243 | 35.903 | 1.00 | 14.26 |
| 428 | CG | LEU | 65 | 7.092 | 9.842 | 35.944 | 1.00 | 14.74 |
| 429 | CD1 | LEU | 65 | 7.665 | 9.719 | 37.343 | 1.00 | 14.55 |
| 430 | CD2 | LEU | 65 | 7.985 | 9.116 | 34.937 | 1.00 | 15.55 |
| 431 | C | LEU | 65 | 4.691 | 11.501 | 36.206 | 1.00 | 13.95 |
| 432 | O | LEU | 65 | 4.282 | 11.897 | 35.116 | 1.00 | 14.13 |
| 433 | N | VAL | 66 | 5.249 | 12.301 | 37.108 | 1.00 | 14.28 |
| 434 | CA | VAL | 66 | 5.505 | 13.705 | 36.821 | 1.00 | 14.89 |
| 435 | CB | VAL | 66 | 4.722 | 14.663 | 37.732 | 1.00 | 14.74 |
| 436 | CG1 | VAL | 66 | 5.136 | 16.114 | 37.436 | 1.00 | 14.38 |
| 437 | CG2 | VAL | 66 | 3.226 | 14.508 | 37.474 | 1.00 | 14.30 |
| 438 | C | VAL | 66 | 6.998 | 13.896 | 37.056 | 1.00 | 15.76 |
| 439 | O | VAL | 66 | 7.478 | 13.799 | 38.181 | 1.00 | 15.04 |
| 440 | N | LYS | 67 | 7.728 | 14.141 | 35.977 | 1.00 | 17.10 |
| 441 | CA | LYS | 67 | 9.170 | 14.323 | 36.060 | 1.00 | 19.07 |
| 442 | CB | LYS | 67 | 9.816 | 14.024 | 34.704 | 1.00 | 19.17 |
| 443 | CG | LYS | 67 | 9.681 | 12.576 | 34.249 | 1.00 | 19.96 |
| 444 | CD | LYS | 67 | 10.220 | 12.400 | 32.831 | 1.00 | 21.24 |
| 445 | CE | LYS | 67 | 10.079 | 10.963 | 32.351 | 1.00 | 22.22 |
| 446 | NZ | LYS | 67 | 10.514 | 10.819 | 30.931 | 1.00 | 23.59 |
| 447 | C | LYS | 67 | 9.554 | 15.722 | 36.486 | 1.00 | 20.36 |
| 448 | O | LYS | 67 | 8.754 | 16.657 | 36.427 | 1.00 | 19.61 |
| 449 | N | HIS | 68 | 10.788 | 15.852 | 36.944 | 1.00 | 22.14 |
| 450 | CA | HIS | 68 | 11.305 | 17.150 | 37.326 | 1.00 | 24.68 |
| 451 | CB | HIS | 68 | 10.959 | 17.500 | 38.781 | 1.00 | 23.82 |
| 452 | CG | HIS | 68 | 11.279 | 16.418 | 39.767 | 1.00 | 23.00 |
| 453 | CD2 | HIS | 68 | 10.535 | 15.376 | 40.206 | 1.00 | 22.29 |
| 454 | ND1 | HIS | 68 | 12.474 | 16.353 | 40.457 | 1.00 | 22.27 |
| 455 | CE1 | HIS | 68 | 12.447 | 15.317 | 41.279 | 1.00 | 22.06 |
| 456 | NE2 | HIS | 68 | 11.282 | 14.709 | 41.144 | 1.00 | 22.01 |
| 457 | C | HIS | 68 | 12.791 | 17.131 | 37.163 | 1.00 | 27.35 |
| 458 | O | HIS | 68 | 13.433 | 16.081 | 37.148 | 1.00 | 27.13 |
| 459 | N | SER | 69 | 13.355 | 18.308 | 36.994 | 1.00 | 30.89 |
| 460 | CA | SER | 69 | 14.775 | 18.308 | 36.897 | 1.00 | 34.40 |
| 461 | CB | SER | 69 | 15.244 | 18.838 | 35.543 | 1.00 | 34.61 |
| 462 | OG | SER | 69 | 15.706 | 20.178 | 35.621 | 1.00 | 35.84 |

TABLE 1-continued

| Atom | Atom Type | Residue | # | X | Y | Z | OCC | B |
|---|---|---|---|---|---|---|---|---|
| 463 | C | SER | 69 | 15.293 | 19.163 | 37.995 | 1.00 | 36.47 |
| 464 | O | SER | 69 | 14.590 | 19.957 | 38.598 | 1.00 | 37.00 |
| 465 | N | GLN | 70 | 16.583 | 18.973 | 38.223 | 1.00 | 38.95 |
| 466 | CA | GLN | 70 | 17.367 | 19.695 | 39.189 | 1.00 | 41.20 |
| 467 | CB | GLN | 70 | 17.492 | 18.890 | 40.487 | 1.00 | 41.86 |
| 468 | CG | GLN | 70 | 16.693 | 19.525 | 41.612 | 1.00 | 42.77 |
| 469 | CD | GLN | 70 | 15.738 | 20.580 | 41.084 | 1.00 | 43.51 |
| 470 | OE1 | GLN | 70 | 14.551 | 20.313 | 40.872 | 1.00 | 43.82 |
| 471 | NE2 | GLN | 70 | 16.262 | 21.783 | 40.840 | 1.00 | 43.80 |
| 472 | C | GLN | 70 | 18.677 | 19.796 | 38.428 | 1.00 | 42.52 |
| 473 | O | GLN | 70 | 19.652 | 20.399 | 38.907 | 1.00 | 42.72 |
| 474 | N | SER | 71 | 18.716 | 19.253 | 37.209 | 1.00 | 43.97 |
| 475 | CA | SER | 71 | 19.912 | 19.354 | 36.382 | 1.00 | 45.24 |
| 476 | CB | SER | 71 | 19.702 | 18.674 | 35.001 | 1.00 | 45.44 |
| 477 | OG | SER | 71 | 20.900 | 18.043 | 34.546 | 1.00 | 45.95 |
| 478 | C | SER | 71 | 20.205 | 20.854 | 36.231 | 1.00 | 46.00 |
| 479 | O | SER | 71 | 19.398 | 21.716 | 36.627 | 1.00 | 46.32 |
| 480 | N | ARG | 72 | 21.399 | 21.159 | 35.725 | 1.00 | 46.57 |
| 481 | CA | ARG | 72 | 21.850 | 22.537 | 35.500 | 1.00 | 46.94 |
| 482 | CB | ARG | 72 | 22.259 | 23.216 | 36.794 | 1.00 | 48.06 |
| 483 | CG | ARG | 72 | 21.684 | 22.526 | 38.005 | 1.00 | 49.63 |
| 484 | CD | ARG | 72 | 21.477 | 23.518 | 39.070 | 1.00 | 50.70 |
| 485 | NE | ARG | 72 | 20.485 | 23.091 | 40.041 | 1.00 | 51.89 |
| 486 | CZ | ARG | 72 | 20.430 | 23.601 | 41.262 | 1.00 | 52.35 |
| 487 | NH1 | ARG | 72 | 21.324 | 24.520 | 41.595 | 1.00 | 52.65 |
| 488 | NH2 | ARG | 72 | 19.489 | 23.230 | 42.128 | 1.00 | 52.66 |
| 489 | C | ARG | 72 | 23.062 | 22.479 | 34.601 | 1.00 | 46.51 |
| 490 | O | ARG | 72 | 24.184 | 22.798 | 35.024 | 1.00 | 46.64 |
| 491 | N | ARG | 73 | 22.814 | 22.081 | 33.360 | 1.00 | 45.96 |
| 492 | CA | ARG | 73 | 23.879 | 21.899 | 32.398 | 1.00 | 45.39 |
| 493 | CG | ARG | 73 | 24.151 | 19.544 | 31.589 | 1.00 | 47.17 |
| 494 | CD | ARG | 73 | 23.266 | 18.375 | 31.298 | 1.00 | 47.97 |
| 495 | NE | ARG | 73 | 23.914 | 17.121 | 31.650 | 1.00 | 48.93 |
| 496 | CZ | ARG | 73 | 23.247 | 16.008 | 31.924 | 1.00 | 49.41 |
| 497 | NH1 | ARG | 73 | 21.919 | 16.010 | 31.889 | 1.00 | 49.70 |
| 498 | NH2 | ARG | 73 | 23.903 | 14.894 | 32.224 | 1.00 | 49.54 |
| 499 | C | ARG | 73 | 24.299 | 23.187 | 31.764 | 1.00 | 44.29 |
| 500 | O | ARG | 73 | 23.573 | 24.172 | 31.815 | 1.00 | 44.19 |
| 501 | CB | ARG | 73 | 23.446 | 20.862 | 31.347 | 1.00 | 46.07 |
| 502 | N | PRO | 74 | 25.508 | 23.194 | 31.207 | 1.00 | 43.29 |
| 503 | CD | PRO | 74 | 26.463 | 22.081 | 31.312 | 1.00 | 43.00 |
| 504 | CA | PRO | 74 | 26.121 | 24.335 | 30.542 | 1.00 | 42.23 |
| 505 | CB | PRO | 74 | 27.530 | 23.825 | 30.237 | 1.00 | 42.68 |
| 506 | CG | PRO | 74 | 27.756 | 22.815 | 31.345 | 1.00 | 43.08 |
| 507 | C | PRO | 74 | 25.365 | 24.817 | 29.312 | 1.00 | 41.42 |
| 508 | O | PRO | 74 | 24.605 | 24.071 | 28.686 | 1.00 | 40.74 |
| 509 | N | SER | 75 | 25.596 | 26.086 | 28.995 | 1.00 | 40.30 |
| 510 | CA | SER | 75 | 24.978 | 26.779 | 27.871 | 1.00 | 39.65 |
| 511 | CB | SER | 75 | 25.718 | 28.096 | 27.652 | 1.00 | 39.45 |
| 512 | OG | SER | 75 | 27.103 | 27.849 | 27.475 | 1.00 | 38.69 |
| 513 | C | SER | 75 | 24.919 | 26.030 | 26.542 | 1.00 | 39.09 |
| 514 | O | SER | 75 | 23.947 | 26.156 | 25.800 | 1.00 | 39.22 |
| 515 | N | SER | 76 | 25.964 | 25.268 | 26.243 | 1.00 | 38.45 |
| 516 | CA | SER | 76 | 26.042 | 24.536 | 24.983 | 1.00 | 37.90 |
| 517 | CB | SER | 76 | 27.432 | 23.907 | 24.838 | 1.00 | 37.86 |
| 518 | OG | SER | 76 | 27.655 | 22.916 | 25.825 | 1.00 | 37.41 |
| 519 | C | SER | 76 | 24.974 | 23.458 | 24.772 | 1.00 | 37.78 |
| 520 | O | SER | 76 | 24.695 | 23.072 | 23.636 | 1.00 | 37.04 |
| 521 | N | TRP | 77 | 24.376 | 22.980 | 25.859 | 1.00 | 38.01 |
| 522 | CA | TRP | 77 | 23.353 | 21.939 | 25.772 | 1.00 | 38.39 |
| 523 | CB | TRP | 77 | 23.104 | 21.321 | 27.147 | 1.00 | 38.69 |
| 524 | CG | TRP | 77 | 24.202 | 20.436 | 27.604 | 1.00 | 39.13 |
| 525 | CD2 | TRP | 77 | 24.190 | 19.072 | 27.620 | 1.00 | 39.54 |
| 526 | CE2 | TRP | 77 | 25.453 | 18.583 | 28.084 | 1.00 | 39.63 |
| 527 | CE3 | TRP | 77 | 23.235 | 18.039 | 27.281 | 1.00 | 39.78 |
| 528 | CD1 | TRP | 77 | 25.432 | 20.816 | 28.050 | 1.00 | 39.41 |
| 529 | NE1 | TRP | 77 | 26.193 | 19.710 | 28.341 | 1.00 | 39.60 |
| 530 | CZ2 | TRP | 77 | 25.790 | 17.235 | 28.223 | 1.00 | 39.93 |
| 531 | CZ3 | TRP | 77 | 23.567 | 16.695 | 27.419 | 1.00 | 39.99 |
| 532 | CH2 | TRP | 77 | 24.837 | 16.307 | 27.884 | 1.00 | 39.98 |
| 533 | C | TRP | 77 | 22.013 | 22.393 | 25.209 | 1.00 | 38.68 |
| 534 | O | TRP | 77 | 21.617 | 23.545 | 25.373 | 1.00 | 38.13 |
| 535 | N | ARG | 78 | 21.314 | 21.473 | 24.550 | 1.00 | 39.18 |
| 536 | CA | ARG | 78 | 20.000 | 21.779 | 24.006 | 1.00 | 40.02 |
| 537 | CB | ARG | 78 | 19.468 | 20.624 | 23.159 | 1.00 | 40.57 |
| 538 | CG | ARG | 78 | 20.303 | 20.287 | 21.948 | 1.00 | 41.52 |
| 539 | CD | ARG | 78 | 19.546 | 19.358 | 21.017 | 1.00 | 42.62 |
| 540 | NE | ARG | 78 | 20.367 | 18.942 | 19.884 | 1.00 | 43.50 |
| 541 | CZ | ARG | 78 | 19.899 | 18.314 | 18.810 | 1.00 | 44.17 |
| 542 | NH1 | ARG | 78 | 18.609 | 18.027 | 18.716 | 1.00 | 44.45 |
| 543 | NH2 | ARG | 78 | 20.725 | 17.971 | 17.830 | 1.00 | 44.49 |
| 544 | C | ARG | 78 | 19.072 | 21.978 | 25.194 | 1.00 | 40.35 |
| 545 | O | ARG | 78 | 19.370 | 21.521 | 26.300 | 1.00 | 40.15 |
| 546 | N | GLN | 79 | 17.950 | 22.654 | 24.972 | 1.00 | 40.81 |
| 547 | CA | GLN | 79 | 16.994 | 22.880 | 26.049 | 1.00 | 41.57 |
| 548 | CB | GLN | 79 | 15.840 | 23.763 | 25.561 | 1.00 | 42.48 |
| 549 | CG | GLN | 79 | 14.838 | 24.149 | 26.645 | 1.00 | 44.22 |
| 550 | CD | GLN | 79 | 15.473 | 24.908 | 27.798 | 1.00 | 45.14 |
| 551 | OE1 | GLN | 79 | 14.780 | 25.377 | 28.700 | 1.00 | 46.06 |
| 552 | NE2 | GLN | 79 | 16.796 | 25.030 | 27.776 | 1.00 | 45.97 |
| 553 | C | GLN | 79 | 16.480 | 21.509 | 26.476 | 1.00 | 41.41 |
| 554 | O | GLN | 79 | 16.296 | 20.621 | 25.641 | 1.00 | 41.16 |
| 555 | N | GLU | 80 | 16.282 | 21.317 | 27.774 | 1.00 | 41.26 |
| 556 | CA | GLU | 80 | 15.805 | 20.028 | 28.242 | 1.00 | 41.34 |
| 557 | CB | GLU | 80 | 16.360 | 19.704 | 29.629 | 1.00 | 42.17 |
| 558 | CG | GLU | 80 | 17.053 | 18.345 | 29.680 | 1.00 | 43.75 |
| 559 | CD | GLU | 80 | 16.531 | 17.388 | 28.614 | 1.00 | 44.60 |
| 560 | OE1 | GLU | 80 | 16.839 | 17.586 | 27.415 | 1.00 | 45.22 |
| 561 | OE2 | GLU | 80 | 15.804 | 16.440 | 28.974 | 1.00 | 45.32 |
| 562 | C | GLU | 80 | 14.286 | 19.933 | 28.252 | 1.00 | 40.71 |
| 563 | O | GLU | 80 | 13.594 | 20.903 | 28.556 | 1.00 | 40.89 |
| 564 | N | LYS | 81 | 13.776 | 18.753 | 27.907 | 1.00 | 39.75 |
| 565 | CA | LYS | 81 | 12.335 | 18.527 | 27.863 | 1.00 | 38.73 |
| 566 | CB | LYS | 81 | 12.038 | 17.092 | 27.422 | 1.00 | 39.53 |
| 567 | CG | LYS | 81 | 12.528 | 16.771 | 26.017 | 1.00 | 40.66 |
| 568 | CD | LYS | 81 | 12.151 | 15.363 | 25.598 | 1.00 | 41.56 |
| 569 | CE | LYS | 81 | 12.619 | 15.066 | 24.183 | 1.00 | 42.08 |
| 570 | NZ | LYS | 81 | 12.261 | 13.672 | 23.798 | 1.00 | 43.00 |
| 571 | C | LYS | 81 | 11.663 | 18.812 | 29.202 | 1.00 | 37.41 |
| 572 | O | LYS | 81 | 10.620 | 19.468 | 29.253 | 1.00 | 37.57 |
| 573 | N | ILE | 82 | 12.256 | 18.318 | 30.283 | 1.00 | 35.76 |
| 574 | CA | ILE | 82 | 11.704 | 18.526 | 31.618 | 1.00 | 33.89 |
| 575 | CB | ILE | 82 | 11.863 | 17.257 | 32.484 | 1.00 | 34.19 |
| 576 | CG2 | ILE | 82 | 11.265 | 17.493 | 33.870 | 1.00 | 34.32 |
| 577 | CG1 | ILE | 82 | 11.204 | 16.059 | 31.789 | 1.00 | 34.07 |
| 578 | CD1 | ILE | 82 | 9.717 | 16.249 | 31.495 | 1.00 | 34.19 |
| 579 | C | ILE | 82 | 12.428 | 19.678 | 32.300 | 1.00 | 32.44 |
| 580 | O | ILE | 82 | 13.619 | 19.582 | 32.583 | 1.00 | 32.31 |
| 581 | N | THR | 83 | 11.711 | 20.765 | 32.564 | 1.00 | 30.82 |
| 582 | CA | THR | 83 | 12.324 | 21.923 | 33.208 | 1.00 | 29.02 |
| 583 | CB | THR | 83 | 12.286 | 23.164 | 32.289 | 1.00 | 29.78 |
| 584 | CG1 | THR | 83 | 10.924 | 23.520 | 32.010 | 1.00 | 30.24 |
| 585 | CG2 | THR | 83 | 12.993 | 22.875 | 30.971 | 1.00 | 29.97 |
| 586 | C | THR | 83 | 11.699 | 22.313 | 34.547 | 1.00 | 27.39 |
| 587 | O | THR | 83 | 12.239 | 23.155 | 35.261 | 1.00 | 27.09 |
| 588 | N | ARG | 84 | 10.572 | 21.705 | 34.900 | 1.00 | 25.23 |
| 589 | CA | ARG | 84 | 9.920 | 22.040 | 36.164 | 1.00 | 23.24 |
| 590 | CB | ARG | 84 | 8.515 | 21.430 | 36.226 | 1.00 | 22.24 |
| 591 | CG | ARG | 84 | 8.492 | 19.925 | 36.443 | 1.00 | 21.26 |
| 592 | CD | ARG | 84 | 7.063 | 19.431 | 36.615 | 1.00 | 19.83 |
| 593 | NE | ARG | 84 | 6.265 | 19.571 | 35.397 | 1.00 | 19.28 |
| 594 | CZ | ARG | 84 | 6.217 | 18.667 | 34.421 | 1.00 | 19.38 |
| 595 | NH1 | ARG | 84 | 5.458 | 18.882 | 33.354 | 1.00 | 20.14 |
| 596 | NH2 | ARG | 84 | 6.920 | 17.546 | 34.511 | 1.00 | 18.88 |
| 597 | C | ARG | 84 | 10.726 | 21.568 | 37.373 | 1.00 | 22.25 |
| 598 | O | ARG | 84 | 11.520 | 20.628 | 37.284 | 1.00 | 22.14 |
| 599 | N | THR | 85 | 10.507 | 22.223 | 38.509 | 1.00 | 21.24 |
| 600 | CA | THR | 85 | 11.199 | 21.872 | 39.745 | 1.00 | 20.32 |
| 601 | CB | THR | 85 | 11.266 | 23.065 | 40.714 | 1.00 | 20.06 |
| 602 | OG1 | THR | 85 | 9.938 | 23.413 | 41.132 | 1.00 | 18.89 |
| 603 | CG2 | THR | 85 | 11.923 | 24.273 | 40.040 | 1.00 | 19.65 |
| 604 | C | THR | 85 | 10.447 | 20.755 | 40.454 | 1.00 | 20.32 |
| 605 | O | THR | 85 | 9.307 | 20.440 | 40.097 | 1.00 | 20.01 |
| 606 | N | LYS | 86 | 11.088 | 20.166 | 41.460 | 1.00 | 20.00 |
| 607 | CA | LYS | 86 | 10.479 | 19.096 | 42.240 | 1.00 | 20.26 |
| 608 | CB | LYS | 86 | 11.461 | 18.588 | 43.302 | 1.00 | 20.47 |
| 609 | CG | LYS | 86 | 10.952 | 17.395 | 44.112 | 1.00 | 20.87 |
| 610 | CD | LYS | 86 | 11.883 | 17.061 | 45.283 | 1.00 | 21.04 |
| 611 | CE | LYS | 86 | 13.251 | 16.587 | 44.805 | 1.00 | 21.03 |
| 612 | NZ | LYS | 86 | 14.149 | 16.246 | 45.963 | 1.00 | 20.00 |
| 613 | C | LYS | 86 | 9.228 | 19.644 | 42.925 | 1.00 | 20.34 |
| 614 | O | LYS | 86 | 8.204 | 18.970 | 43.009 | 1.00 | 19.85 |

TABLE 1-continued

| Atom # | Atom Type | Residue | # | X | Y | Z | OCC | B |
|---|---|---|---|---|---|---|---|---|
| 615 | N | GLU | 87 | 9.328 | 20.877 | 43.412 | 1.00 | 21.05 |
| 616 | CA | GLU | 87 | 8.218 | 21.540 | 44.095 | 1.00 | 21.59 |
| 617 | CB | GLU | 87 | 8.662 | 22.931 | 44.559 | 1.00 | 23.73 |
| 618 | CG | GLU | 87 | 8.242 | 23.308 | 45.970 | 1.00 | 27.75 |
| 619 | CD | GLU | 87 | 8.596 | 24.748 | 46.313 | 1.00 | 29.66 |
| 620 | OE1 | GLU | 87 | 8.108 | 25.662 | 45.613 | 1.00 | 31.10 |
| 621 | OE2 | GLU | 87 | 9.363 | 24.969 | 47.277 | 1.00 | 31.37 |
| 622 | C | GLU | 87 | 7.013 | 21.668 | 43.158 | 1.00 | 20.66 |
| 623 | O | GLU | 87 | 5.871 | 21.408 | 43.548 | 1.00 | 20.58 |
| 624 | N | GLU | 88 | 7.273 | 22.073 | 41.920 | 1.00 | 19.90 |
| 625 | CA | GLU | 88 | 6.207 | 22.236 | 40.935 | 1.00 | 19.53 |
| 626 | CB | GLU | 88 | 6.751 | 22.936 | 39.685 | 1.00 | 20.43 |
| 627 | CG | GLU | 88 | 7.345 | 24.310 | 39.987 | 1.00 | 22.36 |
| 628 | CD | GLU | 88 | 7.932 | 25.004 | 38.767 | 1.00 | 23.16 |
| 629 | OE1 | GLU | 88 | 8.612 | 24.333 | 37.966 | 1.00 | 23.49 |
| 630 | OE2 | GLU | 88 | 7.728 | 26.228 | 38.618 | 1.00 | 24.89 |
| 631 | C | GLU | 88 | 5.613 | 20.877 | 40.575 | 1.00 | 18.58 |
| 632 | O | GLU | 88 | 4.407 | 20.753 | 40.363 | 1.00 | 17.85 |
| 633 | N | ALA | 89 | 6.466 | 19.858 | 40.520 | 1.00 | 17.78 |
| 634 | CA | ALA | 89 | 6.024 | 18.501 | 40.200 | 1.00 | 17.34 |
| 635 | CB | ALA | 89 | 7.236 | 17.580 | 40.028 | 1.00 | 16.41 |
| 636 | C | ALA | 89 | 5.121 | 17.970 | 41.311 | 1.00 | 16.99 |
| 637 | O | ALA | 89 | 4.104 | 17.322 | 41.045 | 1.00 | 17.06 |
| 638 | N | LEU | 90 | 5.496 | 18.239 | 42.559 | 1.00 | 16.95 |
| 639 | CA | LEU | 90 | 4.705 | 17.780 | 43.695 | 1.00 | 17.14 |
| 640 | CB | LEU | 90 | 5.448 | 18.036 | 45.015 | 1.00 | 17.39 |
| 641 | CG | LEU | 90 | 4.748 | 17.573 | 46.302 | 1.00 | 17.39 |
| 642 | CD1 | LEU | 90 | 4.317 | 16.112 | 46.175 | 1.00 | 18.00 |
| 643 | CD2 | LEU | 90 | 5.684 | 17.757 | 47.491 | 1.00 | 17.83 |
| 644 | C | LEU | 90 | 3.345 | 18.478 | 43.716 | 1.00 | 17.69 |
| 645 | O | LEU | 90 | 2.335 | 17.875 | 44.077 | 1.00 | 17.27 |
| 646 | N | GLU | 91 | 3.317 | 19.744 | 43.310 | 1.00 | 17.80 |
| 647 | CA | GLU | 91 | 2.069 | 20.496 | 43.292 | 1.00 | 18.89 |
| 648 | CB | GLU | 91 | 2.342 | 21.963 | 42.951 | 1.00 | 21.07 |
| 649 | CG | GLU | 91 | 1.173 | 22.894 | 43.219 | 1.00 | 25.71 |
| 650 | CD | GLU | 91 | 1.478 | 24.329 | 42.837 | 1.00 | 28.04 |
| 651 | OE1 | GLU | 91 | .813 | 25.247 | 43.368 | 1.00 | 30.67 |
| 652 | OE2 | GLU | 91 | 2.378 | 24.544 | 41.995 | 1.00 | 30.50 |
| 653 | C | GLU | 91 | 1.120 | 19.882 | 42.266 | 1.00 | 17.66 |
| 654 | O | GLU | 91 | −.080 | 19.749 | 42.514 | 1.00 | 17.03 |
| 655 | N | LEU | 92 | 1.662 | 19.507 | 41.110 | 1.00 | 16.95 |
| 656 | CA | LEU | 92 | .862 | 18.886 | 40.058 | 1.00 | 16.30 |
| 657 | CB | LEU | 92 | 1.714 | 18.684 | 38.803 | 1.00 | 16.11 |
| 658 | CG | LEU | 92 | 2.036 | 19.966 | 38.033 | 1.00 | 16.73 |
| 659 | CD1 | LEU | 92 | 3.163 | 19.720 | 37.043 | 1.00 | 16.34 |
| 660 | CD2 | LEU | 92 | .776 | 20.445 | 37.314 | 1.00 | 16.90 |
| 661 | C | LEU | 92 | .328 | 17.541 | 40.548 | 1.00 | 15.92 |
| 662 | O | LEU | 92 | −.846 | 17.207 | 40.350 | 1.00 | 16.13 |
| 663 | N | ILE | 93 | 1.198 | 16.774 | 41.194 | 1.00 | 15.17 |
| 664 | CA | ILE | 93 | .819 | 15.473 | 41.725 | 1.00 | 14.90 |
| 665 | CB | ILE | 93 | 2.029 | 14.760 | 42.386 | 1.00 | 14.64 |
| 666 | CG2 | ILE | 93 | 1.546 | 13.624 | 43.265 | 1.00 | 15.02 |
| 667 | CG1 | ILE | 93 | 2.992 | 14.240 | 41.311 | 1.00 | 14.63 |
| 668 | CD1 | ILE | 93 | 2.484 | 13.021 | 40.545 | 1.00 | 14.97 |
| 669 | C | ILE | 93 | −.297 | 15.606 | 42.760 | 1.00 | 14.72 |
| 670 | O | ILE | 93 | −1.256 | 14.835 | 42.744 | 1.00 | 13.96 |
| 671 | N | ASN | 94 | −.167 | 16.569 | 43.668 | 1.00 | 14.85 |
| 672 | CA | ASN | 94 | −1.189 | 16.748 | 44.691 | 1.00 | 15.33 |
| 673 | CB | ASN | 94 | −.744 | 17.769 | 45.741 | 1.00 | 16.49 |
| 674 | CG | ASN | 94 | .274 | 17.195 | 46.707 | 1.00 | 17.60 |
| 675 | OD1 | ASN | 94 | .176 | 16.035 | 47.103 | 1.00 | 18.59 |
| 676 | ND2 | ASN | 94 | 1.250 | 18.007 | 47.100 | 1.00 | 18.55 |
| 677 | C | ASN | 94 | −2.522 | 17.164 | 44.086 | 1.00 | 15.00 |
| 678 | O | ASN | 94 | −3.578 | 16.753 | 44.564 | 1.00 | 14.46 |
| 679 | N | GLY | 95 | −2.466 | 17.979 | 43.039 | 1.00 | 15.04 |
| 680 | CA | GLY | 95 | −3.685 | 18.416 | 42.377 | 1.00 | 15.34 |
| 681 | C | GLY | 95 | −4.395 | 17.252 | 41.706 | 1.00 | 15.58 |
| 682 | O | GLY | 95 | −5.628 | 17.159 | 41.740 | 1.00 | 15.72 |
| 683 | N | TYR | 96 | −3.625 | 16.361 | 41.083 | 1.00 | 15.31 |
| 684 | CA | TYR | 96 | −4.209 | 15.194 | 40.418 | 1.00 | 15.14 |
| 685 | CB | TYR | 96 | −3.133 | 14.421 | 39.638 | 1.00 | 14.76 |
| 686 | CG | TYR | 96 | −2.507 | 15.178 | 38.480 | 1.00 | 14.80 |
| 687 | CD1 | TYR | 96 | −1.199 | 14.907 | 38.077 | 1.00 | 14.82 |
| 688 | CE1 | TYR | 96 | −.603 | 15.611 | 37.025 | 1.00 | 14.68 |
| 689 | CD2 | TYR | 96 | −3.213 | 16.173 | 37.795 | 1.00 | 14.83 |
| 690 | CE2 | TYR | 96 | −2.627 | 16.880 | 36.742 | 1.00 | 15.07 |
| 691 | CZ | TYR | 96 | −1.322 | 16.597 | 36.364 | 1.00 | 15.37 |
| 692 | OH | TYR | 96 | −.730 | 17.309 | 35.340 | 1.00 | 15.34 |
| 693 | C | TYR | 96 | −4.851 | 14.277 | 41.464 | 1.00 | 15.43 |
| 694 | O | TYR | 96 | −5.944 | 13.744 | 41.254 | 1.00 | 15.65 |
| 695 | N | ILE | 97 | −4.173 | 14.095 | 42.593 | 1.00 | 15.43 |
| 696 | CA | ILE | 97 | −4.696 | 13.251 | 43.663 | 1.00 | 15.72 |
| 697 | CB | ILE | 97 | −3.694 | 13.190 | 44.853 | 1.00 | 15.76 |
| 698 | CG2 | ILE | 97 | −4.374 | 12.677 | 46.118 | 1.00 | 14.84 |
| 699 | CG1 | ILE | 97 | −2.506 | 12.300 | 44.465 | 1.00 | 15.25 |
| 700 | CD1 | ILE | 97 | −1.377 | 12.270 | 45.499 | 1.00 | 15.69 |
| 701 | C | ILE | 97 | −6.047 | 13.794 | 44.133 | 1.00 | 16.67 |
| 702 | O | ILE | 97 | −7.005 | 13.038 | 44.312 | 1.00 | 16.00 |
| 703 | N | GLN | 98 | −6.123 | 15.107 | 44.310 | 1.00 | 17.89 |
| 704 | CA | GLN | 98 | −7.356 | 15.741 | 44.762 | 1.00 | 19.99 |
| 705 | CB | GLN | 98 | −7.097 | 17.229 | 45.041 | 1.00 | 21.22 |
| 706 | CG | GLN | 98 | −8.316 | 18.042 | 45.451 | 1.00 | 24.46 |
| 707 | CD | GLN | 98 | −9.163 | 18.456 | 44.265 | 1.00 | 26.01 |
| 708 | OE1 | GLN | 98 | −8.660 | 19.043 | 43.306 | 1.00 | 27.99 |
| 709 | NE2 | GLN | 98 | −10.457 | 18.160 | 44.325 | 1.00 | 27.84 |
| 710 | C | GLN | 98 | −8.478 | 15.557 | 43.739 | 1.00 | 20.39 |
| 711 | O | GLN | 98 | −9.612 | 15.240 | 44.101 | 1.00 | 20.54 |
| 712 | N | LYS | 99 | −8.165 | 15.736 | 42.460 | 1.00 | 20.86 |
| 713 | CA | LYS | 99 | −9.178 | 15.568 | 41.422 | 1.00 | 21.63 |
| 714 | CB | LYS | 99 | −8.646 | 16.059 | 40.076 | 1.00 | 22.60 |
| 715 | CG | LYS | 99 | −8.350 | 17.547 | 40.067 | 1.00 | 24.81 |
| 716 | CD | LYS | 99 | −7.996 | 18.043 | 38.681 | 1.00 | 26.48 |
| 717 | CE | LYS | 99 | −7.733 | 19.537 | 38.699 | 1.00 | 27.73 |
| 718 | NZ | LYS | 99 | −7.488 | 20.068 | 37.328 | 1.00 | 29.53 |
| 719 | C | LYS | 99 | −9.637 | 14.116 | 41.307 | 1.00 | 21.51 |
| 720 | O | LYS | 99 | −10.804 | 13.845 | 41.013 | 1.00 | 21.72 |
| 721 | N | ILE | 100 | −8.724 | 13.178 | 41.533 | 1.00 | 21.05 |
| 722 | CA | ILE | 100 | −9.088 | 11.771 | 41.457 | 1.00 | 21.23 |
| 723 | CB | ILE | 100 | −7.839 | 10.865 | 41.386 | 1.00 | 20.66 |
| 724 | CG2 | ILE | 100 | −8.255 | 9.395 | 41.410 | 1.00 | 20.61 |
| 725 | CG1 | ILE | 100 | −7.069 | 11.159 | 40.096 | 1.00 | 20.42 |
| 726 | CD1 | ILE | 100 | −5.754 | 10.417 | 39.975 | 1.00 | 19.93 |
| 727 | C | ILE | 100 | −9.944 | 11.372 | 42.661 | 1.00 | 21.63 |
| 728 | O | ILE | 100 | −10.955 | 10.685 | 42.509 | 1.00 | 21.63 |
| 729 | N | LYS | 101 | −9.547 | 11.807 | 43.853 | 1.00 | 22.26 |
| 730 | CA | LYS | 101 | −10.307 | 11.486 | 45.062 | 1.00 | 23.36 |
| 731 | CB | LYS | 101 | −9.562 | 11.950 | 46.314 | 1.00 | 23.20 |
| 732 | CG | LYS | 101 | −8.388 | 11.082 | 46.730 | 1.00 | 23.79 |
| 733 | CD | LYS | 101 | −7.875 | 11.560 | 48.079 | 1.00 | 24.34 |
| 734 | CE | LYS | 101 | −6.877 | 10.600 | 48.690 | 1.00 | 24.70 |
| 735 | NZ | LYS | 101 | −6.498 | 11.046 | 50.064 | 1.00 | 23.81 |
| 736 | C | LYS | 101 | −11.688 | 12.135 | 45.056 | 1.00 | 24.39 |
| 737 | O | LYS | 101 | −12.651 | 11.566 | 45.574 | 1.00 | 24.32 |
| 738 | N | SER | 102 | −11.782 | 13.327 | 44.474 | 1.00 | 25.07 |
| 739 | CA | SER | 102 | −13.054 | 14.043 | 44.426 | 1.00 | 26.47 |
| 740 | CB | SER | 102 | −12.819 | 15.541 | 44.216 | 1.00 | 25.83 |
| 741 | OG | SER | 102 | −12.411 | 15.815 | 42.888 | 1.00 | 26.55 |
| 742 | C | SER | 102 | −13.962 | 13.517 | 43.320 | 1.00 | 27.01 |
| 743 | O | SER | 102 | −15.095 | 13.976 | 43.173 | 1.00 | 27.74 |
| 744 | N | GLY | 103 | −13.464 | 12.557 | 42.547 | 1.00 | 27.70 |
| 745 | CA | GLY | 103 | −14.251 | 11.994 | 41.464 | 1.00 | 28.32 |
| 746 | C | GLY | 103 | −14.384 | 12.963 | 40.307 | 1.00 | 28.85 |
| 747 | O | GLY | 103 | −15.220 | 12.786 | 39.422 | 1.00 | 28.97 |
| 748 | N | GLU | 104 | −13.548 | 13.994 | 40.315 | 1.00 | 29.48 |
| 749 | CA | GLU | 104 | −13.563 | 15.002 | 39.269 | 1.00 | 30.20 |
| 750 | CB | GLU | 104 | −12.844 | 16.257 | 39.771 | 1.00 | 31.32 |
| 751 | CG | GLU | 104 | −13.397 | 17.559 | 39.234 | 1.00 | 33.04 |
| 752 | CD | GLU | 104 | −12.662 | 18.766 | 39.785 | 1.00 | 33.86 |
| 753 | OE1 | GLU | 104 | −12.786 | 19.045 | 40.997 | 1.00 | 34.38 |
| 754 | OE2 | GLU | 104 | −11.951 | 19.430 | 39.002 | 1.00 | 34.72 |
| 755 | C | GLU | 104 | −12.882 | 14.458 | 38.007 | 1.00 | 30.26 |
| 756 | O | GLU | 104 | −13.263 | 14.801 | 36.888 | 1.00 | 30.35 |
| 757 | N | GLU | 105 | −11.883 | 13.601 | 38.206 | 1.00 | 30.18 |
| 758 | CA | GLU | 105 | −11.130 | 12.981 | 37.114 | 1.00 | 30.07 |
| 759 | CB | GLU | 105 | −9.756 | 13.642 | 36.959 | 1.00 | 31.02 |
| 760 | CG | GLU | 105 | −9.746 | 15.029 | 36.351 | 1.00 | 32.41 |
| 761 | CD | GLU | 105 | −10.173 | 15.032 | 34.898 | 1.00 | 33.59 |
| 762 | OE1 | GLU | 105 | −9.852 | 14.063 | 34.177 | 1.00 | 34.67 |
| 763 | OE2 | GLU | 105 | −10.819 | 16.011 | 34.474 | 1.00 | 34.33 |
| 764 | C | GLU | 105 | −10.909 | 11.498 | 37.399 | 1.00 | 29.47 |
| 765 | O | GLU | 105 | −10.869 | 11.082 | 38.556 | 1.00 | 28.99 |
| 766 | N | ASP | 106 | −10.759 | 10.712 | 36.336 | 1.00 | 28.81 |

TABLE 1-continued

| Atom | Atom Type | Residue | # | X | Y | Z | OCC | B |
|---|---|---|---|---|---|---|---|---|
| 767 | CA | ASP | 106 | −10.505 | 9.277 | 36.450 | 1.00 | 28.64 |
| 768 | CB | ASP | 106 | −11.174 | 8.529 | 35.291 | 1.00 | 30.47 |
| 769 | CG | ASP | 106 | −10.814 | 7.049 | 35.247 | 1.00 | 32.34 |
| 770 | OD1 | ASP | 106 | −10.010 | 6.585 | 36.082 | 1.00 | 34.04 |
| 771 | OD2 | ASP | 106 | −11.339 | 6.344 | 34.360 | 1.00 | 34.29 |
| 772 | C | ASP | 106 | −8.986 | 9.096 | 36.381 | 1.00 | 27.37 |
| 773 | O | ASP | 106 | −8.313 | 9.782 | 35.614 | 1.00 | 26.92 |
| 774 | N | PHE | 107 | −8.451 | 8.185 | 37.190 | 1.00 | 26.16 |
| 775 | CA | PHE | 107 | −7.012 | 7.929 | 37.209 | 1.00 | 25.20 |
| 776 | CB | PHE | 107 | −6.696 | 6.709 | 38.081 | 1.00 | 24.24 |
| 777 | CG | PHE | 107 | −5.224 | 6.472 | 38.281 | 1.00 | 23.95 |
| 778 | CD1 | PHE | 107 | −4.544 | 7.093 | 39.323 | 1.00 | 23.66 |
| 779 | CD2 | PHE | 107 | −4.511 | 5.647 | 37.414 | 1.00 | 24.12 |
| 780 | CE1 | PHE | 107 | −3.175 | 6.898 | 39.502 | 1.00 | 24.18 |
| 781 | CE2 | PHE | 107 | −3.141 | 5.447 | 37.583 | 1.00 | 23.65 |
| 782 | CZ | PHE | 107 | −2.473 | 6.074 | 38.630 | 1.00 | 23.73 |
| 783 | C | PHE | 107 | −6.465 | 7.669 | 35.808 | 1.00 | 24.77 |
| 784 | O | PHE | 107 | −5.519 | 8.318 | 35.371 | 1.00 | 24.13 |
| 785 | N | GLU | 108 | −7.063 | 6.702 | 35.117 | 1.00 | 25.00 |
| 786 | CA | GLU | 108 | −6.628 | 6.321 | 33.777 | 1.00 | 25.31 |
| 787 | CB | GLU | 108 | −7.537 | 5.220 | 33.217 | 1.00 | 27.41 |
| 788 | CG | GLU | 108 | −7.681 | 4.007 | 34.121 | 1.00 | 30.11 |
| 789 | CD | GLU | 108 | −6.406 | 3.684 | 34.874 | 1.00 | 31.74 |
| 790 | OE1 | GLU | 108 | −5.317 | 3.749 | 34.266 | 1.00 | 33.45 |
| 791 | OE2 | GLU | 108 | −6.492 | 3.356 | 36.075 | 1.00 | 33.16 |
| 792 | C | GLU | 108 | −6.577 | 7.480 | 32.795 | 1.00 | 24.42 |
| 793 | O | GLU | 108 | −5.633 | 7.596 | 32.009 | 1.00 | 23.83 |
| 794 | N | SER | 109 | −7.595 | 8.333 | 32.829 | 1.00 | 23.77 |
| 795 | CA | SER | 109 | −7.636 | 9.477 | 31.928 | 1.00 | 23.12 |
| 796 | CB | SER | 109 | −8.978 | 10.202 | 32.044 | 1.00 | 23.92 |
| 797 | OG | SER | 109 | −10.028 | 9.358 | 31.614 | 1.00 | 26.22 |
| 798 | C | SER | 109 | −6.498 | 10.444 | 32.227 | 1.00 | 22.01 |
| 799 | O | SER | 109 | −5.798 | 10.879 | 31.316 | 1.00 | 21.55 |
| 800 | N | LEU | 110 | −6.310 | 10.778 | 33.500 | 1.00 | 20.63 |
| 801 | CA | LEU | 110 | −5.241 | 11.694 | 33.878 | 1.00 | 19.76 |
| 802 | CB | LEU | 110 | −5.321 | 12.040 | 35.370 | 1.00 | 20.30 |
| 803 | CG | LEU | 110 | −6.340 | 13.107 | 35.789 | 1.00 | 20.86 |
| 804 | CD1 | LEU | 110 | −6.242 | 13.339 | 37.290 | 1.00 | 20.75 |
| 805 | CD2 | LEU | 110 | −6.075 | 14.407 | 35.037 | 1.00 | 21.02 |
| 806 | C | LEU | 110 | −3.869 | 11.106 | 33.556 | 1.00 | 18.88 |
| 807 | O | LEU | 110 | −2.967 | 11.827 | 33.134 | 1.00 | 17.78 |
| 808 | N | ALA | 111 | −3.709 | 9.801 | 33.755 | 1.00 | 17.96 |
| 809 | CA | ALA | 111 | −2.432 | 9.153 | 33.454 | 1.00 | 17.91 |
| 810 | CB | ALA | 111 | −2.477 | 7.686 | 33.851 | 1.00 | 18.09 |
| 811 | C | ALA | 111 | −2.172 | 9.283 | 31.954 | 1.00 | 17.72 |
| 812 | O | ALA | 111 | −1.098 | 9.704 | 31.520 | 1.00 | 17.17 |
| 813 | N | SER | 112 | −3.168 | 8.923 | 31.159 | 1.00 | 17.81 |
| 814 | CA | SER | 112 | −3.037 | 9.028 | 29.715 | 1.00 | 18.41 |
| 815 | CB | SER | 112 | −4.328 | 8.570 | 29.035 | 1.00 | 19.02 |
| 816 | OG | SER | 112 | −4.387 | 9.068 | 27.711 | 1.00 | 21.29 |
| 817 | C | SER | 112 | −2.739 | 10.466 | 29.293 | 1.00 | 18.43 |
| 818 | O | SER | 112 | −1.971 | 10.709 | 28.368 | 1.00 | 18.42 |
| 819 | N | GLN | 113 | −3.340 | 11.424 | 29.982 | 1.00 | 18.81 |
| 820 | CA | GLN | 113 | −3.151 | 12.824 | 29.624 | 1.00 | 19.37 |
| 821 | CB | GLN | 113 | −4.337 | 13.641 | 30.133 | 1.00 | 21.64 |
| 822 | CG | GLN | 113 | −5.682 | 13.134 | 29.647 | 1.00 | 25.68 |
| 823 | CD | GLN | 113 | −6.845 | 13.873 | 30.284 | 1.00 | 27.75 |
| 824 | OE1 | GLN | 113 | −7.061 | 15.054 | 30.020 | 1.00 | 29.55 |
| 825 | NE2 | GLN | 113 | −7.594 | 13.181 | 31.138 | 1.00 | 29.42 |
| 826 | C | GLN | 113 | −1.859 | 13.491 | 30.083 | 1.00 | 18.45 |
| 827 | O | GLN | 113 | −1.195 | 14.176 | 29.298 | 1.00 | 17.89 |
| 828 | N | PHE | 114 | −1.488 | 13.284 | 31.342 | 1.00 | 17.63 |
| 829 | CA | PHE | 114 | −.303 | 13.944 | 31.878 | 1.00 | 16.49 |
| 830 | CB | PHE | 114 | −.716 | 14.812 | 33.075 | 1.00 | 16.64 |
| 831 | CG | PHE | 114 | −1.748 | 15.854 | 32.744 | 1.00 | 16.37 |
| 832 | CD1 | PHE | 114 | −3.079 | 15.677 | 33.104 | 1.00 | 16.38 |
| 833 | CD2 | PHE | 114 | −1.390 | 17.008 | 32.056 | 1.00 | 16.56 |
| 834 | CE1 | PHE | 114 | −4.041 | 16.634 | 32.783 | 1.00 | 16.78 |
| 835 | CE2 | PHE | 114 | −2.346 | 17.972 | 31.729 | 1.00 | 16.83 |
| 836 | CZ | PHE | 114 | −3.673 | 17.783 | 32.094 | 1.00 | 16.82 |
| 837 | C | PHE | 114 | .925 | 13.123 | 32.275 | 1.00 | 16.31 |
| 838 | O | PHE | 114 | 1.980 | 13.699 | 32.530 | 1.00 | 15.70 |
| 839 | N | SER | 115 | .826 | 11.799 | 32.334 | 1.00 | 15.56 |
| 840 | CA | SER | 115 | 2.004 | 11.031 | 32.739 | 1.00 | 15.15 |
| 841 | CB | SER | 115 | 1.680 | 9.541 | 32.869 | 1.00 | 14.74 |
| 842 | OG | SER | 115 | 2.809 | 8.848 | 33.368 | 1.00 | 14.19 |
| 843 | C | SER | 115 | 3.186 | 11.198 | 31.790 | 1.00 | 15.11 |
| 844 | O | SER | 115 | 3.035 | 11.125 | 30.568 | 1.00 | 14.46 |
| 845 | N | ASP | 116 | 4.367 | 11.415 | 32.367 | 1.00 | 15.77 |
| 846 | CA | ASP | 116 | 5.585 | 11.578 | 31.588 | 1.00 | 16.46 |
| 847 | CB | ASP | 116 | 6.574 | 12.501 | 32.308 | 1.00 | 17.13 |
| 848 | CG | ASP | 116 | 6.096 | 13.936 | 32.370 | 1.00 | 17.71 |
| 849 | OD1 | ASP | 116 | 5.608 | 14.444 | 31.338 | 1.00 | 17.42 |
| 850 | OD2 | ASP | 116 | 6.227 | 14.560 | 33.448 | 1.00 | 17.33 |
| 851 | C | ASP | 116 | 6.266 | 10.240 | 31.315 | 1.00 | 16.84 |
| 852 | O | ASP | 116 | 7.328 | 10.201 | 30.696 | 1.00 | 16.78 |
| 853 | N | CYS | 117 | 5.662 | 9.152 | 31.783 | 1.00 | 17.14 |
| 854 | CA | CYS | 117 | 6.219 | 7.819 | 31.561 | 1.00 | 17.56 |
| 855 | CB | CYS | 117 | 5.750 | 6.852 | 32.659 | 1.00 | 17.77 |
| 856 | SG | CYS | 117 | 6.249 | 5.108 | 32.431 | 1.00 | 16.67 |
| 857 | C | CYS | 117 | 5.743 | 7.322 | 30.199 | 1.00 | 18.18 |
| 858 | O | CYS | 117 | 4.696 | 7.739 | 29.716 | 1.00 | 18.41 |
| 859 | N | SER | 118 | 6.512 | 6.438 | 29.576 | 1.00 | 18.50 |
| 860 | CA | SER | 118 | 6.112 | 5.912 | 28.279 | 1.00 | 18.95 |
| 861 | CB | SER | 118 | 7.211 | 5.016 | 27.696 | 1.00 | 18.49 |
| 862 | OG | SER | 118 | 7.559 | 3.980 | 28.595 | 1.00 | 21.13 |
| 863 | C | SER | 118 | 4.804 | 5.129 | 28.402 | 1.00 | 18.40 |
| 864 | O | SER | 118 | 4.129 | 4.903 | 27.406 | 1.00 | 18.98 |
| 865 | N | SER | 119 | 4.444 | 4.730 | 29.621 | 1.00 | 17.70 |
| 866 | CA | SER | 119 | 3.210 | 3.978 | 29.839 | 1.00 | 17.55 |
| 867 | CB | SER | 119 | 3.231 | 3.296 | 31.216 | 1.00 | 17.12 |
| 868 | OG | SER | 119 | 3.409 | 4.232 | 32.267 | 1.00 | 17.70 |
| 869 | C | SER | 119 | 1.943 | 4.824 | 29.694 | 1.00 | 17.65 |
| 870 | O | SER | 119 | .832 | 4.303 | 29.762 | 1.00 | 17.04 |
| 871 | N | ALA | 120 | 2.102 | 6.129 | 29.493 | 1.00 | 18.34 |
| 872 | CA | ALA | 120 | .940 | 6.996 | 29.326 | 1.00 | 19.11 |
| 873 | CB | ALA | 120 | 1.382 | 8.434 | 29.025 | 1.00 | 18.80 |
| 874 | C | ALA | 120 | .094 | 6.456 | 28.177 | 1.00 | 20.07 |
| 875 | O | ALA | 120 | −1.124 | 6.587 | 28.183 | 1.00 | 20.60 |
| 876 | N | LYS | 121 | .760 | 5.839 | 27.205 | 1.00 | 21.40 |
| 877 | CA | LYS | 121 | .113 | 5.270 | 26.029 | 1.00 | 23.04 |
| 878 | CB | LYS | 121 | 1.174 | 4.772 | 25.033 | 1.00 | 24.04 |
| 879 | CG | LYS | 121 | 2.375 | 4.003 | 25.643 | 1.00 | 26.30 |
| 880 | CD | LYS | 121 | 1.952 | 3.082 | 26.821 | 1.00 | 27.30 |
| 881 | CE | LYS | 121 | 2.768 | 1.783 | 26.870 | 1.00 | 27.75 |
| 882 | NZ | LYS | 121 | 3.627 | 1.586 | 28.056 | 1.00 | 27.81 |
| 883 | C | LYS | 121 | −.839 | 4.120 | 26.350 | 1.00 | 22.95 |
| 884 | O | LYS | 121 | −1.779 | 3.854 | 25.594 | 1.00 | 23.43 |
| 885 | N | ALA | 122 | −.577 | 3.442 | 27.462 | 1.00 | 22.05 |
| 886 | CA | ALA | 122 | −1.381 | 2.313 | 27.893 | 1.00 | 21.66 |
| 887 | CB | ALA | 122 | −.478 | 1.124 | 28.197 | 1.00 | 21.46 |
| 888 | C | ALA | 122 | −2.202 | 2.680 | 29.120 | 1.00 | 21.15 |
| 889 | O | ALA | 122 | −2.392 | 1.857 | 30.012 | 1.00 | 20.73 |
| 890 | N | ARG | 123 | −2.674 | 3.924 | 29.159 | 1.00 | 21.13 |
| 891 | CA | ARG | 123 | −3.487 | 4.411 | 30.268 | 1.00 | 21.04 |
| 892 | CB | ARG | 123 | −4.824 | 3.665 | 30.297 | 1.00 | 23.15 |
| 893 | CG | ARG | 123 | −5.581 | 3.701 | 28.958 | 1.00 | 26.27 |
| 894 | CD | ARG | 123 | −6.304 | 5.022 | 28.731 | 1.00 | 28.68 |
| 895 | NE | ARG | 123 | −7.714 | 4.953 | 29.113 | 1.00 | 31.32 |
| 896 | CZ | ARG | 123 | −8.507 | 6.012 | 29.256 | 1.00 | 32.33 |
| 897 | NH1 | ARG | 123 | −8.028 | 7.233 | 29.058 | 1.00 | 32.20 |
| 898 | NH2 | ARG | 123 | −9.787 | 5.851 | 29.583 | 1.00 | 33.68 |
| 899 | C | ARG | 123 | −2.774 | 4.251 | 31.611 | 1.00 | 19.65 |
| 900 | O | ARG | 123 | −3.415 | 4.092 | 32.648 | 1.00 | 19.56 |
| 901 | N | GLY | 124 | −1.446 | 4.288 | 31.580 | 1.00 | 18.71 |
| 902 | CA | GLY | 124 | −.655 | 4.173 | 32.798 | 1.00 | 17.23 |
| 903 | C | GLY | 124 | −.310 | 2.772 | 33.278 | 1.00 | 16.46 |
| 904 | O | GLY | 124 | .450 | 2.614 | 34.229 | 1.00 | 15.56 |
| 905 | N | ASP | 125 | −.844 | 1.753 | 32.615 | 1.00 | 15.86 |
| 906 | CA | ASP | 125 | −.594 | .367 | 33.020 | 1.00 | 15.68 |
| 907 | CB | ASP | 125 | −1.498 | −.572 | 32.217 | 1.00 | 15.08 |
| 908 | CG | ASP | 125 | −1.275 | −2.038 | 32.558 | 1.00 | 15.67 |
| 909 | OD1 | ASP | 125 | −1.217 | −2.377 | 33.760 | 1.00 | 15.93 |
| 910 | OD2 | ASP | 125 | −1.168 | −2.850 | 31.618 | 1.00 | 15.30 |
| 911 | C | ASP | 125 | .863 | −.082 | 32.886 | 1.00 | 15.76 |
| 912 | O | ASP | 125 | 1.488 | .081 | 31.834 | 1.00 | 16.52 |
| 913 | N | LEU | 126 | 1.395 | −.648 | 33.964 | 1.00 | 15.57 |
| 914 | CA | LEU | 126 | 2.766 | −1.146 | 33.991 | 1.00 | 15.90 |
| 915 | CB | LEU | 126 | 3.484 | −.651 | 35.248 | 1.00 | 15.81 |
| 916 | CG | LEU | 126 | 3.767 | .852 | 35.318 | 1.00 | 16.01 |
| 917 | CD1 | LEU | 126 | 4.334 | 1.196 | 36.682 | 1.00 | 16.63 |
| 918 | CD2 | LEU | 126 | 4.742 | 1.244 | 34.226 | 1.00 | 16.49 |

TABLE 1-continued

| Atom | Atom Type | Residue | # | X | Y | Z | OCC | B |
|---|---|---|---|---|---|---|---|---|
| 919 | C | LEU | 126 | 2.786 | −2.668 | 33.973 | 1.00 | 16.16 |
| 920 | O | LEU | 126 | 3.852 | −3.279 | 33.877 | 1.00 | 16.15 |
| 921 | N | GLY | 127 | 1.605 | −3.273 | 34.075 | 1.00 | 16.31 |
| 922 | CA | GLY | 127 | 1.508 | −4.724 | 34.073 | 1.00 | 16.75 |
| 923 | C | GLY | 127 | 1.758 | −5.324 | 35.443 | 1.00 | 17.20 |
| 924 | O | GLY | 127 | 1.926 | −4.597 | 36.424 | 1.00 | 17.15 |
| 925 | N | ALA | 128 | 1.779 | −6.651 | 35.515 | 1.00 | 17.39 |
| 926 | CA | ALA | 128 | 2.009 | −7.342 | 36.778 | 1.00 | 17.94 |
| 927 | CB | ALA | 128 | 1.258 | −8.663 | 36.801 | 1.00 | 17.86 |
| 928 | C | ALA | 128 | 3.497 | −7.580 | 36.985 | 1.00 | 18.17 |
| 929 | O | ALA | 128 | 4.215 | −7.941 | 36.057 | 1.00 | 18.00 |
| 930 | N | PHE | 129 | 3.953 | −7.374 | 38.213 | 1.00 | 18.92 |
| 931 | CA | PHE | 129 | 5.358 | −7.557 | 38.534 | 1.00 | 19.63 |
| 932 | CB | PHE | 129 | 6.089 | −6.216 | 38.391 | 1.00 | 19.19 |
| 933 | CG | PHE | 129 | 5.499 | −5.103 | 39.222 | 1.00 | 19.33 |
| 934 | CD1 | PHE | 129 | 5.909 | −4.905 | 40.537 | 1.00 | 19.45 |
| 935 | CD2 | PHE | 129 | 4.529 | −4.261 | 38.691 | 1.00 | 18.82 |
| 936 | CE1 | PHE | 129 | 5.365 | −3.883 | 41.309 | 1.00 | 19.62 |
| 937 | CE2 | PHE | 129 | 3.975 | −3.232 | 39.458 | 1.00 | 19.34 |
| 938 | CZ | PHE | 129 | 4.395 | −3.044 | 40.770 | 1.00 | 19.20 |
| 939 | C | PHE | 129 | 5.542 | −8.126 | 39.938 | 1.00 | 20.48 |
| 940 | O | PHE | 129 | 4.605 | −8.161 | 40.738 | 1.00 | 19.68 |
| 941 | N | SER | 130 | 6.754 | −8.590 | 40.222 | 1.00 | 21.37 |
| 942 | CA | SER | 130 | 7.075 | −9.151 | 41.527 | 1.00 | 22.50 |
| 943 | CB | SER | 130 | 7.598 | −10.579 | 41.370 | 1.00 | 23.11 |
| 944 | OG | SER | 130 | 8.770 | −10.584 | 40.576 | 1.00 | 25.03 |
| 945 | C | SER | 130 | 8.155 | −8.272 | 42.136 | 1.00 | 22.77 |
| 946 | O | SER | 130 | 8.659 | −7.363 | 41.477 | 1.00 | 22.66 |
| 947 | N | ARG | 131 | 8.509 | −8.530 | 43.391 | 1.00 | 23.44 |
| 948 | CA | ARG | 131 | 9.550 | −7.737 | 44.029 | 1.00 | 24.18 |
| 949 | CB | ARG | 131 | 9.692 | −8.102 | 45.514 | 1.00 | 24.60 |
| 950 | CG | ARG | 131 | 8.690 | −7.390 | 46.429 | 1.00 | 24.92 |
| 951 | CD | ARG | 131 | 8.964 | −7.684 | 47.898 | 1.00 | 25.89 |
| 952 | NE | ARG | 131 | 8.045 | −7.001 | 48.809 | 1.00 | 25.89 |
| 953 | CZ | ARG | 131 | 8.074 | −5.700 | 49.089 | 1.00 | 26.18 |
| 954 | NH1 | ARG | 131 | 8.979 | −4.910 | 48.531 | 1.00 | 26.31 |
| 955 | NH2 | ARG | 131 | 7.201 | −5.189 | 49.949 | 1.00 | 26.33 |
| 956 | C | ARG | 131 | 10.865 | −7.967 | 43.300 | 1.00 | 24.35 |
| 957 | O | ARG | 131 | 11.130 | −9.064 | 42.806 | 1.00 | 24.95 |
| 958 | N | GLY | 132 | 11.673 | −6.917 | 43.215 | 1.00 | 24.52 |
| 959 | CA | GLY | 132 | 12.954 | −7.020 | 42.546 | 1.00 | 24.41 |
| 960 | C | GLY | 132 | 13.016 | −6.358 | 41.183 | 1.00 | 24.47 |
| 961 | O | GLY | 132 | 14.109 | −6.127 | 40.664 | 1.00 | 24.98 |
| 962 | N | GLN | 133 | 11.866 | −6.029 | 40.603 | 1.00 | 24.01 |
| 963 | CA | GLN | 133 | 11.840 | −5.414 | 39.280 | 1.00 | 24.09 |
| 964 | CB | GLN | 133 | 10.650 | −5.964 | 38.485 | 1.00 | 25.36 |
| 965 | CG | GLN | 133 | 10.490 | −7.481 | 38.581 | 1.00 | 27.91 |
| 966 | CD | GLN | 133 | 9.305 | −7.997 | 37.785 | 1.00 | 29.24 |
| 967 | OE1 | GLN | 133 | 8.879 | −9.140 | 37.957 | 1.00 | 30.80 |
| 968 | NE2 | GLN | 133 | 8.770 | −7.158 | 36.906 | 1.00 | 30.42 |
| 969 | C | GLN | 133 | 11.798 | −3.880 | 39.267 | 1.00 | 23.46 |
| 970 | O | GLN | 133 | 12.546 | −3.239 | 38.524 | 1.00 | 23.29 |
| 971 | N | MET | 134 | 10.931 | −3.290 | 40.085 | 1.00 | 22.84 |
| 972 | CA | MET | 134 | 10.794 | −1.836 | 40.116 | 1.00 | 22.46 |
| 973 | CB | MET | 134 | 9.330 | −1.463 | 40.381 | 1.00 | 22.33 |
| 974 | CG | MET | 134 | 8.329 | −2.175 | 39.480 | 1.00 | 22.57 |
| 975 | SD | MET | 134 | 8.509 | −1.770 | 37.735 | 1.00 | 22.72 |
| 976 | CE | MET | 134 | 6.809 | −2.014 | 37.162 | 1.00 | 23.57 |
| 977 | C | MET | 134 | 11.680 | −1.161 | 41.155 | 1.00 | 22.47 |
| 978 | O | MET | 134 | 12.193 | −1.805 | 42.069 | 1.00 | 22.23 |
| 979 | N | GLN | 135 | 11.867 | .145 | 40.998 | 1.00 | 22.42 |
| 980 | CA | GLN | 135 | 12.670 | .901 | 41.946 | 1.00 | 22.64 |
| 981 | CB | GLN | 135 | 12.683 | 2.382 | 41.574 | 1.00 | 23.26 |
| 982 | CG | GLN | 135 | 13.270 | 2.615 | 40.192 | 1.00 | 25.02 |
| 983 | CD | GLN | 135 | 13.510 | 4.077 | 39.867 | 1.00 | 26.07 |
| 984 | OE1 | GLN | 135 | 13.288 | 4.510 | 38.735 | 1.00 | 27.62 |
| 985 | NE2 | GLN | 135 | 13.982 | 4.840 | 40.845 | 1.00 | 26.79 |
| 986 | C | GLN | 135 | 12.040 | .673 | 43.310 | 1.00 | 22.39 |
| 987 | O | GLN | 135 | 10.815 | .698 | 43.449 | 1.00 | 21.57 |
| 988 | N | LYS | 136 | 12.877 | .445 | 44.310 | 1.00 | 21.82 |
| 989 | CA | LYS | 136 | 12.401 | .143 | 45.652 | 1.00 | 22.11 |
| 990 | CB | LYS | 136 | 13.565 | .175 | 46.640 | 1.00 | 23.42 |
| 991 | CG | LYS | 136 | 13.260 | −.609 | 47.893 | 1.00 | 25.21 |
| 992 | CD | LYS | 136 | 12.851 | −2.034 | 47.540 | 1.00 | 26.76 |
| 993 | CE | LYS | 136 | 12.573 | −2.843 | 48.787 | 1.00 | 28.18 |
| 994 | NZ | LYS | 136 | 13.821 | −2.976 | 49.592 | 1.00 | 29.70 |
| 995 | C | LYS | 136 | 11.232 | .948 | 46.214 | 1.00 | 21.09 |
| 996 | O | LYS | 136 | 10.268 | .373 | 46.704 | 1.00 | 21.01 |
| 997 | N | PRO | 137 | 11.302 | 2.291 | 46.167 | 1.00 | 20.21 |
| 998 | CD | PRO | 137 | 12.365 | 3.166 | 45.647 | 1.00 | 20.15 |
| 999 | CA | PRO | 137 | 10.193 | 3.083 | 46.716 | 1.00 | 19.51 |
| 1000 | CB | PRO | 137 | 10.629 | 4.523 | 46.449 | 1.00 | 19.89 |
| 1001 | CG | PRO | 137 | 12.127 | 4.428 | 46.429 | 1.00 | 20.23 |
| 1002 | C | PRO | 137 | 8.868 | 2.759 | 46.020 | 1.00 | 18.62 |
| 1003 | O | PRO | 137 | 7.817 | 2.672 | 46.661 | 1.00 | 18.20 |
| 1004 | N | PHE | 138 | 8.938 | 2.595 | 44.707 | 1.00 | 17.72 |
| 1005 | CA | PHE | 138 | 7.768 | 2.274 | 43.901 | 1.00 | 17.29 |
| 1006 | CB | PHE | 138 | 8.139 | 2.291 | 42.417 | 1.00 | 17.12 |
| 1007 | CG | PHE | 138 | 6.953 | 2.201 | 41.496 | 1.00 | 17.38 |
| 1008 | CD1 | PHE | 138 | 6.373 | 3.355 | 40.974 | 1.00 | 16.83 |
| 1009 | CD2 | PHE | 138 | 6.394 | .967 | 41.178 | 1.00 | 16.68 |
| 1010 | CE1 | PHE | 138 | 5.250 | 3.281 | 40.149 | 1.00 | 17.12 |
| 1011 | CE2 | PHE | 138 | 5.271 | .879 | 40.354 | 1.00 | 17.47 |
| 1012 | CZ | PHE | 138 | 4.696 | 2.039 | 39.838 | 1.00 | 17.04 |
| 1013 | C | PHE | 138 | 7.274 | .885 | 44.285 | 1.00 | 16.99 |
| 1014 | O | PHE | 138 | 6.086 | .667 | 44.492 | 1.00 | 16.19 |
| 1015 | N | GLU | 139 | 8.208 | −.058 | 44.362 | 1.00 | 17.23 |
| 1016 | CA | GLU | 139 | 7.889 | −1.432 | 44.718 | 1.00 | 18.00 |
| 1017 | CB | GLU | 139 | 9.166 | −2.282 | 44.707 | 1.00 | 19.53 |
| 1018 | CG | GLU | 139 | 8.970 | −3.704 | 45.210 | 1.00 | 21.62 |
| 1019 | CD | GLU | 139 | 10.276 | −4.473 | 45.287 | 1.00 | 22.41 |
| 1020 | OE1 | GLU | 139 | 10.939 | −4.611 | 44.243 | 1.00 | 23.16 |
| 1021 | OE2 | GLU | 139 | 10.636 | −4.936 | 46.391 | 1.00 | 23.77 |
| 1022 | C | GLU | 139 | 7.237 | −1.505 | 46.099 | 1.00 | 17.75 |
| 1023 | O | GLU | 139 | 6.179 | −2.111 | 46.258 | 1.00 | 17.76 |
| 1024 | N | ASP | 140 | 7.860 | −.882 | 47.095 | 1.00 | 17.78 |
| 1025 | CA | ASP | 140 | 7.305 | −.922 | 48.446 | 1.00 | 17.66 |
| 1026 | CB | ASP | 140 | 8.205 | −.178 | 49.438 | 1.00 | 18.48 |
| 1027 | CG | ASP | 140 | 9.500 | −.922 | 49.724 | 1.00 | 20.16 |
| 1028 | OD1 | ASP | 140 | 9.547 | −2.146 | 49.487 | 1.00 | 20.57 |
| 1029 | OD2 | ASP | 140 | 10.465 | −.285 | 50.198 | 1.00 | 20.81 |
| 1030 | C | ASP | 140 | 5.893 | −.356 | 48.512 | 1.00 | 17.24 |
| 1031 | O | ASP | 140 | 5.028 | −.928 | 49.174 | 1.00 | 16.78 |
| 1032 | N | ALA | 141 | 5.655 | .756 | 47.822 | 1.00 | 16.59 |
| 1033 | CA | ALA | 141 | 4.329 | 1.367 | 47.825 | 1.00 | 16.42 |
| 1034 | CB | ALA | 141 | 4.371 | 2.723 | 47.108 | 1.00 | 16.12 |
| 1035 | C | ALA | 141 | 3.310 | .446 | 47.152 | 1.00 | 16.18 |
| 1036 | O | ALA | 141 | 2.218 | .228 | 47.670 | 1.00 | 15.84 |
| 1037 | N | SER | 142 | 3.678 | −.109 | 46.004 | 1.00 | 16.24 |
| 1038 | CA | SER | 142 | 2.777 | −.991 | 45.267 | 1.00 | 16.71 |
| 1039 | CB | SER | 142 | 3.431 | −1.444 | 43.959 | 1.00 | 16.49 |
| 1040 | OG | SER | 142 | 3.743 | −.330 | 43.142 | 1.00 | 16.91 |
| 1041 | C | SER | 142 | 2.325 | −2.219 | 46.054 | 1.00 | 17.13 |
| 1042 | O | SER | 142 | 1.144 | −2.569 | 46.031 | 1.00 | 16.83 |
| 1043 | N | PHE | 143 | 3.258 | −2.879 | 46.738 | 1.00 | 17.55 |
| 1044 | CA | PHE | 143 | 2.911 | −4.069 | 47.506 | 1.00 | 18.32 |
| 1045 | CB | PHE | 143 | 4.152 | −4.939 | 47.748 | 1.00 | 18.72 |
| 1046 | CG | PHE | 143 | 4.538 | −5.785 | 46.563 | 1.00 | 18.96 |
| 1047 | CD1 | PHE | 143 | 5.342 | −5.272 | 45.550 | 1.00 | 19.25 |
| 1048 | CD2 | PHE | 143 | 4.058 | −7.087 | 46.441 | 1.00 | 19.32 |
| 1049 | CE1 | PHE | 143 | 5.663 | −6.042 | 44.429 | 1.00 | 19.01 |
| 1050 | CE2 | PHE | 143 | 4.372 | −7.865 | 45.328 | 1.00 | 19.64 |
| 1051 | CZ | PHE | 143 | 5.177 | −7.339 | 44.318 | 1.00 | 19.59 |
| 1052 | C | PHE | 143 | 2.213 | −3.769 | 48.827 | 1.00 | 18.37 |
| 1053 | O | PHE | 143 | 1.638 | −4.664 | 49.443 | 1.00 | 18.84 |
| 1054 | N | ALA | 144 | 2.247 | −2.510 | 49.254 | 1.00 | 18.17 |
| 1055 | CA | ALA | 144 | 1.597 | −2.112 | 50.498 | 1.00 | 17.95 |
| 1056 | CB | ALA | 144 | 2.399 | −1.000 | 51.182 | 1.00 | 18.19 |
| 1057 | C | ALA | 144 | .167 | −1.640 | 50.220 | 1.00 | 17.93 |
| 1058 | O | ALA | 144 | −.640 | −1.499 | 51.134 | 1.00 | 17.53 |
| 1059 | N | LEU | 145 | −.139 | −1.395 | 48.949 | 1.00 | 17.94 |
| 1060 | CA | LEU | 145 | −1.474 | −.953 | 48.559 | 1.00 | 18.09 |
| 1061 | CB | LEU | 145 | −1.440 | −.284 | 47.178 | 1.00 | 16.75 |
| 1062 | CG | LEU | 145 | −.837 | 1.111 | 46.984 | 1.00 | 15.85 |
| 1063 | CD1 | LEU | 145 | −.739 | 1.411 | 45.483 | 1.00 | 15.41 |
| 1064 | CD2 | LEU | 145 | −1.701 | 2.155 | 47.678 | 1.00 | 14.65 |
| 1065 | C | LEU | 145 | −2.447 | −2.123 | 48.490 | 1.00 | 19.06 |
| 1066 | O | LEU | 145 | −2.059 | −3.253 | 48.185 | 1.00 | 19.29 |
| 1067 | N | ARG | 146 | −3.713 | −1.845 | 48.776 | 1.00 | 20.08 |
| 1068 | CA | ARG | 146 | −4.751 | −2.863 | 48.687 | 1.00 | 21.58 |
| 1069 | CB | ARG | 146 | −5.877 | −2.568 | 49.683 | 1.00 | 23.06 |
| 1070 | CG | ARG | 146 | −5.442 | −2.667 | 51.143 | 1.00 | 25.52 |

TABLE 1-continued

| Atom # | Atom Type | Residue | # | X | Y | Z | OCC | B |
|---|---|---|---|---|---|---|---|---|
| 1071 | CD | ARG | 146 | −6.600 | −2.442 | 52.115 | 1.00 | 27.91 |
| 1072 | NE | ARG | 146 | −6.944 | −1.031 | 52.289 | 1.00 | 30.12 |
| 1073 | CZ | ARG | 146 | −6.149 | −.126 | 52.855 | 1.00 | 30.64 |
| 1074 | NH1 | ARG | 146 | −4.954 | −.478 | 53.306 | 1.00 | 31.21 |
| 1075 | NH2 | ARG | 146 | −6.551 | 1.136 | 52.977 | 1.00 | 30.51 |
| 1076 | C | ARG | 146 | −5.267 | −2.771 | 47.252 | 1.00 | 21.55 |
| 1077 | O | ARG | 146 | −5.127 | −1.728 | 46.611 | 1.00 | 21.50 |
| 1078 | N | THR | 147 | −5.845 | −3.850 | 46.736 | 1.00 | 21.82 |
| 1079 | CA | THR | 147 | −6.356 | −3.824 | 45.371 | 1.00 | 21.75 |
| 1080 | CB | THR | 147 | −6.987 | −5.173 | 44.977 | 1.00 | 22.35 |
| 1081 | OG1 | THR | 147 | −6.022 | −6.216 | 45.148 | 1.00 | 23.67 |
| 1082 | CG2 | THR | 147 | −7.432 | −5.150 | 43.517 | 1.00 | 22.54 |
| 1083 | C | THR | 147 | −7.397 | −2.721 | 45.235 | 1.00 | 21.57 |
| 1084 | O | THR | 147 | −8.273 | −2.568 | 46.093 | 1.00 | 21.33 |
| 1085 | N | GLY | 148 | −7.282 | −1.946 | 44.162 | 1.00 | 21.20 |
| 1086 | CA | GLY | 148 | −8.206 | −.852 | 43.922 | 1.00 | 21.52 |
| 1087 | C | GLY | 148 | −7.825 | .438 | 44.628 | 1.00 | 21.37 |
| 1088 | O | GLY | 148 | −8.462 | 1.470 | 44.421 | 1.00 | 21.83 |
| 1089 | N | GLU | 149 | −6.782 | .394 | 45.452 | 1.00 | 21.48 |
| 1090 | CA | GLU | 149 | −6.355 | 1.580 | 46.187 | 1.00 | 21.18 |
| 1091 | CB | GLU | 149 | −5.910 | 1.204 | 47.592 | 1.00 | 23.06 |
| 1092 | CG | GLU | 149 | −6.997 | .637 | 48.458 | 1.00 | 27.36 |
| 1093 | CD | GLU | 149 | −6.646 | .784 | 49.912 | 1.00 | 29.17 |
| 1094 | OE1 | GLU | 149 | −5.438 | .649 | 50.235 | 1.00 | 30.95 |
| 1095 | OE2 | GLU | 149 | −7.564 | 1.031 | 50.719 | 1.00 | 30.75 |
| 1096 | C | GLU | 149 | −5.250 | 2.390 | 45.528 | 1.00 | 19.76 |
| 1097 | O | GLU | 149 | −4.413 | 1.858 | 44.800 | 1.00 | 19.17 |
| 1098 | N | MET | 150 | −5.247 | 3.684 | 45.825 | 1.00 | 18.25 |
| 1099 | CA | MET | 150 | −4.277 | 4.609 | 45.262 | 1.00 | 17.36 |
| 1100 | CB | MET | 150 | −5.018 | 5.784 | 44.616 | 1.00 | 17.96 |
| 1101 | CG | MET | 150 | −4.147 | 6.714 | 43.792 | 1.00 | 18.98 |
| 1102 | SD | MET | 150 | −5.159 | 7.958 | 42.963 | 1.00 | 19.91 |
| 1103 | CE | MET | 150 | −5.513 | 9.037 | 44.338 | 1.00 | 20.33 |
| 1104 | C | MET | 150 | −3.291 | 5.117 | 46.309 | 1.00 | 16.27 |
| 1105 | O | MET | 150 | −3.628 | 5.282 | 47.484 | 1.00 | 15.78 |
| 1106 | N | SER | 151 | −2.062 | 5.355 | 45.871 | 1.00 | 15.57 |
| 1107 | CA | SER | 151 | −1.020 | 5.843 | 46.758 | 1.00 | 14.93 |
| 1108 | CB | SER | 151 | .361 | 5.460 | 46.221 | 1.00 | 15.00 |
| 1109 | OG | SER | 151 | .711 | 6.276 | 45.108 | 1.00 | 14.45 |
| 1110 | C | SER | 151 | −1.076 | 7.355 | 46.843 | 1.00 | 14.66 |
| 1111 | O | SER | 151 | −1.894 | 8.005 | 46.187 | 1.00 | 14.43 |
| 1112 | N | GLY | 152 | −.201 | 7.895 | 47.682 | 1.00 | 14.44 |
| 1113 | CA | GLY | 152 | −.060 | 9.329 | 47.813 | 1.00 | 14.23 |
| 1114 | C | GLY | 152 | 1.151 | 9.584 | 46.929 | 1.00 | 14.07 |
| 1115 | O | GLY | 152 | 1.486 | 8.719 | 46.117 | 1.00 | 13.85 |
| 1116 | N | PRO | 153 | 1.834 | 10.732 | 47.047 | 1.00 | 13.81 |
| 1117 | CD | PRO | 153 | 1.567 | 11.893 | 47.909 | 1.00 | 14.08 |
| 1118 | CA | PRO | 153 | 3.003 | 10.974 | 46.191 | 1.00 | 13.84 |
| 1119 | CB | PRO | 153 | 3.334 | 12.450 | 46.448 | 1.00 | 13.38 |
| 1120 | CG | PRO | 153 | 2.047 | 13.018 | 47.044 | 1.00 | 13.70 |
| 1121 | C | PRO | 153 | 4.161 | 10.057 | 46.577 | 1.00 | 14.03 |
| 1122 | O | PRO | 153 | 4.572 | 10.020 | 47.741 | 1.00 | 14.66 |
| 1123 | N | VAL | 154 | 4.675 | 9.314 | 45.600 | 1.00 | 14.71 |
| 1124 | CA | VAL | 154 | 5.797 | 8.404 | 45.828 | 1.00 | 14.79 |
| 1125 | CB | VAL | 154 | 5.437 | 6.959 | 45.409 | 1.00 | 15.18 |
| 1126 | CG1 | VAL | 154 | 6.634 | 6.032 | 45.607 | 1.00 | 15.52 |
| 1127 | CG2 | VAL | 154 | 4.247 | 6.470 | 46.236 | 1.00 | 14.82 |
| 1128 | C | VAL | 154 | 6.990 | 8.897 | 45.020 | 1.00 | 15.40 |
| 1129 | O | VAL | 154 | 6.890 | 9.104 | 43.809 | 1.00 | 14.90 |
| 1130 | N | PHE | 155 | 8.116 | 9.084 | 45.702 | 1.00 | 15.88 |
| 1131 | CA | PHE | 155 | 9.330 | 9.586 | 45.072 | 1.00 | 16.85 |
| 1132 | CB | PHE | 155 | 10.039 | 10.583 | 46.001 | 1.00 | 17.49 |
| 1133 | CG | PHE | 155 | 9.217 | 11.793 | 46.354 | 1.00 | 18.25 |
| 1134 | CD1 | PHE | 155 | 8.147 | 11.695 | 47.241 | 1.00 | 18.99 |
| 1135 | CD2 | PHE | 155 | 9.520 | 13.036 | 45.807 | 1.00 | 19.18 |
| 1136 | CE1 | PHE | 155 | 7.393 | 12.820 | 47.578 | 1.00 | 19.38 |
| 1137 | CE2 | PHE | 155 | 8.771 | 14.165 | 46.137 | 1.00 | 19.00 |
| 1138 | CZ | PHE | 155 | 7.707 | 14.054 | 47.024 | 1.00 | 19.28 |
| 1139 | C | PHE | 155 | 10.328 | 8.498 | 44.689 | 1.00 | 16.84 |
| 1140 | O | PHE | 155 | 10.687 | 7.658 | 45.511 | 1.00 | 17.06 |
| 1141 | N | THR | 156 | 10.769 | 8.526 | 43.435 | 1.00 | 17.24 |
| 1142 | CA | THR | 156 | 11.773 | 7.588 | 42.938 | 1.00 | 17.69 |
| 1143 | CB | THR | 156 | 11.190 | 6.512 | 42.009 | 1.00 | 17.45 |
| 1144 | OG1 | THR | 156 | 10.941 | 7.083 | 40.716 | 1.00 | 17.11 |
| 1145 | CG2 | THR | 156 | 9.903 | 5.939 | 42.592 | 1.00 | 17.57 |
| 1146 | C | THR | 156 | 12.748 | 8.410 | 42.106 | 1.00 | 18.21 |
| 1147 | O | THR | 156 | 12.569 | 9.615 | 41.941 | 1.00 | 17.61 |
| 1148 | N | ASP | 157 | 13.769 | 7.758 | 41.560 | 1.00 | 19.14 |
| 1149 | CA | ASP | 157 | 14.743 | 8.470 | 40.739 | 1.00 | 20.09 |
| 1150 | CB | ASP | 157 | 15.943 | 7.571 | 40.428 | 1.00 | 21.20 |
| 1151 | CG | ASP | 157 | 16.756 | 7.241 | 41.659 | 1.00 | 22.93 |
| 1152 | OD1 | ASP | 157 | 16.937 | 8.141 | 42.506 | 1.00 | 23.42 |
| 1153 | OD2 | ASP | 157 | 17.227 | 6.088 | 41.773 | 1.00 | 24.37 |
| 1154 | C | ASP | 157 | 14.133 | 8.971 | 39.434 | 1.00 | 19.98 |
| 1155 | O | ASP | 157 | 14.681 | 9.869 | 38.794 | 1.00 | 20.41 |
| 1156 | N | SER | 158 | 12.998 | 8.396 | 39.044 | 1.00 | 19.65 |
| 1157 | CA | SER | 158 | 12.327 | 8.786 | 37.807 | 1.00 | 19.83 |
| 1158 | CB | SER | 158 | 11.439 | 7.643 | 37.312 | 1.00 | 20.57 |
| 1159 | OG | SER | 158 | 12.219 | 6.492 | 37.041 | 1.00 | 23.13 |
| 1160 | C | SER | 158 | 11.491 | 10.048 | 37.972 | 1.00 | 19.02 |
| 1161 | O | SER | 158 | 11.217 | 10.757 | 36.999 | 1.00 | 18.55 |
| 1162 | N | GLY | 159 | 11.093 | 10.328 | 39.208 | 1.00 | 17.78 |
| 1163 | CA | GLY | 159 | 10.286 | 11.505 | 39.472 | 1.00 | 17.03 |
| 1164 | C | GLY | 159 | 9.286 | 11.207 | 40.569 | 1.00 | 16.43 |
| 1165 | O | GLY | 159 | 9.567 | 10.407 | 41.460 | 1.00 | 16.29 |
| 1166 | N | ILE | 160 | 8.121 | 11.844 | 40.507 | 1.00 | 15.62 |
| 1167 | CA | ILE | 160 | 7.084 | 11.637 | 41.512 | 1.00 | 14.89 |
| 1168 | CB | ILE | 160 | 6.565 | 12.983 | 42.066 | 1.00 | 14.36 |
| 1169 | CG2 | ILE | 160 | 5.645 | 12.739 | 43.259 | 1.00 | 14.26 |
| 1170 | CG1 | ILE | 160 | 7.747 | 13.854 | 42.495 | 1.00 | 14.60 |
| 1171 | CD1 | ILE | 160 | 7.355 | 15.255 | 42.946 | 1.00 | 14.29 |
| 1172 | C | ILE | 160 | 5.930 | 10.876 | 40.872 | 1.00 | 14.51 |
| 1173 | O | ILE | 160 | 5.481 | 11.224 | 39.781 | 1.00 | 15.18 |
| 1174 | N | HIS | 161 | 5.454 | 9.844 | 41.562 | 1.00 | 14.32 |
| 1175 | CA | HIS | 161 | 4.371 | 9.002 | 41.053 | 1.00 | 14.23 |
| 1176 | CB | HIS | 161 | 4.795 | 7.531 | 40.978 | 1.00 | 13.67 |
| 1177 | CG | HIS | 161 | 6.083 | 7.274 | 40.268 | 1.00 | 13.42 |
| 1178 | CD2 | HIS | 161 | 6.349 | 6.572 | 39.145 | 1.00 | 13.14 |
| 1179 | ND1 | HIS | 161 | 7.305 | 7.675 | 40.768 | 1.00 | 14.45 |
| 1180 | CE1 | HIS | 161 | 8.268 | 7.222 | 39.981 | 1.00 | 12.95 |
| 1181 | NE2 | HIS | 161 | 7.713 | 6.549 | 38.990 | 1.00 | 14.57 |
| 1182 | C | HIS | 161 | 3.113 | 8.968 | 41.906 | 1.00 | 14.30 |
| 1183 | O | HIS | 161 | 3.136 | 9.235 | 43.109 | 1.00 | 14.27 |
| 1184 | N | ILE | 162 | 2.021 | 8.589 | 41.250 | 1.00 | 13.69 |
| 1185 | CA | ILE | 162 | .743 | 8.347 | 41.902 | 1.00 | 14.50 |
| 1186 | CB | ILE | 162 | −.414 | 9.222 | 41.362 | 1.00 | 15.56 |
| 1187 | CG2 | ILE | 162 | −1.737 | 8.736 | 41.951 | 1.00 | 16.82 |
| 1188 | CG1 | ILE | 162 | −.196 | 10.687 | 41.749 | 1.00 | 16.35 |
| 1189 | CD1 | ILE | 162 | −1.233 | 11.644 | 41.171 | 1.00 | 16.45 |
| 1190 | C | ILE | 162 | .550 | 6.913 | 41.411 | 1.00 | 14.01 |
| 1191 | O | ILE | 162 | .600 | 6.665 | 40.206 | 1.00 | 14.21 |
| 1192 | N | ILE | 163 | .368 | 5.972 | 42.330 | 1.00 | 13.61 |
| 1193 | CA | ILE | 163 | .210 | 4.569 | 41.958 | 1.00 | 13.49 |
| 1194 | CB | ILE | 163 | 1.260 | 3.691 | 42.700 | 1.00 | 13.35 |
| 1195 | CG2 | ILE | 163 | 1.145 | 2.239 | 42.249 | 1.00 | 13.23 |
| 1196 | CG1 | ILE | 163 | 2.671 | 4.218 | 42.420 | 1.00 | 13.78 |
| 1197 | CD1 | ILE | 163 | 3.759 | 3.586 | 43.286 | 1.00 | 14.45 |
| 1198 | C | ILE | 163 | −1.180 | 4.012 | 42.263 | 1.00 | 13.81 |
| 1199 | O | ILE | 163 | −1.732 | 4.253 | 43.335 | 1.00 | 13.97 |
| 1200 | N | LEU | 164 | −1.743 | 3.273 | 41.310 | 1.00 | 13.55 |
| 1201 | CA | LEU | 164 | −3.048 | 2.643 | 41.498 | 1.00 | 13.95 |
| 1202 | CB | LEU | 164 | −4.055 | 3.124 | 40.445 | 1.00 | 14.06 |
| 1203 | CG | LEU | 164 | −5.422 | 2.418 | 40.500 | 1.00 | 14.34 |
| 1204 | CD1 | LEU | 164 | −6.142 | 2.783 | 41.794 | 1.00 | 14.67 |
| 1205 | CD2 | LEU | 164 | −6.255 | 2.811 | 39.291 | 1.00 | 14.93 |
| 1206 | C | LEU | 164 | −2.873 | 1.136 | 41.350 | 1.00 | 14.53 |
| 1207 | O | LEU | 164 | −2.492 | .662 | 40.284 | 1.00 | 14.17 |
| 1208 | N | ARG | 165 | −3.128 | .383 | 42.416 | 1.00 | 15.12 |
| 1209 | CA | ARG | 165 | −3.011 | −1.064 | 42.318 | 1.00 | 16.57 |
| 1210 | CB | ARG | 165 | −2.804 | −1.702 | 43.692 | 1.00 | 16.92 |
| 1211 | CG | ARG | 165 | −2.585 | −3.201 | 43.588 | 1.00 | 17.58 |
| 1212 | CD | ARG | 165 | −2.461 | −3.883 | 44.936 | 1.00 | 18.44 |
| 1213 | NE | ARG | 165 | −2.613 | −5.326 | 44.772 | 1.00 | 19.76 |
| 1214 | CZ | ARG | 165 | −2.697 | −6.197 | 45.772 | 1.00 | 20.62 |
| 1215 | NH1 | ARG | 165 | −2.638 | −5.777 | 47.028 | 1.00 | 20.16 |
| 1216 | NH2 | ARG | 165 | −2.864 | −7.490 | 45.511 | 1.00 | 19.98 |
| 1217 | C | ARG | 165 | −4.321 | −1.562 | 41.712 | 1.00 | 17.15 |
| 1218 | O | ARG | 165 | −5.395 | −1.313 | 42.252 | 1.00 | 17.41 |
| 1219 | N | THR | 166 | −4.225 | −2.256 | 40.587 | 1.00 | 18.06 |
| 1220 | CA | THR | 166 | −5.407 | −2.757 | 39.905 | 1.00 | 19.03 |
| 1221 | CB | THR | 166 | −5.322 | −2.487 | 38.392 | 1.00 | 18.87 |
| 1222 | OG1 | THR | 166 | −4.147 | −3.109 | 37.857 | 1.00 | 18.93 |

TABLE 1-continued

| Atom # | Atom Type | Residue | # | X | Y | Z | OCC | B |
|---|---|---|---|---|---|---|---|---|
| 1223 | CG2 | THR | 166 | −5.265 | −.992 | 38.123 | 1.00 | 19.36 |
| 1224 | C | THR | 166 | −5.606 | −4.249 | 40.115 | 1.00 | 19.82 |
| 1225 | O | THR | 166 | −6.648 | −4.797 | 39.762 | 1.00 | 19.31 |
| 1226 | N | GLU | 167 | −4.609 | −4.906 | 40.695 | 1.00 | 21.11 |
| 1227 | CA | GLU | 167 | −4.704 | −6.343 | 40.918 | 1.00 | 22.25 |
| 1228 | CB | GLU | 167 | −4.465 | −7.055 | 39.593 | 1.00 | 23.79 |
| 1229 | CG | GLU | 167 | −4.677 | −8.545 | 39.604 | 1.00 | 27.14 |
| 1230 | CD | GLU | 167 | −4.283 | −9.153 | 38.278 | 1.00 | 28.69 |
| 1231 | OE1 | GLU | 167 | −4.592 | −8.539 | 37.235 | 1.00 | 30.03 |
| 1232 | OE2 | GLU | 167 | −3.667 | −10.238 | 38.277 | 1.00 | 30.37 |
| 1233 | C | GLU | 167 | −3.684 | −6.816 | 41.945 | 1.00 | 21.79 |
| 1234 | O | GLU | 167 | −2.642 | −6.145 | 42.090 | 1.00 | 21.19 |
| 1235 | OT | GLU | 167 | −3.931 | −7.864 | 42.577 | 1.00 | 21.37 |
| 1236 | CB | TYR | 170 | 7.118 | 13.530 | 52.814 | 1.00 | 55.56 |
| 1237 | CG | TYR | 170 | 5.703 | 13.351 | 52.248 | 1.00 | 56.20 |
| 1238 | CD1 | TYR | 170 | 4.952 | 12.203 | 52.521 | 1.00 | 56.47 |
| 1239 | CE1 | TYR | 170 | 3.645 | 12.044 | 52.017 | 1.00 | 56.62 |
| 1240 | CD2 | TYR | 170 | 5.114 | 14.339 | 51.451 | 1.00 | 56.44 |
| 1241 | CE2 | TYR | 170 | 3.807 | 14.189 | 50.943 | 1.00 | 56.66 |
| 1242 | CZ | TYR | 170 | 3.081 | 13.043 | 51.231 | 1.00 | 56.70 |
| 1243 | OH | TYR | 170 | 1.793 | 12.904 | 50.754 | 1.00 | 57.13 |
| 1244 | C | TYR | 170 | 6.194 | 14.920 | 54.642 | 1.00 | 54.37 |
| 1245 | O | TYR | 170 | 5.970 | 13.961 | 55.356 | 1.00 | 54.42 |
| 1246 | N | TYR | 170 | 8.641 | 14.888 | 54.282 | 1.00 | 55.08 |
| 1247 | CA | TYR | 170 | 7.303 | 14.840 | 53.619 | 1.00 | 54.90 |
| 1248 | N | SEP | 171 | 5.893 | 16.138 | 54.270 | 1.00 | 53.40 |
| 1249 | CA | SEP | 171 | 4.911 | 16.155 | 55.342 | 1.00 | 52.46 |
| 1250 | CB | SEP | 171 | 4.976 | 17.400 | 56.248 | 1.00 | 53.58 |
| 1251 | OG | SEP | 171 | 5.418 | 17.088 | 57.603 | 1.00 | 55.25 |
| 1252 | C | SEP | 171 | 3.548 | 15.967 | 54.667 | 1.00 | 50.95 |
| 1253 | O | SEP | 171 | 3.041 | 16.860 | 53.999 | 1.00 | 50.72 |
| 1254 | P | SEP | 171 | 4.475 | 17.349 | 58.906 | 1.00 | 56.21 |
| 1255 | O1P | SEP | 171 | 5.346 | 17.261 | 60.120 | 1.00 | 56.25 |
| 1256 | O2P | SEP | 171 | 4.006 | 18.761 | 58.948 | 1.00 | 56.33 |
| 1257 | O3P | SEP | 171 | 3.279 | 16.493 | 58.749 | 1.00 | 56.44 |
| 1258 | N | PRO | 172 | 2.718 | 14.784 | 54.962 | 1.00 | 49.69 |
| 1259 | CD | PRO | 172 | 3.094 | 13.822 | 56.010 | 1.00 | 49.43 |
| 1260 | CA | PRO | 172 | 1.410 | 14.432 | 54.383 | 1.00 | 48.40 |
| 1261 | CB | PRO | 172 | 1.020 | 13.160 | 55.148 | 1.00 | 48.84 |
| 1262 | CG | PRO | 172 | 1.752 | 13.280 | 56.446 | 1.00 | 49.09 |
| 1263 | C | PRO | 172 | .290 | 15.467 | 54.378 | 1.00 | 47.21 |
| 1264 | O | PRO | 172 | .229 | 16.373 | 55.213 | 1.00 | 46.73 |
| 1265 | N | THR | 173 | −.610 | 15.312 | 53.417 | 1.00 | 45.94 |
| 1266 | CA | THR | 173 | −1.744 | 16.207 | 53.287 | 1.00 | 44.92 |
| 1267 | CB | THR | 173 | −1.980 | 16.579 | 51.817 | 1.00 | 45.05 |
| 1268 | CG1 | THR | 173 | −.722 | 16.601 | 51.131 | 1.00 | 45.35 |
| 1269 | CG2 | THR | 173 | −2.601 | 17.960 | 51.713 | 1.00 | 45.23 |
| 1270 | C | THR | 173 | −2.965 | 15.472 | 53.824 | 1.00 | 44.00 |
| 1271 | O | THR | 173 | −3.048 | 14.246 | 53.740 | 1.00 | 43.67 |
| 1272 | N | SEP | 174 | −3.901 | 16.219 | 54.394 | 1.00 | 43.11 |
| 1273 | CA | SEP | 174 | −5.107 | 15.613 | 54.928 | 1.00 | 42.34 |
| 1274 | CB | SEP | 174 | −5.982 | 16.661 | 55.613 | 1.00 | 41.77 |
| 1275 | OG | SEP | 174 | −5.285 | 17.278 | 56.677 | 1.00 | 40.78 |
| 1276 | C | SEP | 174 | −5.859 | 14.947 | 53.788 | 1.00 | 42.13 |
| 1277 | O | SEP | 174 | −5.803 | 15.405 | 52.648 | 1.00 | 42.16 |
| 1278 | P | SEP | 174 | −5.017 | 18.848 | 56.671 | 1.00 | 40.24 |
| 1279 | O1P | SEP | 174 | −3.939 | 19.053 | 57.657 | 1.00 | 39.89 |
| 1280 | O2P | SEP | 174 | −4.410 | 19.263 | 55.377 | 1.00 | 40.27 |
| 1281 | O3P | SEP | 174 | −6.331 | 19.526 | 56.783 | 1.00 | 40.16 |
| 1282 | N | PRO | 175 | −6.571 | 13.850 | 54.079 | 1.00 | 42.06 |
| 1283 | CD | PRO | 175 | −6.744 | 13.234 | 55.405 | 1.00 | 41.84 |
| 1284 | CA | PRO | 175 | −7.333 | 13.122 | 53.058 | 1.00 | 41.94 |
| 1285 | CB | PRO | 175 | −8.043 | 12.029 | 53.862 | 1.00 | 41.89 |
| 1286 | CG | PRO | 175 | −8.070 | 12.566 | 55.257 | 1.00 | 42.04 |
| 1287 | C | PRO | 175 | −8.289 | 13.969 | 52.217 | 1.00 | 42.11 |
| 1288 | O | PRO | 175 | −8.502 | 13.678 | 51.039 | 1.00 | 42.01 |
| 1289 | N | SER | 176 | −8.863 | 15.011 | 52.812 | 1.00 | 42.14 |
| 1290 | CA | SER | 176 | −9.777 | 15.887 | 52.081 | 1.00 | 42.14 |
| 1291 | CB | SER | 176 | −11.199 | 15.310 | 52.073 | 1.00 | 42.12 |
| 1292 | OG | SER | 176 | −11.820 | 15.434 | 53.340 | 1.00 | 41.96 |
| 1293 | C | SER | 176 | −9.791 | 17.273 | 52.709 | 1.00 | 42.33 |
| 1294 | O | SER | 176 | −9.105 | 17.452 | 53.738 | 1.00 | 42.23 |
| 1295 | OT | SER | 176 | −10.485 | 18.159 | 52.167 | 1.00 | 42.54 |
| 1296 | OH2 | WAT | 200 | 2.014 | 6.388 | 33.070 | 1.00 | 13.93 |
| 1297 | OH2 | WAT | 201 | −1.283 | −2.300 | 28.997 | 1.00 | 15.35 |
| 1298 | OH2 | WAT | 202 | −2.992 | −1.687 | 35.759 | 1.00 | 21.83 |
| 1299 | OH2 | WAT | 203 | −2.513 | 19.277 | 39.236 | 1.00 | 14.45 |
| 1300 | OH2 | WAT | 204 | −6.092 | 9.665 | 81.760 | 1.00 | 17.79 |
| 1301 | OH2 | WAT | 205 | 1.926 | 17.345 | 34.818 | 1.00 | 15.51 |
| 1302 | OH2 | WAT | 206 | −2.638 | .254 | 52.032 | 1.00 | 18.20 |
| 1303 | OH2 | WAT | 207 | 11.754 | 22.376 | 44.104 | 1.00 | 20.03 |
| 1304 | OH2 | WAT | 208 | 9.320 | −4.615 | 42.075 | 1.00 | 21.68 |
| 1305 | OH2 | WAT | 209 | 4.413 | 10.176 | 28.305 | 1.00 | 24.86 |
| 1306 | OH2 | WAT | 210 | 3.500 | 15.584 | 33.508 | 1.00 | 17.17 |
| 1307 | OH2 | WAT | 211 | 3.016 | −.603 | 29.684 | 1.00 | 16.24 |
| 1308 | OH2 | WAT | 212 | −3.433 | −.744 | 29.090 | 1.00 | 20.34 |
| 1309 | OH2 | WAT | 213 | −3.928 | 16.386 | 47.143 | 1.00 | 19.86 |
| 1310 | OH2 | WAT | 214 | −1.492 | 19.796 | 34.357 | 1.00 | 23.80 |
| 1311 | OH2 | WAT | 215 | 5.749 | 17.029 | 31.175 | 1.00 | 17.04 |
| 1312 | OH2 | WAT | 216 | −7.589 | 4.674 | 47.250 | 1.00 | 24.91 |
| 1313 | OH2 | WAT | 217 | 5.836 | −2.876 | 50.964 | 1.00 | 22.06 |
| 1314 | OH2 | WAT | 218 | 11.848 | 8.037 | 47.950 | 1.00 | 23.46 |
| 1315 | OH2 | WAT | 219 | 12.348 | 13.307 | 37.042 | 1.00 | 20.57 |
| 1316 | OH2 | WAT | 220 | −4.113 | 9.169 | 47.403 | 1.00 | 23.76 |
| 1317 | OH2 | WAT | 221 | 5.203 | 22.317 | 35.018 | 1.00 | 22.18 |
| 1318 | OH2 | WAT | 222 | 9.525 | 6.324 | 30.502 | 1.00 | 26.39 |
| 1319 | OH2 | WAT | 223 | −10.609 | 9.339 | 53.354 | 1.00 | 30.61 |
| 1320 | OH2 | WAT | 224 | −3.990 | 10.308 | 49.848 | 1.00 | 21.74 |
| 1321 | OH2 | WAT | 225 | 9.853 | 25.698 | 42.396 | 1.00 | 29.89 |
| 1322 | OH2 | WAT | 226 | −6.397 | 11.568 | 75.148 | 1.00 | 21.91 |
| 1323 | OH2 | WAT | 227 | 7.548 | 3.839 | 49.241 | 1.00 | 24.61 |
| 1324 | OH2 | WAT | 228 | −6.083 | 4.855 | 51.274 | 1.00 | 23.65 |
| 1325 | OH2 | WAT | 229 | −6.550 | 7.286 | 50.590 | 1.00 | 23.55 |
| 1326 | OH2 | WAT | 230 | .976 | 11.832 | 28.657 | 1.00 | 18.86 |
| 1327 | OH2 | WAT | 231 | −5.723 | 7.029 | 48.100 | 1.00 | 26.00 |
| 1328 | OH2 | WAT | 232 | 3.126 | 23.015 | 39.476 | 1.00 | 21.91 |
| 1329 | OH2 | WAT | 233 | −10.950 | 13.155 | 65.324 | 1.00 | 25.05 |
| 1330 | OH2 | WAT | 234 | −2.711 | 12.584 | 49.681 | 1.00 | 29.21 |
| 1331 | OH2 | WAT | 235 | 7.434 | −10.766 | 44.709 | 1.00 | 25.02 |
| 1332 | OH2 | WAT | 236 | −4.201 | 1.994 | 25.179 | 1.00 | 21.85 |
| 1333 | OH2 | WAT | 237 | −2.892 | 14.979 | 79.350 | 1.00 | 29.32 |
| 1334 | OH2 | WAT | 238 | 14.239 | 5.232 | 43.399 | 1.00 | 27.32 |
| 1335 | OH2 | WAT | 239 | −3.070 | −1.184 | 54.587 | 1.00 | 30.22 |
| 1336 | OH2 | WAT | 240 | −11.964 | 9.420 | 40.306 | 1.00 | 24.61 |
| 1337 | OH2 | WAT | 241 | −2.664 | 20.784 | 36.612 | 1.00 | 25.57 |
| 1338 | OH2 | WAT | 242 | 15.679 | .913 | 43.518 | 1.00 | 32.81 |
| 1339 | OH2 | WAT | 243 | 1.248 | −.885 | 54.817 | 1.00 | 24.39 |
| 1340 | OH2 | WAT | 244 | −8.178 | 4.883 | 76.583 | 1.00 | 24.66 |
| 1341 | OH2 | WAT | 245 | −6.075 | 15.256 | 48.229 | 1.00 | 27.33 |
| 1342 | OH2 | WAT | 246 | −4.529 | 1.584 | 33.651 | 1.00 | 26.47 |
| 1343 | OH2 | WAT | 247 | −1.823 | 14.652 | 48.096 | 1.00 | 27.21 |
| 1344 | OH2 | WAT | 248 | −10.286 | 7.153 | 39.164 | 1.00 | 24.26 |
| 1345 | OH2 | WAT | 249 | 8.150 | 8.218 | 48.429 | 1.00 | 23.48 |
| 1346 | OH2 | WAT | 250 | −8.406 | 2.586 | 77.882 | 1.00 | 25.81 |
| 1347 | OH2 | WAT | 251 | 13.368 | −6.143 | 46.515 | 1.00 | 38.51 |
| 1348 | OH2 | WAT | 252 | −.009 | 23.620 | 39.303 | 1.00 | 36.19 |
| 1349 | OH2 | WAT | 253 | −9.460 | 14.934 | 66.850 | 1.00 | 34.00 |
| 1350 | OH2 | WAT | 254 | −3.751 | 20.245 | 45.512 | 1.00 | 37.11 |
| 1351 | OH2 | WAT | 255 | 12.681 | 10.291 | 34.535 | 1.00 | 26.21 |
| 1352 | OH2 | WAT | 256 | 6.777 | .601 | 58.270 | 1.00 | 32.10 |
| 1353 | OH2 | WAT | 257 | 8.803 | 20.438 | 32.878 | 1.00 | 28.86 |
| 1354 | OH2 | WAT | 258 | .450 | 6.445 | 65.189 | 1.00 | 30.51 |
| 1355 | OH2 | WAT | 259 | −16.448 | 9.387 | 39.020 | 1.00 | 41.90 |
| 1356 | OH2 | WAT | 260 | 15.918 | 6.602 | 36.928 | 1.00 | 43.42 |
| 1357 | OH2 | WAT | 261 | −8.987 | 4.515 | 44.837 | 1.00 | 34.46 |
| 1358 | OH2 | WAT | 262 | 6.985 | 13.991 | 29.119 | 1.00 | 26.21 |
| 1359 | OH2 | WAT | 263 | −7.897 | −7.308 | 39.485 | 1.00 | 38.23 |
| 1360 | OH2 | WAT | 264 | 6.735 | 8.681 | 53.846 | 1.00 | 30.04 |
| 1361 | OH2 | WAT | 265 | −7.201 | 10.978 | 28.692 | 1.00 | 40.13 |
| 1362 | OH2 | WAT | 266 | −11.277 | 11.811 | 33.774 | 1.00 | 34.24 |
| 1363 | OH2 | WAT | 267 | −5.570 | 16.341 | 27.209 | 1.00 | 27.61 |
| 1364 | OH2 | WAT | 268 | 28.978 | 19.691 | 29.458 | 1.00 | 34.54 |
| 1365 | OH2 | WAT | 269 | −.394 | −3.182 | 56.909 | 1.00 | 37.28 |
| 1366 | OH2 | WAT | 270 | −5.901 | −6.275 | 48.732 | 1.00 | 38.98 |
| 1367 | OH2 | WAT | 271 | −5.314 | 13.550 | 50.350 | 1.00 | 28.96 |
| 1368 | OH2 | WAT | 272 | 17.572 | 7.657 | 45.251 | 1.00 | 37.08 |
| 1369 | OH2 | WAT | 273 | 1.725 | .998 | 23.015 | 1.00 | 41.72 |
| 1370 | OH2 | WAT | 274 | 14.327 | −4.819 | 37.245 | 1.00 | 37.09 |
| 1371 | OH2 | WAT | 275 | 6.276 | 11.721 | 57.649 | 1.00 | 47.33 |
| 1372 | OH2 | WAT | 276 | −15.076 | 17.669 | 59.792 | 1.00 | 40.97 |
| 1373 | OH2 | WAT | 277 | −.429 | −2.499 | 53.645 | 1.00 | 33.17 |
| 1374 | OH2 | WAT | 278 | 3.038 | −3.057 | 54.799 | 1.00 | 39.54 |

TABLE 1-continued

| Atom # | Atom Type | Residue | # | X | Y | Z | OCC | B |
|---|---|---|---|---|---|---|---|---|
| 1375 | OH2 | WAT | 279 | -3.954 | 9.216 | 72.671 | 1.00 | 39.85 |
| 1376 | OH2 | WAT | 280 | -10.200 | 1.398 | 41.849 | 1.00 | 42.94 |
| 1377 | OH2 | WAT | 281 | -10.292 | 3.217 | 52.063 | 1.00 | 43.76 |
| 1378 | OH2 | WAT | 282 | -15.225 | 12.071 | 60.987 | 1.00 | 45.57 |
| 1379 | OH2 | WAT | 283 | 4.001 | -4.280 | 52.274 | 1.00 | 29.89 |
| 1380 | OH2 | WAT | 284 | -8.055 | -8.627 | 42.074 | 1.00 | 41.79 |
| 1381 | OH2 | WAT | 285 | -1.008 | -6.151 | 62.404 | 1.00 | 46.22 |
| 1382 | OH2 | WAT | 286 | -9.176 | 10.031 | 51.259 | 1.00 | 36.18 |
| 1383 | OH2 | WAT | 287 | -3.447 | 5.807 | 27.025 | 1.00 | 39.54 |
| 1384 | OH2 | WAT | 288 | 6.178 | 1.935 | 27.972 | 1.00 | 41.27 |
| 1385 | OH2 | WAT | 289 | -.878 | 11.803 | 51.809 | 1.00 | 31.35 |
| 1386 | OH2 | WAT | 290 | 4.340 | .648 | 60.998 | 1.00 | 32.63 |
| 1387 | OH2 | WAT | 291 | 7.811 | -2.038 | 52.827 | 1.00 | 36.03 |
| 1388 | OH2 | WAT | 292 | -8.166 | 18.423 | 67.710 | 1.00 | 38.02 |
| 1389 | OH2 | WAT | 293 | -14.604 | 10.287 | 35.634 | 1.00 | 45.62 |
| 1390 | OH2 | WAT | 294 | -10.474 | 20.227 | 53.859 | 1.00 | 46.74 |
| 1391 | OH2 | WAT | 295 | 17.892 | 23.932 | 22.437 | 1.00 | 42.17 |
| 1392 | OH2 | WAT | 296 | 17.145 | 17.710 | 24.729 | 1.00 | 47.54 |
| 1393 | OH2 | WAT | 297 | 1.480 | 20.841 | 46.728 | 1.00 | 36.92 |
| 1394 | OH2 | WAT | 298 | -10.284 | 6.137 | 64.005 | 1.00 | 46.42 |
| 1395 | OH2 | WAT | 299 | 3.682 | 3.530 | 62.317 | 1.00 | 44.53 |
| 1396 | OH2 | WAT | 300 | -2.017 | -8.476 | 51.591 | 1.00 | 45.29 |
| 1397 | OH2 | WAT | 301 | -.106 | 11.221 | 83.869 | 1.00 | 37.74 |
| 1398 | OH2 | WAT | 302 | -8.555 | 9.470 | 27.344 | 1.00 | 50.52 |
| 1399 | OH2 | WAT | 303 | 6.694 | 27.979 | 40.780 | 1.00 | 40.54 |
| 1400 | OH2 | WAT | 304 | -9.496 | -4.420 | 47.793 | 1.00 | 40.89 |
| 1401 | OH2 | WAT | 305 | -15.396 | 11.041 | 56.150 | 1.00 | 44.20 |
| 1402 | OH2 | WAT | 306 | -5.928 | -11.415 | 43.389 | 1.00 | 48.32 |
| 1403 | OH2 | WAT | 307 | -10.479 | -7.663 | 44.866 | 1.00 | 52.88 |
| 1404 | OH2 | WAT | 308 | 14.262 | 4.179 | 49.470 | 1.00 | 46.97 |
| 1405 | OH2 | WAT | 309 | -.041 | 15.184 | 62.705 | 1.00 | 40.11 |
| 1406 | OH2 | WAT | 310 | 15.939 | 3.184 | 44.811 | 1.00 | 44.49 |
| 1407 | OH2 | WAT | 311 | 3.817 | -.929 | 63.168 | 1.00 | 42.13 |
| 1408 | OH2 | WAT | 312 | -10.174 | -.055 | 47.822 | 1.00 | 44.73 |
| 1409 | OH2 | WAT | 313 | 13.924 | -.156 | 50.669 | 1.00 | 43.49 |
| 1410 | OH2 | WAT | 314 | 4.943 | 21.521 | 46.064 | 1.00 | 33.15 |
| 1411 | OH2 | WAT | 315 | -4.990 | 11.627 | 72.769 | 1.00 | 42.40 |
| 1412 | OH2 | WAT | 316 | -8.733 | 15.608 | 48.610 | 1.00 | 49.94 |
| 1413 | OH2 | WAT | 317 | -7.762 | 17.938 | 49.355 | 1.00 | 40.62 |
| 1414 | OH2 | WAT | 318 | -4.978 | -.433 | 31.726 | 1.00 | 37.41 |
| 1415 | OH2 | WAT | 319 | -4.689 | 22.825 | 55.686 | 1.00 | 47.23 |
| 1416 | OH2 | WAT | 320 | 11.750 | -10.644 | 40.083 | 1.00 | 48.25 |
| 1417 | OH2 | WAT | 321 | -10.564 | 18.537 | 57.762 | 1.00 | 37.40 |
| 1418 | OH2 | WAT | 322 | 7.490 | 10.973 | 25.298 | 1.00 | 45.18 |
| 1419 | OH2 | WAT | 323 | 2.274 | 12.065 | 76.050 | 1.00 | 38.17 |
| 1420 | OH2 | WAT | 324 | -2.115 | 17.289 | 58.628 | 1.00 | 41.95 |
| 1421 | OH2 | WAT | 325 | 16.399 | 18.887 | 20.072 | 1.00 | 48.74 |
| 1422 | OH2 | WAT | 326 | 20.050 | 19.008 | 27.094 | 1.00 | 45.30 |
| 1423 | OH2 | WAT | 327 | -10.935 | -4.259 | 42.863 | 1.00 | 52.28 |
| 1424 | OH2 | WAT | 328 | -5.431 | -5.213 | 36.216 | 1.00 | 35.64 |
| 1425 | OH2 | WAT | 329 | -9.928 | 22.834 | 64.306 | 1.00 | 45.77 |
| 1426 | OH2 | WAT | 330 | -8.275 | 6.285 | 42.925 | 1.00 | 42.06 |
| 1427 | OH2 | WAT | 331 | -13.049 | 17.206 | 57.668 | 1.00 | 38.15 |
| 1428 | OH2 | WAT | 332 | 5.624 | -10.159 | 35.555 | 1.00 | 40.21 |
| 1429 | OH2 | WAT | 333 | 23.293 | 26.941 | 32.316 | 1.00 | 48.27 |
| 1430 | OH2 | WAT | 334 | 1.567 | .896 | 62.295 | 1.00 | 37.23 |
| 1431 | OH2 | WAT | 335 | -13.988 | -1.533 | 56.782 | 1.00 | 49.02 |
| 1432 | OH2 | WAT | 336 | 6.259 | 13.631 | 61.216 | 1.00 | 40.35 |
| 1433 | OH2 | WAT | 337 | -9.939 | -2.809 | 49.680 | 1.00 | 50.64 |
| 1434 | OH2 | WAT | 338 | -10.829 | 10.035 | 61.256 | 1.00 | 39.01 |
| 1435 | OH2 | WAT | 339 | 16.685 | 10.608 | 37.337 | 1.00 | 48.68 |
| 1436 | OH2 | WAT | 340 | -8.780 | .857 | 55.000 | 1.00 | 42.72 |
| 1437 | OH2 | WAT | 341 | -8.843 | -3.223 | 40.067 | 1.00 | 36.16 |
| 1438 | OH2 | WAT | 342 | .612 | 11.479 | 80.681 | 1.00 | 45.15 |
| 1439 | OH2 | WAT | 343 | 1.599 | -2.462 | 63.176 | 1.00 | 45.28 |
| 1440 | OH2 | WAT | 344 | 18.905 | 21.201 | 43.743 | 1.00 | 46.85 |
| 1441 | OH2 | WAT | 345 | 9.154 | -12.805 | 43.973 | 1.00 | 45.21 |
| 1442 | OH2 | WAT | 346 | -8.708 | 18.686 | 55.960 | 1.00 | 41.01 |
| 1443 | OH2 | WAT | 347 | -3.987 | -7.989 | 48.762 | 1.00 | 44.36 |
| 1444 | OH2 | WAT | 348 | -2.038 | -9.706 | 42.264 | 1.00 | 40.86 |
| 1445 | OH2 | WAT | 349 | -11.305 | 11.929 | 49.565 | 1.00 | 45.07 |
| 1446 | OH2 | WAT | 350 | 3.795 | 3.399 | 77.919 | 1.00 | 48.57 |
| 1447 | OH2 | WAT | 351 | 8.628 | 9.813 | 50.645 | 1.00 | 39.75 |

Note to Table 1 -
Coordinates from restrained individual B- factor refinement, refinement resolution: 62.017 – 1.840 A; starting r = .2597; free_r = .2866; final r = .2444; free_r = .2708; B rmsd for bonded mainchain atoms = .846; target = 1.5; B rmsd for bonded sidechain atoms = .985; target = 2.0; B rmsd for angle mainchain atoms = 1.551; target = 2.0; B rmsd for angle sidechain atoms = 1.623; target = 2.5; wa = 1.17512; rweight = .530173; target = mlf; steps = 30; space group = $P2_12_12_1$ (a = 35.270; b = 43.903; c = 124.659; $\alpha = \beta = \gamma = 90°$); B-correction resolution: 6.0 – 1.840; initial B-factor correction applied to fobs: B11 = -1.655; B22 = -3.389; B33 = 5.044; B12 = .000; B13 = .000; B23 = .000; B-factor correction applied to coordinate array B: 2.789; bulk solvent: density level = .377734 e/$A^3$; B-factor = 30.924 $A^2$ reflections with |Fobs|/sigma_F < 0.0 rejected reflections with |Fobs| > 10000 * rms(Fobs) rejected theoretical total number of reflections in resolution range: 17526 (100.0%) number of unobserved reflections (no entry or |F| = 0): 419 (2.4%) number of reflections rejected: 0(0.0%) total number of reflections used: 17107 (97.6%) number of reflections in working set: 16241 (92.7%); number of reflections in test set: 866 (4.9%) CRYST1 35.270 43.903 124.659 90.00 90.00 90.00 P 21 21 21.

The human Pin1 numbering sequence differs from that above due to the addition of four residues at the N-terminus from the *E. coli* cloning/expression vector. Thus, one should add 4 to the native human Pin1 sequence to arrive at the numbering scheme above. For instance, Trp11 of the original sequence is now Trp15 above.

In addition, in accordance with this invention, WW domains, Pin1 WW domains, or Pin1 WW domain mutants may be crystallized in co-complex with known WW domain binding agents, substrates, or inhibitors. The crystal structures of a series of such complexes may then be solved by molecular replacement and compared with that of a wild-type WW domain. Potential sites for modification within the various binding sites of the WW domain may thus be identified. This information provides an additional tool for determining the most efficient binding interactions, for example, increased hydrophobic interactions, between a WW domain and a chemical entity or compound.

All of the complexes referred to above may be studied using well-known X-ray diffraction techniques and may be refined versus 2–3 Å resolution X-ray data to an R value of about 0.20 or less using computer software, such as X-PLOR (Yale University, 1992, distributed by Molecular Simulations, Inc.). See, e.g., Blundel & Johnson, supra; Methods in Enzymology, vol. 114 and 115, H. W. Wyckoff et al., eds., Academic Press (1985). This information may thus be used to optimize known classes of WW domain binding agents (e.g., inhibitors), and to design and synthesize novel classes of WW domain binding agents (e.g., inhibitors).

The design of binding agents that bind or otherwise associate with or inhibit a WW domain according to the invention generally involves consideration of two factors. First, the compound or binding agent must be capable of physically and structurally associating with a WW domain. Non-covalent molecular interactions important in the association of a WW domain with a substrate include hydrogen bonding, van der Waals and hydrophobic interactions.

Second, the compound or binding agent must be able to assume a conformation that allows it to associate with a WW domain. Although certain portions of the compound or binding agent will not directly participate in this association, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of a WW domain (e.g., a Pin1 WW domain), or the spacing between functional groups of a compound comprising several chemical entities that directly interact with a WW domain.

The potential inhibitory or binding effect of a chemical compound on a WW domain may be analyzed prior to its actual synthesis and testing by the use of computer modeling techniques. If the theoretical structure of the given compound suggests insufficient interaction and association between it and a WW domain, synthesis and testing of the compound may be obviated. However, if computer modeling indicates a strong interaction, the molecule may then be tested for its ability to bind to a WW domain. Methods of assaying for WW domain activity are known in the art. Methods for assaying the effect of a potential binding agent can be performed in the presence of a known binding agent of a WW domain. For example, the effect of the potential binding agent can be assayed by measuring the ability of the potential binding agent to compete with a known binding agent.

An inhibitory or other binding compound of a WW domain may be computationally evaluated and designed by means of a series of steps in which chemical entities or fragments are screened and selected for their ability to associate with the individual binding pockets or other areas of a WW domain.

One skilled in the art may use one of several methods to screen chemical entities or fragments for their ability to associate with a WW domain and more particularly with the individual binding pockets of the WW domain of Pin1. This process may begin by visual inspection of, for example, the active site on the computer screen based on the Pin1 WW domain coordinates in Table 1. Selected fragments or chemical entities may then be positioned in a variety of orientations, or docked, within an individual binding pocket of a WW domain. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. These include:

1. GRID (Goodford, P. J., "A Computational Procedure for Determining Energetically Favorable Binding Sites on Biologically Important Macromolecules", J. Med. Chem., 28, pp. 849–857 (1985)). GRID is available from Oxford University, Oxford, UK.

2. MCSS (Miranker, A. and M. Karplus, "Functionality Maps of Binding Sites: A Multiple Copy Simultaneous Search Method." Proteins: Structure. Function and Genetics, 11, pp. 29–34 (1991)). MCSS is available from Molecular Simulations, Burlington, Mass.

3. AUTODOCK (Goodsell, D. S. and A. J. Olsen, "Automated Docking of Substrates to Proteins by Simulated Annealing", Proteins: Structure. Function, and Genetics, 8, pp. 195–202 (1990)). AUTODOCK is available from Scripps Research Institute, La Jolla, Calif.

4. DOCK (Kuntz, I. D. et al, "A Geometric Approach to Macromolecule-Ligand Interactions", J. Mol. Biol., 161, pp. 269–288 (1982)). DOCK is available from University of California, San Francisco, Calif.

Once suitable chemical entities or fragments have been selected, they can be assembled into a single compound or binding agent (e.g., an inhibitor). Assembly may be performed by visual inspection of the relationship of the fragments to each other on the three-dimensional image displayed on a computer screen in relation to the structure coordinates of the Pin1 WW domain as set forth in Table 1. This would be followed by manual model building using software such as Quanta or Sybyl.

Useful programs to aid one of skill in the art in connecting the individual chemical entities or fragments include:

1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., Royal Chem. Soc., 78, pp. 182–196 (1989)). CAVEAT is available from the University of California, Berkeley, Calif.

2. 3D Database systems such as MACCS-3D (MDL Information Systems, San Leandro, Calif.). This area is reviewed in Martin, Y. C., "3D Database Searching in Drug Design", J. Med. Chem., 35, pp. 2145–2154 (1992)).

3. HOOK (available from Molecular Simulations, Burlington, Mass.).

In addition to the method of building or identifing a WW domain binding agent in a step-wise fashion one fragment or chemical entity at a time as described above, inhibitory or other WW domain binding compounds may be designed as a whole or "de novo" using either an empty active site or optionally including some portion(s) of a known inhibitor(s). These methods include:

1. LUDI (Bohm, H.-J., "The Computer Program LUDI. A New Method for the De Novo Design of Enzyme Inhibitors", J. Comp. Aid. Molec. Design, 6, pp. 61–78 (1992)). LUDI is available from Biosym Technologies, San Diego, Calif.

2. LEGEND (Nishibata, Y. and A. Itai, Tetrahedron, 47, p. 8985 (1991)). LEGEND is available from Molecular Simulations, Burlington, Mass.

3. LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry", J. Med. Chem., 33, pp. 883–894 (1990). See also, Navia, M. A. and M. A. Murcko, "The Use of Structural Information in Drug Design", Current Opinions in Structural Biology, 2, pp. 202–210 (1992).

Once a compound or binding agent has been designed or selected by the above methods, the efficiency with which that compound may bind to a WW domain may be tested and optimized by computational evaluation.

A compound designed or selected as a WW domain binding agent may be further computationally optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the binding agent and the WW domain when the binding agent is bound to the WW domain, preferably make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa., 1992); AMBER, version 4.0 (P. A.

Kollman, University of California at San Francisco, 1994); QUANTA/CHARMM (Molecular Simulations, Inc., Burlington, Mass. 1994); and Insight II/Discover (Biosysm Technologies Inc., San Diego, Calif., 1994). These programs may be implemented, for example, using a Silicon Graphics workstation, IRIS 4D/35 or IBM RISC/6000 workstation model 550. Other hardware systems and software packages will be known to those skilled in the art of which the speed and capacity are continually modified.

Once a WW domain binding agent has been selected or designed, as described above, substitutions may then be made in some of its atoms or side groups in order to improve or modify its binding properties. Generally, initial substitutions are conservative, e.g., the replacement group will have approximately the same size, shape, hydrophobicity and charge as the original group. Such substituted chemical compounds may then be analyzed for efficiency of fit to a WW domain by the same computer methods described above.

A further aspect of the invention encompasses methods of treatment using inhibitors or binding agents of a WW domain. The WW domain activity has been associated with a number of diseases including, for example, hypertension and muscular dystrophy (Staub and Rotin, Structure 4(5): 495–9, 1996); and breast cancer (Bednarak et al., Cancer Res., 60(8):2140–5, 2000).

Cell proliferative disorders contemplated for treatment using the invention compounds and methods disclosed herein include disorders characterized by unwanted, inappropriate or uncontrolled cell growth. Particular examples include cancer, fibrotic disorders, non-neoplastic growths such as benign prostatic hypertrophy, endometriosis, psoriasis, and the like. Cancers contemplated for treatment in accordance with the present invention include both solid tumors and hematopoeitic cancers such as leukemias and lymphomas.

Solid tumors that are treatable utilizing the invention compounds and methods include carcinomas, sarcomas, osteomas, fibrosarcomas, chondrosarcomas, and the like. Specific cancers contemplated for treatment include breast cancer, brain cancer, lung cancer (non-small cell and small cell), colon cancer, pancreatic cancer, prostate cancer, gastric cancer, bladder cancer, kidney cancer, head and neck cancer, and the like.

Fibrotic disorders are generally characterized by inappropriate overproliferation of non-cancerous fibroblasts. Examples include fibromyalgia, fibrosis (cystic, hepatic, idopathic pulmonary, pericardial, and the like), cardiac fibromas, fibromuscular hyperplasia, restenosis, atherosclerosis, fibromyositis, and the like.

Invention compounds are additionally useful in inhibiting mitosis in pathogenic organisms and are, therefore, useful for treating infectious diseases. Particular infectious diseases treatable by the methods disclosed herein include bacterial infections and fungal infections.

Bacterial infections contemplated for treatment using invention compounds and methods include infections caused by both gram-positive and gram-negative bacteria, including infections caused by *Staphylococcus, Clostridium, Streptococcus, Enterococcus, Diplococcus, Hemophilus, Neisseria, Erysipelothricosis, Listeria, Bacillus, Salmonella, Shigella, Escherichia, Klebsiella, Enterobacter, Serratia, Proteus, Morganella, Providencia, Yersinia, Camphylobacter, Mycobacteria*, and the like. Infection by such organisms causes a wide variety of disorders including pneumonia, diarrhea and dysentery, anthrax, rheumatic fever, toxic shock syndrome, mastoiditis, meningitis, gonorrhea, typhoid fever, gastroenteritis, brucellosis, cholera, bubonic plague, tetanus, tuberculosis, Lyme disease, and the like.

Fungal infections contemplated for treatment using invention compounds and methods include systemic fungal infections, dermatophytoses and fungal infections of the genitourinary tract. Systemic fungal infections include those caused by *Histoplasma, Coccidioides, Cryptococcus, Blastocyces, Paracoccidioides, Candida, Aspergillus, Nocardia, Sporothrix, Rhizopus, Absidia, Mucor, Hormodendrum, Phialophora, Rhinosporidium*, and the like. Dermatophyte infections include those caused by *Microsporum, Trichophyton, Epidermophyton, Candida, Pityrosporum*, and the like. Fungal disorders of the genito-urinary tract include infections caused by *Candida, Cryptococcus, Aspergillus, Zygomycodoides*, and the like. Infection by such organisms causes a wide variety of disorders such as ringworm, thrush, San Joaquin fever or Valley fever, Gilcrist's disease, and the like. These infections can be particularly serious, and even fatal, in patients with a depressed immune system such as organ transplant recipients and persons with acquired immunodefficiency syndrome (AIDS).

In a further aspect of the invention, invention compounds may be used as insecticides. The compounds of the invention prevent mitosis in insect cells, and thus can be used to control the growth and proliferation of a variety of insect pests. This aspect of the invention has important applications in agriculture, such as in the field, in the storage of agricultural products, and the like. Additionally, invention compounds are useful for controlling insect populations in places inhabited by man, such as homes, offices, and the like.

The particular invention compound(s) selected for therapeutic use as taught herein can be administered to a subject either alone or in a pharmaceutical composition where the compound(s) is mixed with suitable carriers or excipient(s). In treating a subject, a therapeutically effective dose of compound (i.e., active ingredient) is administered. A therapeutically effective dose refers to that amount of the active ingredient that produces amelioration of symptoms or a prolongation of survival of a subject.

Toxicity and therapeutic efficacy of a compound can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Compounds which exhibit large therapeutic indices are preferred. The data obtained from these cell culture assays and animal studies can be used in formulating a range of dosages suitable for use in humans. The dosage of such compounds lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like.

For any compound used in the method of the invention, the therapeutically effective dose can be estimated initially from cell culture assays by determining an $IC_{50}$ (i.e., the concentration of the test substance which achieves a half-maximal inhibition of PPIase activity). A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition. (See e.g. Fingl et al., 1975, in "The Pharmacological Basis of Therapeutics", Ch. 1 pl).

It should be noted that the attending physician would know how to and when to terminate, interrupt, or adjust administration due to toxicity, to organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient. Typically, the dose will be between about 1–10 mg/kg of body weight. About 1 mg to about 50 mg will be administered to a child, and between about 25 mg and about 1000 mg will be administered to an adult. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed into dosages suitable for systemic administration is within the scope of the invention. With proper choice of carrier and suitable manufacturing practice, the compositions of the present invention, in particular those formulated as solutions, may be administered parenterally, such as by intravenous injection. The compounds can be readily formulated using pharmaceutically acceptable carriers well known in the art into dosages suitable for oral administration. Such carriers enable the compounds of the invention to be formulated as tablets, pills, capsules, dragees, liquids, gels, syrups, slurries, suspensions and the like, for oral ingestion by a subject to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Delivery systems involving liposomes are discussed in International Patent Publication No. WO 91/02805 and International Patent Publication No. WO 91/19501, as well as U.S. Pat. No. 4,880,635 to Janoff et al. These publications and patents provide useful descriptions of techniques for liposome drug delivery and are incorporated by reference herein in their entirety.

Pharmaceutical compositions contemplated for use in the present invention include compositions wherein the active ingredients are contained in an amount effective to achieve the intended purpose. Determination of an effective amount is well within the capability of those skilled in the art, especially in light of the detailed disclosure provided herein.

In addition to the active ingredients, these pharmaceutical compositions may contain suitable pharmaceutically acceptable excipients and auxiliaries which facilitate processing of the active compounds into preparations which can be used pharmaceutically.

The pharmaceutical compositions of the present invention may be manufactured in a manner that is itself known, e.g., by means of conventional mixing, dissolving, granulating, dragee-making, levigating, emulsifying, encapsulating, entrapping, lyophilizing processes, or the like.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding the resulting mixture, and processing the mixture of granules, after adding suitable auxiliaries, if desired, to obtain tablets or dragee cores.

Suitable excipients are, in particular, fillers such as sugars, including lactose, sucrose, mannitol, sorbitol, and the like; cellulose preparations such as, for example, maize starch, wheat starch, rice starch, potato starch, gelatin, gum tragacanth, methyl cellulose, hydroxypropylmethylcellulose, sodium carboxymethylcellulose, polyvinylpyrrolidone (PVP), and the like, as well as mixtures of any two or more thereof. If desired, disintegrating agents may be added, such as cross-linked polyvinyl pyrrolidone, agar, alginic acid or a salt thereof such as sodium alginate, and the like.

Dragee cores are provided with suitable coatings. For this purpose, concentrated sugar solutions may be used, which may optionally contain gum arabic, talc, polyvinyl pyrrolidone, carbopol gel, polyethylene glycol, titanium dioxide, lacquer solutions, suitable organic solvents or solvent mixtures, and the like. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The invention will now be described in greater detail by reference to the following non-limiting examples.

EXAMPLES

Protein purification and crystallography. His8-tagged Pin1 was expressed and purified by $Ni^{+2}$-chelation chromatography, the histidine tag was removed by thrombin digestion, and the protein purified as described in Ranganathan et al., Cell 89:875–886, 1997. All site-directed mutants were constructed using the QuikChange (Stratagene) protocol and purified like wild type Pin1. Crystals of the Pin1-YpSPTpSPS complex were grown in hanging drops at 4° C. by mixing 1.0 μl of the Pin1-peptide complex with 1.0 μl of a reservoir solution containing 100 mM MOPSO-$Na^+$ (pH 7.0), 28% (v/v) PEG 8000, 2 mM DTT, stabilized in 100 mM MOPSO-$Na^+$ (pH 7.0), 25% (v/v) PEG 8000, 20% (v/v) glycerol, 1 mM DTT, and rapidly frozen in a 100 K stream of nitrogen gas. A native data set extending to 1.84 Å resolution was collected at the Stanford Synchrotron Radiation Laboratory, beamline 9-1 ($\lambda$=0.98 Å). Data were processed with DENZO and scaled with SCALEPACK (Otwinowski, Z., Minor, W. Meth. Enzymol. 276:307–326, 1997). The crystals contain one Pin1-peptide complex per asymmetric unit and belong to space group $P2_12_12_1$ (a=35.27 Å, b=43.90 Å, c=124.66 Å, $\alpha=\beta=\gamma=90°$). The final data set with an overall R merge of 6.2% (R merge=33.7% in the highest resolution shell) is 97.3% complete (98.2% in the highest resolution shell) for the resolution range of 62.02 Å to 1.84 Å. The structure of the Pin1-YpSPTpSPS repeat complex was solved by molecular replacement with AMORE (Navaza, J. Acta Crystallogr. A 50:157–163, 1994) using the Pin1 monomer as a starting model (Ranganathan et al., Cell 89:875–886, 1997). The resulting model was then positionally refined against all the data between 62.02 Å and 1.84 Å using the default bulk solvent model in CNS with maximum likelihood targets (Brunger et al., Acta Crystallogr. D 54:905–921, 1998). After refining the rebuilt model, water molecules were added automatically using CNS and edited manually in O. The final positional refinement converged to a crystallographic R factor of 24% (R free=27%) for all data (17107 reflections) between 62.02 Å and 1.84 Å. This model consists of residues 1 to 38 and 51 to 163 of human Pin1, the entire phosphopeptide, and 151 water molecules. Model quality was checked with PROCHECK (Laskowski et al., J. Appl. Crystallogr. 26:283–291, 1993). A total of 91.7% of the residues are in the most favored regions of the Ramachandran plot, 6.8% in the additional allowed region, and 0.8% in the generously allowed region. Glu-5 borders the generously allowed region.

Binding Analysis. To determine the affinity of full length Pin1 and its isolated PPIase and WW domains for a set of rhodamine-labeled peptides as shown in Table 2, were obtained commercially (SynPep Corporation, Dublin, Calif.) and allowed to interact with Pin1, PPIase and WW domains. These peptides were derived from proteins previously shown to interact with Pin1. While the set of peptides examined is limited, a consensus emerges from comparison of the highest affinity interactions. Lyophilized peptides were dissolved in 25 mM HEPES-$Na^+$ (pH 7.5), 100 mM NaCl, 1 mM DTT and stored for short periods of time at −20° C. Peptides were labeled with the amine reactive reagent tetramethylrhodamine-5-(and-6)-isothiocyanate (Molecular Probes, Inc. Eugene, Oreg.) using a 2:1 molar ratio of rhodamine to peptide in 0.1 M sodium bicarbonate (pH 9.0) at ambient temperature for 10 hr. Fluorescence data were collected on a PTI Alphascan spectrofluorimeter (Photon Technology Instruments, Santa Clara, Calif.). Dissociation equilibrium constants for Pin1-peptide complexes were determined by measuring the change in fluorescence anisotropy of a set of peptide solutions at constant concentration of peptide each of which contained varied concentrations of Pin1 using the procedure described previously (Vinson et al., Biochemistry 37:10871–10880, 1998). The core binding element determined from this group of peptides is PXpSP, where X cannot be Gly. Surprisingly, the best binding sequences differ from the consensus Pin1-binding sequence of WFYpSPR determined using a degenerate P.Ser-Pro anchored peptide library (Yaffe et al., Science 278:1957–1960, 1997). Furthermore, the dissociation constants roughly segregate into two affinity groups, lower affinity interactions more typical of other WW domain-peptide complexes with dissociation constants greater than 50 μM and higher affinity interactions with dissociation constants less then 30 μM. Several of these peptides yielded crystalline specimens; the most well ordered crystals obtained thus far included the doubly phosphorylated CTD peptide, YpSPTpSPS.

TABLE 2

Dissociation equilibrium constants (μM) for Pin1-peptide complexes[a]

| Labeled Peptide | Pin1 | WW | PPIase |
|---|---|---|---|
| WFYSPFLE (Pintide) (SEQ ID NO:5) | >540 | n.d. | n.d. |
| WFYpSPFLE (Pintide) (SEQ ID NO:6) | 17 ± 2.0 | 44 ± 9.5 | 86 ± 11 |
| VPRpTPV (Cdc25c-T48) (SEQ ID NO:7) | 4.9 ± 1.1 | 7.7 ± 3.3 | n.b. |
| YLGpSPI (Cdc25c-S168) (SEQ ID NO:8) | 69 ± 10 | 91 ± 30 | >400 |
| LYRpSPS (Cdc25c-S214) (SEQ ID NO:9) | 47 ± 7.3 | 72 ± 15 | >500 |
| GSSpSPV (Wee1-S123) (SEQ ID NO:10) | 73 ± 4.9 | n.d. | n.d. |
| PPApTPP (Myt1-T412) (SEQ ID NO:11) | 12 ± 2.1 | 15 ± 4.7 | n.b. |
| PPGpSPP (Myt1-S416) (SEQ ID NO:12) | 80 ± 18 | 126 ± 21 | n.b. |
| STSpTPR (Myt1-T455) (SEQ ID NO:13) | 46 ± 6.5 | 39 ± 12 | n.b. |
| YSPTSPS (CTD) (SEQ ID NO:14) | n.b. | n.b. | n.b. |
| YpSPTSPS (CTD-S2) (SEQ ID NO:15) | 61 ± 6.3 | 110 ± 26 | n.b. |
| YSPTpSPS (CTD-S5) (SEQ ID NO:16) | 30 ± 3.9 | 34 ± 5.9 | >500 |
| YpSPTpSPS (CTD-S2/S5) (SEQ ID NO:17) | 10 ± 0.83 | 34 ± 6.2 | 390 ± 82 |

[a]Errors are deviations from theoretical binding isotherms. All peptides are derived from human proteins except for Pintide.
n.b. is used when there is no detectable binding.
n.d. stands for not determined. The phosphorylation sites are indicated with a single letter amino acid code and numbered according to sequences appearing in public databases.

Overall architecture. To map the recognition surface of Pin1 for the CTD of hyperphosphorylated Pol IIo, we next carried out structural analysis of Pin1 bound to a phosphorylated heptad repeat of the CTD, N-YpSPTpSPS-C. Crystals of the Pin1-YpSPTpSPS complex were obtained and the structure solved by molecular replacement using the published model of Pin1 (Ranganathan et al., Cell 89:875–886, 1997) and refined to 1.84 Å resolution. The CTD phosphopeptide resides in the cavity separating the PPIase domain from the WW domain. Electrostatic, hydrogen bonding, and van der Waals contacts to residues projecting outward from the concave surface of Pin1's WW domain constitute the Pin 1-peptide binding interface (FIG. 1A). No contacts between the bound peptide and the Pin1 PPIase domain are seen in this crystal structure.

Figure 1B:
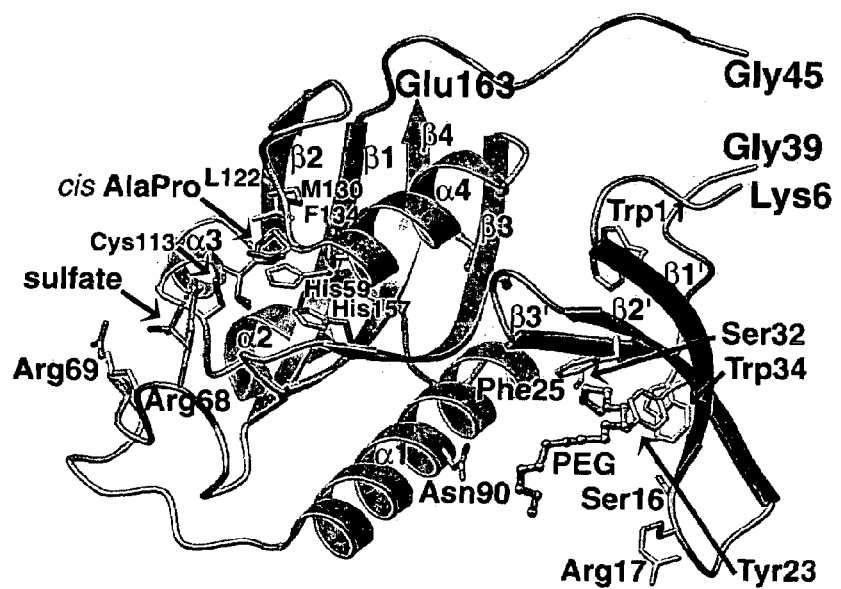
FIG. 1B shows a ribbon representation of the Pin1-PEG complex.

Two conformational differences exist in the current Pin1-peptide co-crystal structure relative to the previously reported structure (Ranganathan et al., Cell 89:875–886, 1997). The first change occurs in the PPIase domain. A nearly 70° rotation of the β1-α1 (residues 64–80) catalytic loop results in an exposed PPIase domain active site. Arg-68 and Arg-69, which confer preferential binding of phosphorylated substrates to the Pin1 PPIase domain, now reside well outside of the proline ring binding pocket formed by His-59, Cys-113, Leu-122, Met-130, Phe-134, and His-157 (FIGS. 1A–B). While a crystal packing interaction maintains this open active site architecture, the observed orientation of the β1-α1 catalytic loop likely reflects the inherent mobility of this selectivity filter when not engaged with a bound phosphopeptide.

A second conformational change in the Pin1 WW domain results in an exaggerated twist in the β-sheet concurrent with a contraction of the concave WW domain ligand binding surface. The upper third of β2' and β3' together with the β2'/β3' turn moves downward over the amino terminal half of the bound CTD peptide. This movement positions Arg-14 and Phe-25 in van der Waals contact with Pro-3' of the CTD peptide and Ser-32 within hydrogen bonding distance of the backbone carbonyl oxygen of Thr-4' on the CTD peptide. The lower half of the β1' and β2' strands together with their connecting loop pivots upward positioning Ser-16 and Arg-17 for hydrogen bonding to the phosphate on P.Ser-5' of the CTD peptide. The complete phosphate binding module of the Pin1 WW domain encompasses the side chains of Ser-16, Arg-17, and Tyr-23 and the backbone amide of Arg-17. A bound water molecule mediates the hydrogen bond between Tyr-23 and the serine phosphate. The Tyr-23/Trp-34 aromatic pair spatially defines the pivot point for all of these structural changes.

Figure 2A:
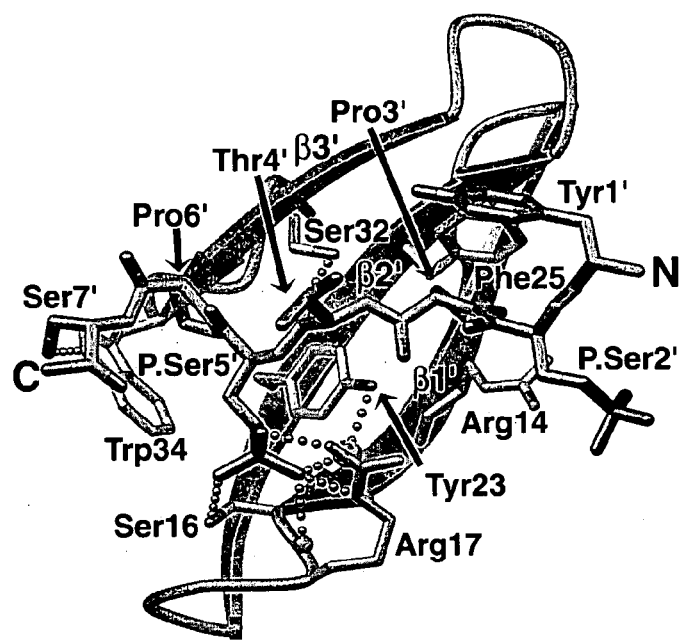
FIG. 2A shows a ribbon diagram of the Pin1 WW domain bound to YpSPTpSPS depicted after a 90° rotation around a vertical axis from the view shown in FIG. 1A. This view is looking on the concave WW domain peptide-binding surface opposite the PPIase domain. The carbon atoms of the CTD peptide are in the foreground compared to the WW side chain atoms. The water molecule mediating Tyr-23 phosphate contacts is shown as a sphere. Hydrogen bonds are shown as dotted spheres.
Figure 2B:
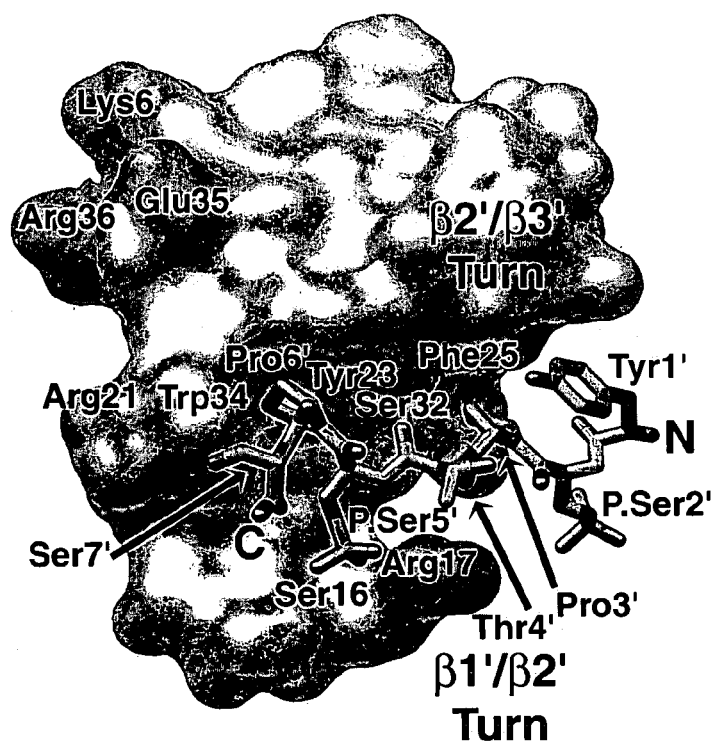
FIG. 2B shows the molecular surface representation of the WW domain—peptide interface after a slight rotation around the vertical axis from the view depicted in FIG. 2A affords this view. The solvent-accessible surface for the Pin1 WW domain residues was calculated in GRASP (Nicholls et al., Proteins 11:281–296, 1991), and the acidic and basic residues depicted as the darker regions adjacent to Lys6, Glu35, Arg36, Arg21, and Arg17.

The aromatic rings of these residues align edge-to-face forming an aromatic clamp which accomodates the backbone atoms of Thr-4' and P.Ser-5' and the ring atoms of Pro-6' of the CTD peptide. Finally, the Ser-7' side chain hydroxyl group forms a hydrogen bond with the protonated indole nitrogen of Trp-34 (FIG. 2A). Tyr-1' and P.Ser-2' of the CTD peptide exhibit a greater degree of flexibility reflected by the weak electron density associated with both of these CTD residues. The entire peptide binds as an extended coil with both P.Ser-Pro peptide bonds in the trans configuration. Modeling of either peptide bond in the cis configuration results in significant steric perturbations at the ligand binding interface that would likely result in a loss of peptide binding. This three-dimensional view supports an extended contact surface limited to five consecutive ligand residues with WW domains.

Figure 3:
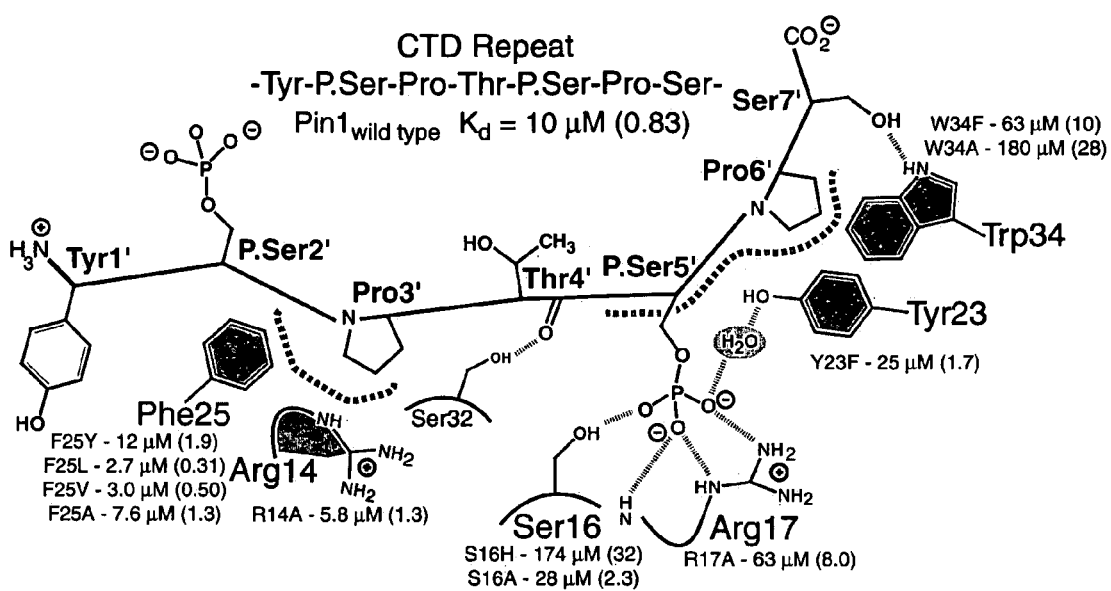
FIG. 3 shows a schematic and energetic view of the Pin1-YpSPTpSPS complex. Pin1 residues are towards the bottom of the figure and are not covalently linked to the larger molecule which represents CTD. Residues participating in van der Waals contacts are highlighted with gray and the extended van der Waals surfaces appear as dotted gray curves. Hydrogen bonds are shown as dashed lines. In the case of the S16H and W34H mutants, some of the apparent binding is likely being contributed by the PPIase domain. Residues are given as single letter codes.
Figure 4A:
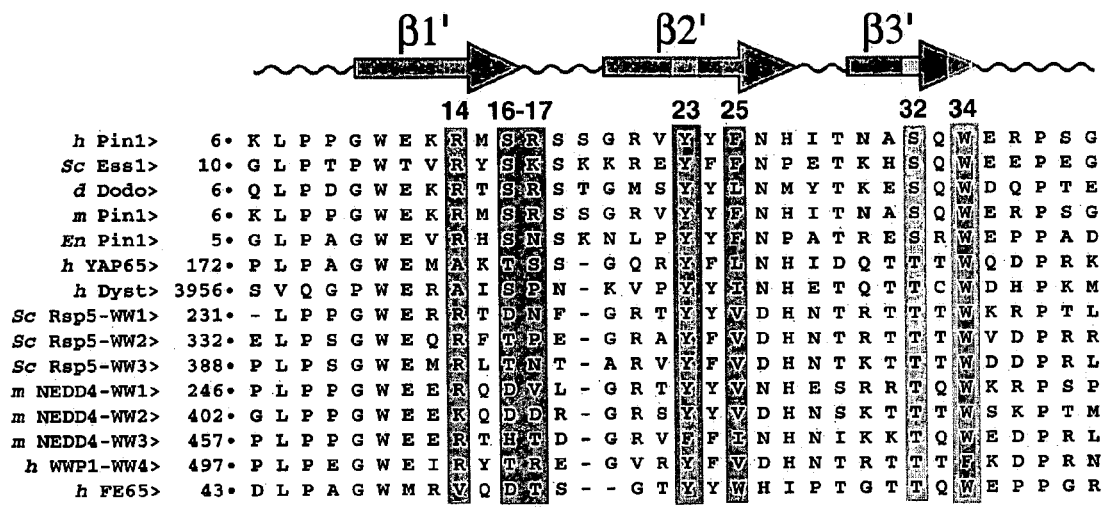
FIG. 4A shows the sequence alignment of 15 WW domains. The secondary structural elements are those of Pin1. The numbers correspond to the first residue on each line for each of the fifteen WW domains. The Darker gray boxes delineate residues participating in phosphate contacts. Shaded boxes corresponding to residues 23 and 24 define residues participating in van der Waals contacts with Pro-3' of the CTD peptide. Shaded residues 14 and 25 contribute to the van der Waals surface sequestering the backbone of residues 4', to 6' as well as the Pro ring of Pro-6'. Light gray boxes corresponding to residue 32 define residues participating in additional hydrogen bonds with the CTD peptide. Residues participating in more then one class of interactions are outlined and coded as described above. h is human, Sc is *Saccharomyces cerevisiae*, d is *Drosophila*, m is mouse, and En is *Emericella nidulans*.

Energetic significance of protein-ligand interactions. To more fully elaborate the WW domain peptide-binding interface quantitatively, the affinities of a limited series of Pin1 mutants for the CTD peptide were measured by fluorescence anisotropy. The results of this analysis are summarized schematically in FIG. 3. Replacement of Arg-17 by Ala results in a 6-fold decrease in binding affinity. In R17A Pin1, the remaining hydrogen bonds between the phosphate on Ser-5' and the side-chain hydroxyl group of Ser-16, the backbone amide of Ala-17, and the water-mediated contact with the Tyr-23 hydroxyl moiety provide an interface for low affinity binding of the phosphopeptide. $E.\ nidulans$ Pin1 contains an Asn residue in place of Arg-17 (FIG. 4A). While neutral, the amide side chain at this position can act as a hydrogen bond donor to the P.Ser phosphate. Therefore, WW domains possessing neutral hydrogen bond donors at positions equivalent to 16, 17, and 23 in Pin1 may provide an energetically acceptable interface for P.Ser/P.Thr-Pro recognition. WW4 of the Nedd4-like HECT domain ubiquitin ligase WWP1 contains a conserved Thr-Arg segment homologous to Ser-16 and Arg-17 of Pin1 (FIG. 4A). Binding analysis of isolated WW1, WW3, and WW4 of WWP1 demonstrates phosphorylation-dependent binding only to WW4. Moreover, several HECT domain ubiquitin ligase WW domains including WW3 of Rsp5 contain an equivalent hydrogen-bonding motif (Thr, Asn, and Tyr—FIG. 4A). In addition to the group IV WW domains, a number of phosphoprotein-binding domains exist including SH2, PTB, STYX, SBF, 14-3-3, and FHA domains (Plowman et al., Proc. Natl. Acad. Sci. USA 96:13603–13610, 1999). While structurally distinct, nearly all such domains utilize Arg residues for the selective recognition of pSer, pThr, and pTyr21,22,23 side chains in a manner analogous to Pin1's WW domain.

Mutations of the other two side chain hydrogen bond donors, Ser-16 and Tyr-23 to Ala and Phe, respectively, each result in a 2.5-fold decrease in binding affinity. Trp-34 constitutes one of two conserved Trp residues found in nearly all WW domains described to date. Together with Tyr-23, this aromatic pair organizes around the Thr-4' and P.Ser-5' backbone, and Pro-6' of the CTD peptide. Replacement of Trp-34 by Phe and Ala cause a 6-fold and 18-fold reduction in binding affinity, respectively. The W34A mutant phenotype is consistent with the reduction of side chain volume leading to less efficient packing of a portion of the CTD peptide backbone and the Pro ring. All Pin1 homologs described to date include one additional residue in the turn linking β1' and β2' (FIG. 4A). This unique structural feature of group IV WW domains may facilitate the conformational change in the β1'/β2' turn that is necessary for the formation of the phosphate binding pocket.

Surprisingly, mutation of Arg-14 and Phe-25, which are predicted to be energetically important based upon the co-crystal structure, results in enhanced binding affinity upon replacement. Structural analysis of the R14A Pin1 mutant without a peptide bound to its WW domain suggests that the WW domain exists in the conformation observed in the current Pin1-phosphopeptide complex rather than that of the wild type unliganded Pin1 complex. The enhanced binding affinity observed for the R14A, F25L, F25V, and F25A mutants might be due in part to preferential stabilization of the peptide-binding WW domain conformation in the absence of ligand.

Figure 4B:
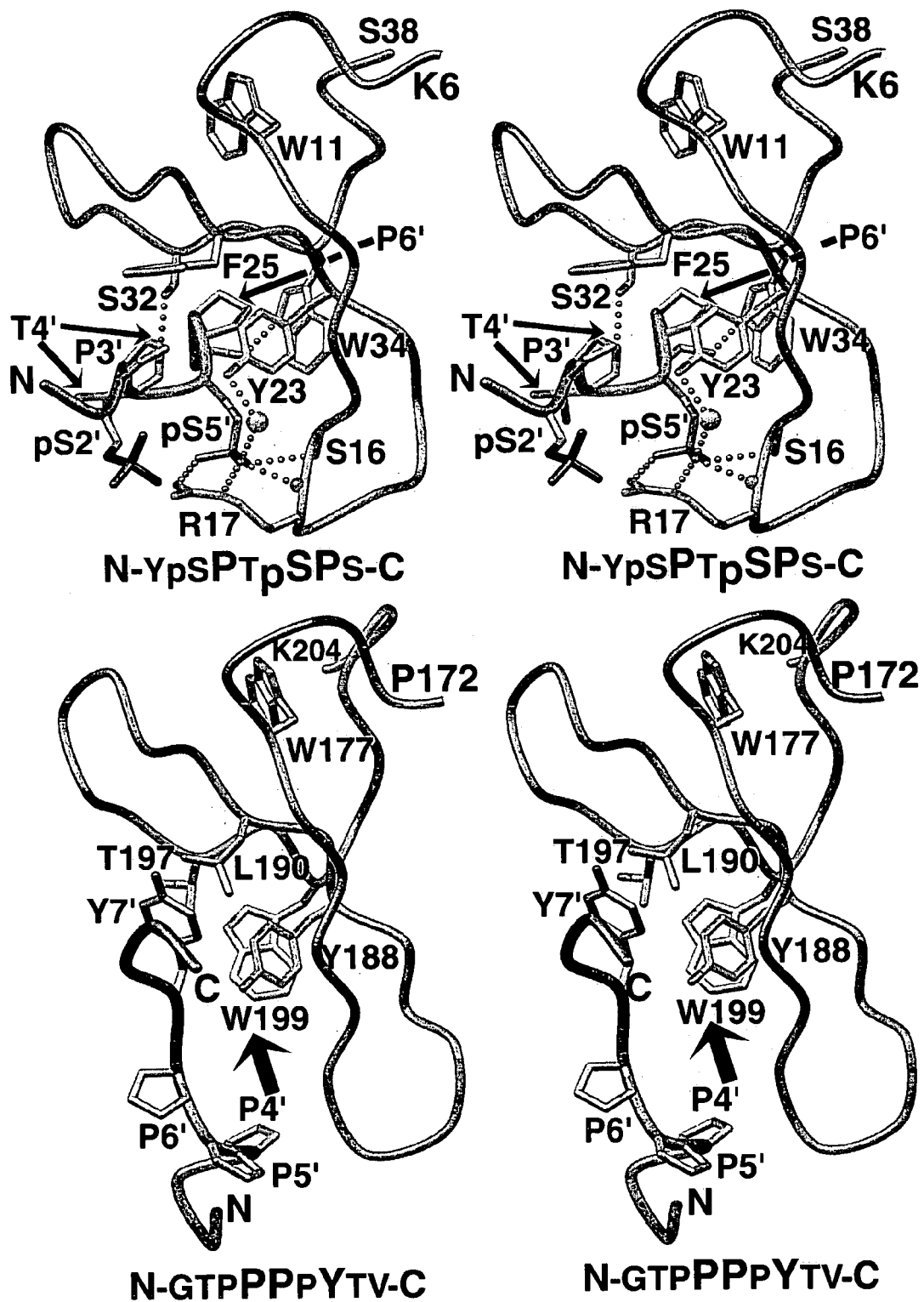
FIG. 4B shows stereo views of the Cα traces of the Pin1-YpSPTpSPS complex (top) and the YAP65-PPXY peptide complex (bottom) aligned with Pin1's WW domain. The figure is labeled as in previous figures. The backbones of the WW domains are now shown as coils. The arrow in the bottom panel depicts the movement necessary to bring the PPXY-containing peptide into alignment with the CTD peptide bound to Pin1. The numbering scheme for YAP65 refers to the human sequence. The numbers in parentheses correspond to the alternate numbering scheme used by Macias et al. (Nature 382:646–649, 1996).

Comparison with other WW domains. The NMR-derived structure of the YAP65 WW domain complexed with a PPxY-containing peptide had a structurally distinct binding interface from that of the CTD heptide bound Pin1 WW domain (FIG. 4b) (Macias et al., Nature 382:646–649, 1996). While this may reflect distinct mechanisms for ligand recognition by group I and group IV WW domains, the recent structural analysis of the dystrophin WW domain in complex with a PPxY-containing peptide argues against this (Huang et al., Nature, submitted (2000)). Modeling the peptide bound to YAP65 in a manner similar to that observed in the Pin1-CTD complex results in a peptide orientation superimposed on the extended binding interface observed for Pin1. However, the direction of the polypeptide chain is reversed. This capacity to bind protein ligands in a bi-directional manner is consistent with the dystrophin WW domain structure and is reminiscent of the alternative binding modes utilized by SH3 domains (Kuriyan, J., Cowburn, D., Annu. Rev. Biophys. Biomol. Struct. 26:259–288, 1997). While Pin1 and dystrophin bind their respective ligands in the opposite N- to C-terminal direction, apart from Pin 1's ability to bind phosphopeptides, the chemical features of the peptide-binding interface are nearly identical.

The picture that emerges is of a rather limited WW domain contact surface that relies on a set of energetically modest side chain interactions, none of which is absolutely essential for ligand binding. Rather, the summed contributions of this module with ligands spanning five consecutive amino acid residues together with interactions with additional modular domains and longer polypeptide targets likely contribute to target selection in WW domain containing proteins such as Pin 1.

While the invention has been described in detail with reference to certain preferred embodiments thereof, it will be understood that modifications and variations are within the spirit and scope of that which is described and claimed.

---

What is claimed is:

1. A method of identifying a Pin1 WW domain binding agent, said method comprising:

determining the ability of a potential binding agent to compete with a known Pin1 WW domain substrate for binding to a Pin1 WW domain by contacting said potential binding agent with said Pin1 WW domain in the presence of said known Pin1 WW domain substrate, wherein the potential binding agent is modeled on a computer to fit spatially into a Pin1 WW domain interaction site using a plurality of atomic coordinates obtained from a Pin1 WW domain crystallized in co-complex with a known Pin1 WW domain binding agent, substrate, or inhibitor, wherein said plurality of atomic coordinates are as set forth in Table 1, and wherein a potential binding agent which competes with a known Pin1 WW domain substrate for binding to a Pin1 WW domain is identified as a Pin1 WW domain binding agent.

2. The method of claim 1, wherein said binding agent is an agonist or antagonist of said Pin1 WW domain.

3. The method of claim 1, wherein said binding agent is an inhibitory agent.

4. The method of claim 3, wherein the inhibitory agent is designed from a known inhibitor.

5. The method of claim 1, wherein said binding agent is a peptide.

6. The method of claim 1, wherein said binding agent is selected from the group consisting of a small molecule, a peptidomimetic, and an antibody.

7. The method of claim 1, further comprising providing a computer with a three dimensional representation of said interaction site and using a computer algorithm to predict a three-dimensional representation of said potential binding agent.

8. The method of claim 1, wherein said potential binding agent is designed de novo.

9. A method of claim 5 of identifying a Pin1 WW domain binding agent, said method comprising:

determining the ability of a potential binding agent to compete with a known Pin1 WW domain substrate for binding to a Pin1 WW domain by contacting said Potential binding agent with said Pin1 WW domain in the presence of said known Pin1 WW domain substrate, wherein the potential binding agent is modeled on a computer to fit spatially into a Pin1 WW domain interaction site using a plurality of atomic coordinates obtained from a Pin1 WW domain crystallized in co-complex with a known Pin1 WW domain binding agent, and wherein said known binding agent has a sequence Tyr-pSer-Pro-Thr-pSer-Pro-Ser (SEQ ID NO:3).

10. The method of claim 9, wherein said plurality of atomic coordinates are as set forth in Table 1.

11. The method of claim 9, further comprising providing a computer with a three-dimensional representation of said interaction site and using a computer algorithm to predict a three-dimensional representation of said potential binding agent.

12. The method of claim 9, wherein said potential binding agent is designed de novo.

13. A computer program on a computer readable medium, said computer program comprising instructions to cause a computer to:

model a potential binding agent that fits spatially into a Pin1 WW domain interaction site using a plurality of atomic coordinates obtained from a Pin1 WW domain crystallized in co-complex with a known Pin1 WW domain binding agent, substrate, or inhibitor, wherein said plurality of atomic coordinates are as set forth in Table 1.

14. A computer program on a computer readable medium, said computer program comprising instructions to cause a computer to:

model a potential binding agent that fits spatially into a Pin1 WW domain interaction site using a plurality of atomic coordinates obtained from a Pin1 WW domain crystallized in co-complex with a known Pin1 WW domain binding agent, wherein said known binding agent has a sequence Tyr-pSer-Pro-Thr-pSer-Pro-Ser (SEQ ID NO:3).

* * * * *